US009925153B2

(12) United States Patent
Vander Jagt et al.

(10) Patent No.: US 9,925,153 B2
(45) Date of Patent: Mar. 27, 2018

(54) THERAPEUTIC AGENTS FOR SKIN DISEASES AND CONDITIONS

(71) Applicant: STC.UNM, Albuquerque, NM (US)

(72) Inventors: David L Vander Jagt, Albuquerque, NM (US); Lorraine M Deck, Albuquerque, NM (US); Robert E Royer, Albuquerque, NM (US); John E Heidrich, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 15/036,968

(22) PCT Filed: Dec. 5, 2014

(86) PCT No.: PCT/US2014/068739
§ 371 (c)(1),
(2) Date: May 16, 2016

(87) PCT Pub. No.: WO2015/085143
PCT Pub. Date: Jun. 11, 2015

(65) Prior Publication Data
US 2016/0287531 A1 Oct. 6, 2016

Related U.S. Application Data

(60) Provisional application No. 61/912,971, filed on Dec. 6, 2013.

(51) Int. Cl.
| *A61K 31/085* | (2006.01) |
| *A61K 31/12* | (2006.01) |
| *A61K 45/06* | (2006.01) |
| *A61K 31/09* | (2006.01) |
| *A61K 31/121* | (2006.01) |
| *A61K 31/137* | (2006.01) |
| *A61K 31/222* | (2006.01) |
| *A61K 31/4406* | (2006.01) |
| *A61K 31/4409* | (2006.01) |
| *A61K 9/00* | (2006.01) |
| *A61K 31/05* | (2006.01) |
| *A61K 31/136* | (2006.01) |
| *A61K 31/444* | (2006.01) |

(52) U.S. Cl.
CPC ............ *A61K 31/12* (2013.01); *A61K 9/0014* (2013.01); *A61K 31/05* (2013.01); *A61K 31/085* (2013.01); *A61K 31/09* (2013.01); *A61K 31/121* (2013.01); *A61K 31/136* (2013.01); *A61K 31/137* (2013.01); *A61K 31/222* (2013.01); *A61K 31/444* (2013.01); *A61K 31/4406* (2013.01); *A61K 31/4409* (2013.01); *A61K 45/06* (2013.01)

(58) Field of Classification Search
CPC .................................................. A61K 31/085
See application file for complete search history.

(56) References Cited

U.S. PATENT DOCUMENTS

2007/0249647 A1* 10/2007 Vander Jagt ......... A61K 31/381
514/277
2013/0178536 A1 7/2013 Vander Jagt et al.

FOREIGN PATENT DOCUMENTS

| GB | 2493041 A | 1/2013 |
| WO | 2009067734 A1 | 6/2009 |
| WO | 2011039175 A1 | 4/2011 |

OTHER PUBLICATIONS

Deck LM, et al. Substituted trans-stilbenes can inhibit or enhance the TPA-induced up-regulation of activator protein-I. BMC Pharmacology, 2008, 8, 19. PMID:19000313.
Solberg NO, et al. Inhibition of NF-KB by treatment with trans-stilbenes concomitantly lowers Alzheimer's plaque formation and microglial activation in APP/PS-I transgenic mouse brain. J Alzheimer's Disease, 2013 submitted.
Yamamoto Y, Gaynor RB. Therapeutic potential of inhibition of the NF-kappaB pathway in the treatment of inflammation and cancer. J Clin. Invest. 2001, 107, 135-142.
Kim HJ, et al. NF-KB and IKK as therapeutic targets in cancer. Cell Death Different. 2006, advanced online publication.
Kaltschmidt B, et al. Signaling via NF-KB in the nervous system. Biochim. Biophys. Acta 2005, 1745, 287-299.
Viatour P, et al. Phosphorylation ofNF-kappaB and IkappaB proteins: implications in cancer and inflammation. Trends Biochem. Sci. 2005, 30, 43-52.
Kumar A, et al. Nuclear factor-KB: its role in health and disease. J. Mol. Med 2004, 82, 434-448.
Hiscott J, et al. Hostile takeovers: viral appropriation of the NF-kappaB pathway. J Clin. Invest. 2001, 107, 143-151.
Barkett M, Gilmore T. Control of apoptosis by Rel/NF-kappaB transcription factors. Oncogene 1999, 18, 6910-6924.
Karin M, Greten FR. NF-KB: linking inflammation and immunity to cancer development and progression. Nature Rev. Immunol. 2005, 5, 749-759.
Herrmann O, et al. IKK mediates ischemia-induced neuronal death. Nat. Med 2005, 11, 1322-1329.
Schmitz ML, et al. NF-KB: A multifaceted transcription factor regulated at several levels. ChemBioChem 2004, 5, 1348-1358.
Gilmore TD. http://people.bu.edu/gilmore/nf-kb/inhibitors May 2003.
Dore S. Unique properties of polyphenol stilbenes in the brain: more than direct antioxidant actions; gene/protein regulatory activity. Neurosignals 2005, 14, 61-70.

(Continued)

*Primary Examiner* — Sahar Javanmard
(74) *Attorney, Agent, or Firm* — Henry D. Coleman; R. Neil Sudol

(57) ABSTRACT

The present invention relates to method(s) of treating a subject afflicted with a skin disease or condition, the method comprising administering to the subject or patient in need a composition comprising a therapeutically effective amount of a substituted cis or trans-stilbene or a stilbene hybrid. A method of treating or reducing the likelihood of a skin disease or condition in a patient is an additional embodiment of the present invention. Preferred pharmaceutical compositions of the invention include nanoemulsions comprising a therapeutically effective amount of a substituted cis or trans-stilbene or stilbene hybrid and at least one antibiotic.

16 Claims, 17 Drawing Sheets

(56) References Cited

OTHER PUBLICATIONS

Kundu JK, Surh YJ. Molecular basis of chemoprevention by resveratrol: NF-KB and AP-I as potential targets. Mut. Res. 2004, 555, 65-80.

Shimizu M, Weinstein B. Modulation of signal transduction by tea catechins and related phytochemicals. Mut. Res. 2005, 591, 147-160.

Renaud S, De Lorgeril M. Wine, platelets, and the French paradox for coronary heart disease. Lancet 1992, 339, 1523-1526.

Jang M, et al. Cancer chemopreventive activity of resveratrol, a natural product derived from grapes. Science 1997, 275, 218-220.

K. Ovesna Z, Horvathova-Kozics K. Structure-activity relationship of trans-resveratrol and its analogs. Neoplasma 2005, 52, 450-455.

Orallo F. Comparative studies of the antioxidant effects of cis- and trans- resveratrol. Cum Med Chem. 2006, 13, 87-98.

Lu M, et al. Efficiency and structure- activity relationship of the antioxidant action of resveratrol and its analogs. Pharmazie 2002, 57, 474-478.

Stojanovic S, et al. Efficiency and mechanism of the antioxidant action of trans-resveratrol and its analogues in the radical liposome oxidation. Arch. Biochem. Biophys. 2001, 391, 79-89.

Stivala LA, et al. Specific structural determinants are responsible for the antioxidant activity and the cell cycle effects of resveratrol. J Biol. Chem. 2001, 276, 22586-22594.

Chung MI, et al. An antiplatelet principle of Veratrum formosanum. Planta Med 1992, 58, 274-276.

Fremont L, et al. Response of plasma lipids to dietary cholesterol and wine polyphenols in rats fed polyunsaturated fat diets. Lipids 2000, 35,991-999.

Murias M, et al. Resveratrol analogues as selective cyclooxygenase-2 inhibitors: synthesis and structure-activity relationship. Bioorg Med Chem, 2004;12:5571-5578.

Shay NF, Banz WJ. Regulation of gene transcription by botanicals: novel regulatory mechanisms. Annu Rev Nutr, 2005;25:297-315.

Juan SH, et al. Mechanism of concentration-dependent induction of heme oxygenase-1 by resveratrol in human aortic smooth muscle cells. Biochem. Pharmacol. 2005, 69, 41-48.

Kundu JK, et al. Resveratrol inhibits phorbol ester-induced expression of COX-2 and activation of NF-kappaB in mouse skin by blocking IkappaB activity. Carcinogenesis 2006, Epub ahead of print.

Lee B, Moon SK. Resveratrol inhibits TNF-K-induced proliferation and matrix metalloproteinase expression in human vascular smooth muscle cells. J Nutr. 2005, 135, 2767-2773.

Liao HF, et al. Resveratrol enhances radiosensitivity of human non-small cell lung cancer NCI-H838 cells accompanied by inhibition of nuclear factor-kappa B activation. J Radiat. Res.(Tokyo) 2005, 46, 387-393.

Bi XL, et al. Resveratrol inhibits nitric oxide and TNF-alpha production by lipopolysaccharide-activated microglia. Int. Immunopharmacol. 2005, 5, 185-193.

Bellucci G, et al. Crown ether catalyzed stereospecific synthesis of Z- and E-stilbenes by Wittig reaction in a solid-liquid two-phase system. Tetrahedron Lett. 1996, 37, 4225-4228.

Lion CJ, et al. Synthesis, antitumor evaluation, and apoptosis-inducing activity of hydroxylated (E)-stilbenes. J Med Chem. 2005,48, 1292-1295.

Kang G, et al. Curcumin suppresses lipopolysaccharide-induced cyclooxygenase-2 expression by inhibiting activator protein 1 and nuclear factor kappab bindings in BV2 microglial cells. J Parmaco.l Sci. 2004, 94, 325-328.

Wieder T, et al. Piceatannol, a hydroxylated analog of the chemopreventive agent resveratrol, is a potent inducer of apoptosis in the lymphoma cell line BJAB and in primary, leukemic lymphoblasts. Leukemia 2001, 15, 1735-1742.

Ashikawa K, et al. Piceatannol inhibits lNF-induced NF-KB activation and NF-KB-mediated gene expression through suppression of IKBK kinase and p65 phosphorylation. J. Immunol. 2002,169,6490-6497.

Rimando AM, et al. Cancer chemopreventive and antioxidant activities of pterostilbene, a naturally occurring analogue of resveratrol. J. Agric. Food Chem. 2002, 50, 3453-3457.

Tolomeo M, et al. Pterostilbene and 3'-hydroxypterostilbene are effective apoptosis-irtducing agents in MDR and BCR-ABL-expressing leukemia cells. Int. J. Biochem. Cell. Biol. 2005, 3 7, 1709-1726.

Manna SK, et al. Resveratrol suppresses lNF-induced activation of nuclear transcription factors NF-KB, activator protein-I, and apoptosis: potential role of reactive oxygen intermediates and lipid peroxidation. J. Jmmunol. 2000, 164, 6509-6519.

Sizemore N, et al. Distinct roles of the IKB kinase a and bin liberating nuclear factor KB (NF-KB) from IB and in phosphorylating the p65 subunit of NF-KB. J. Biol. Chem. 2002, 277, 3863-3869.

Schlesier K, et al. Assessment of antioxidant activity by using different in vitro methods. Free Rad Res. 2002, 36, 177-187.

Re R, et al. Antioxidant activity applying an improved ABTS radical cation decolorization assay. Free Rad Biol. Med 1999, 26, 1231-1237.

Benzie IF, Strain JJ. Ferric reducing/antioxidant power assay: direct measure of total antioxidant activity of biological fluids and modified version for simultaneous measurement of total antioxidant power and ascorbic acid aoncentrations. Methods Enzymol. 1999, 299, 15-27.

Li Q, Verma IM. NF-KB regulation in the immune system. Nature Reviews Immunology, 2002, 2, 725-728. PMID: 12360211.

Shaulian E, Karin M. AP-1 in cell proliferation and survival. Oncogene, 2001, 20, 2390-2400. PMID: 11402335.

Hess J, et al AP-1 subunits: quarrel and harmony among siblings. J Cell Sci, 2004 117, 5965-5973. PMID: 15564374.

Shyu YJ, et al. Visualization of AP-1 NF-kappaB ternary complexes in living cells by using a BiFC-based FRET. Proc Natl Acad Sci, 2008, 105, 151-156. PMID: 18172215.

Shen G, et al. Regulation of Nrf2, NF-KB, and AP-1 signaling pathways by chemopreventive agents. Antioxid Redox Signal, 2005, 7, 1648-1663. PMID: 16356127.

Weber WW, et al. Activation of NFkB is inhibited by curcumin and related enones. Bioorg Med Chem, 2006, 14, 2450-2461. PMID:16338138.

Weber WW, et al. TPA-induced up-regulation of activator protein-I can be inhibited or enhanced by analogs of the natural product curcumin. Biochem Pharmacol, 2006, 72, 928-940. PMID:16934760.

Heynekamp JJ, et al. Substituted trans-stilbenes, including analogs of the natural product resveratrol, inhibit the human tumor necrosis factor alpha-induced activation of transcription factor nuclear factor kappB. J Med Chem, 2006, 49, 7182-7189. PMID: 17125270.

* cited by examiner

FIGURE 9
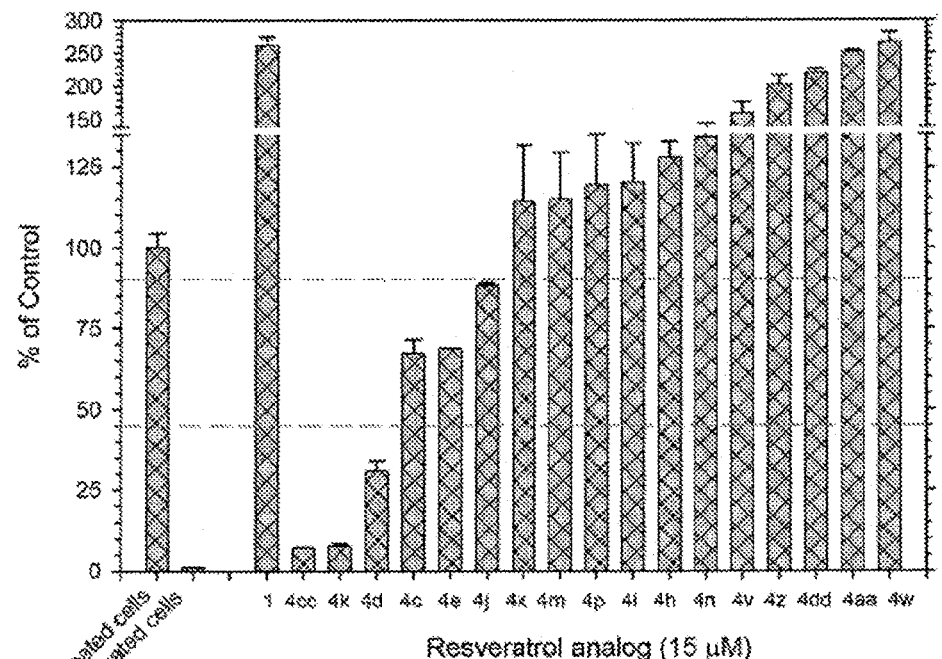
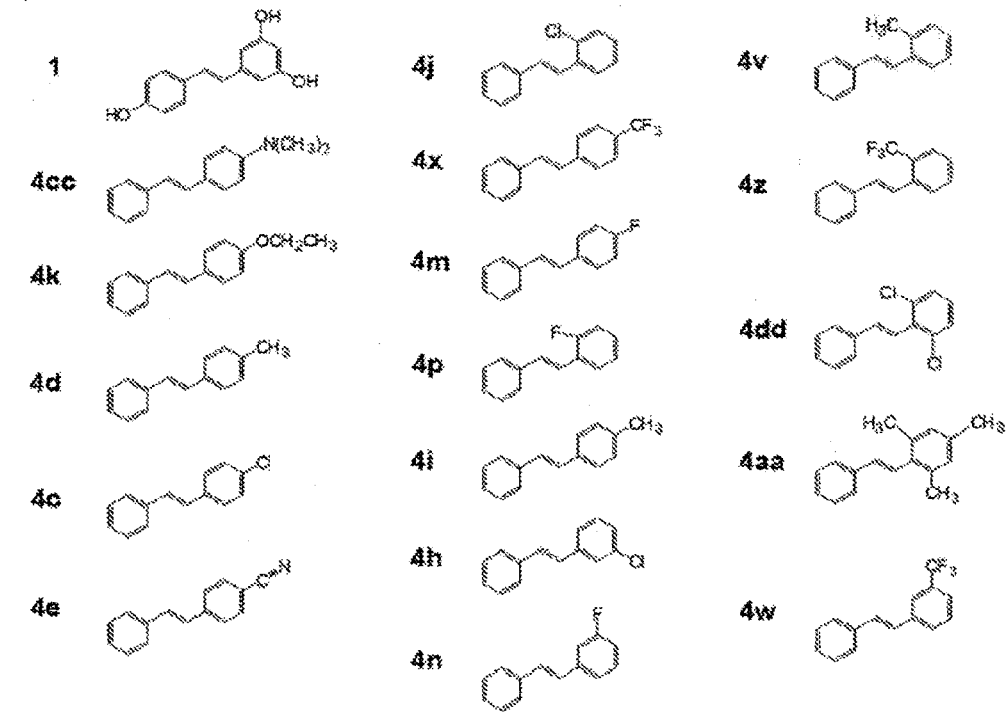

FIGURE 10
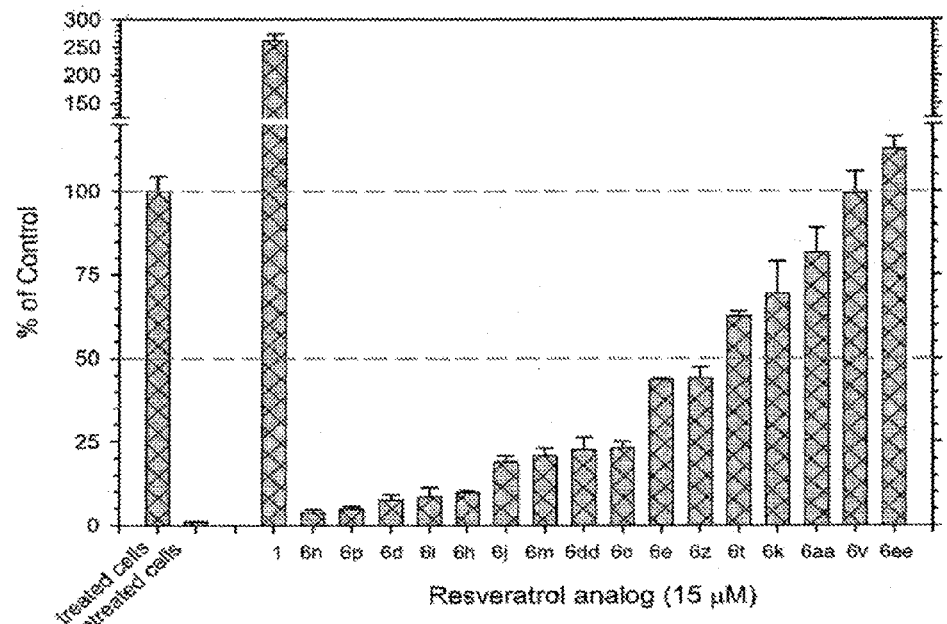
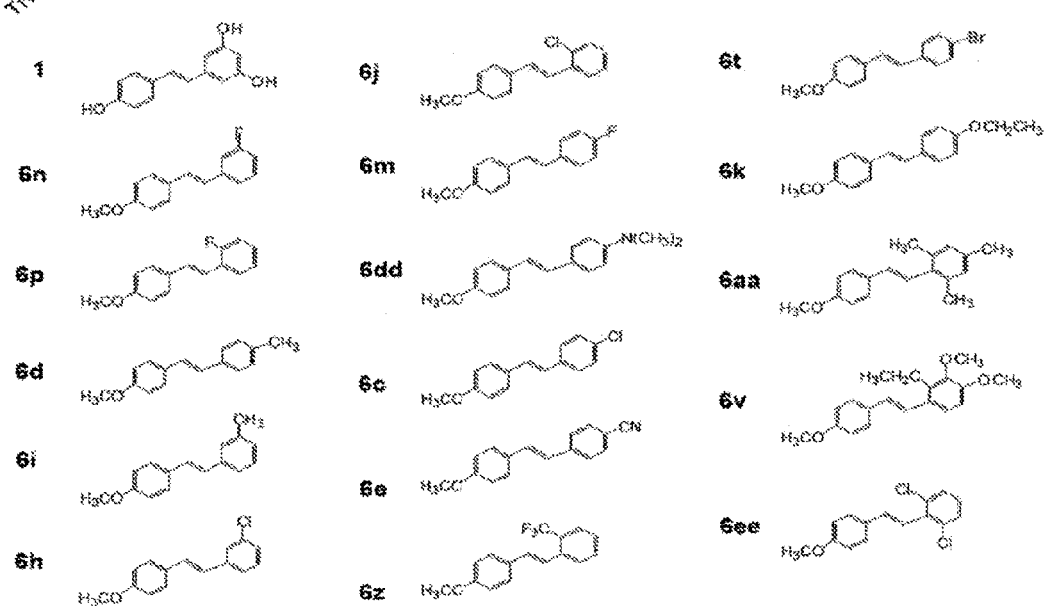

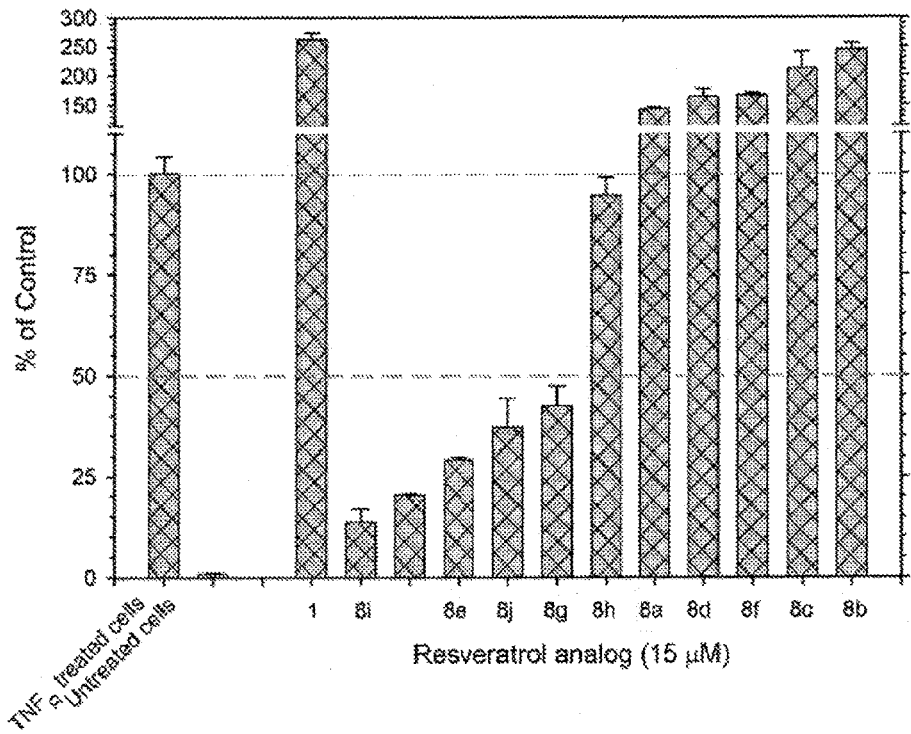
FIGURE 11
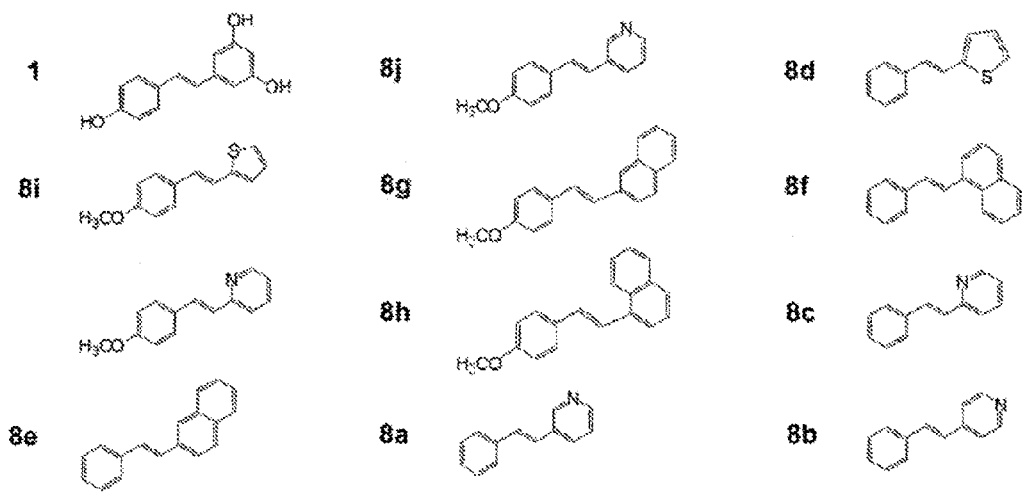

FIGURE 13
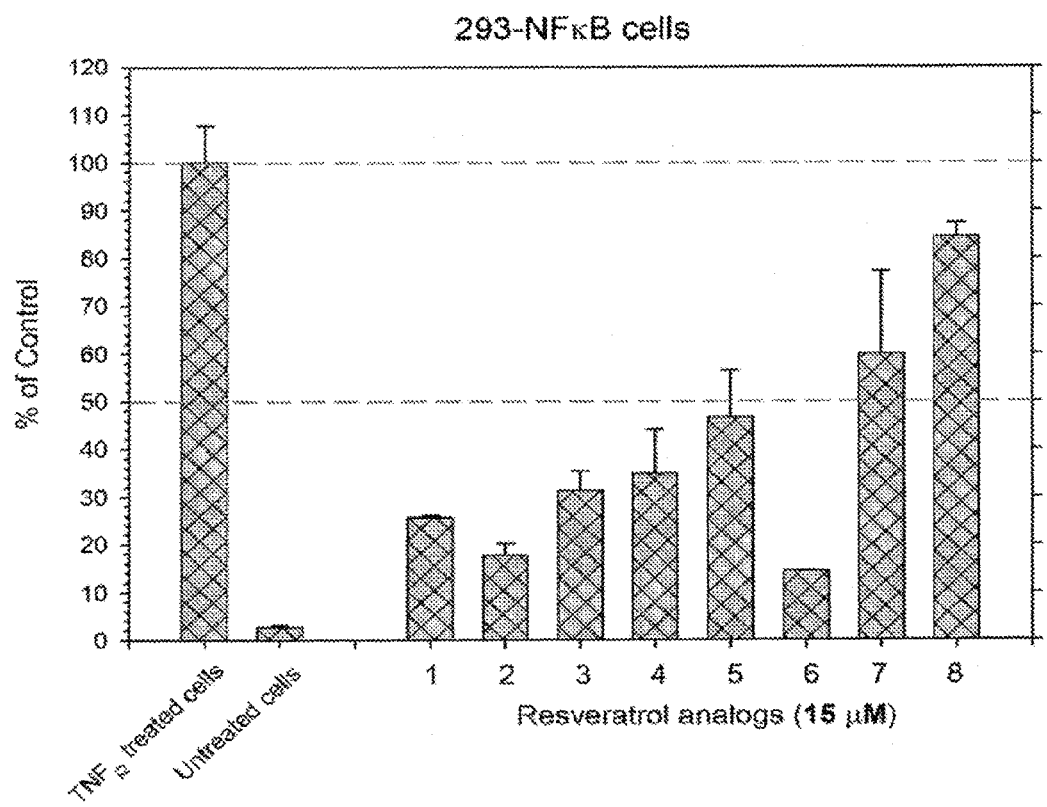
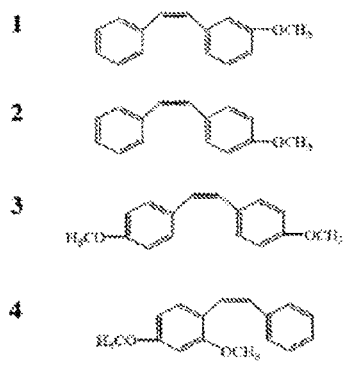
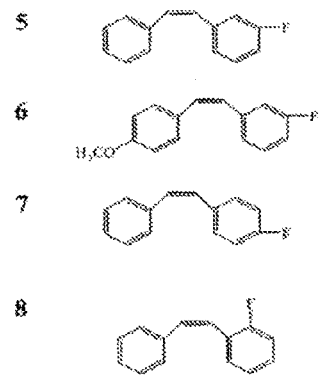

FIGURE 14
Trans-Stilbenes Resveratrol and LD55
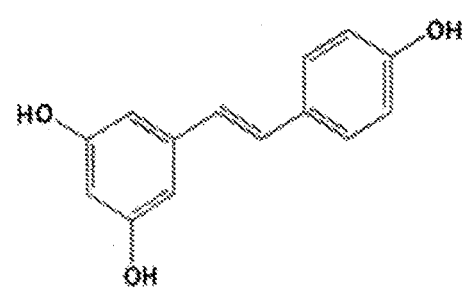
Resveratrol
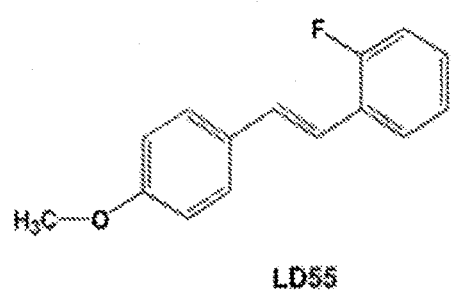
LD55

FIGURE 15
A.
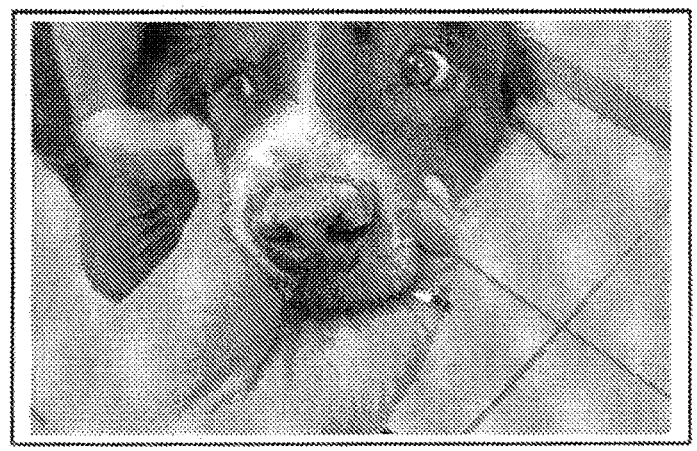
B.

FIGURE 17
A.
B.
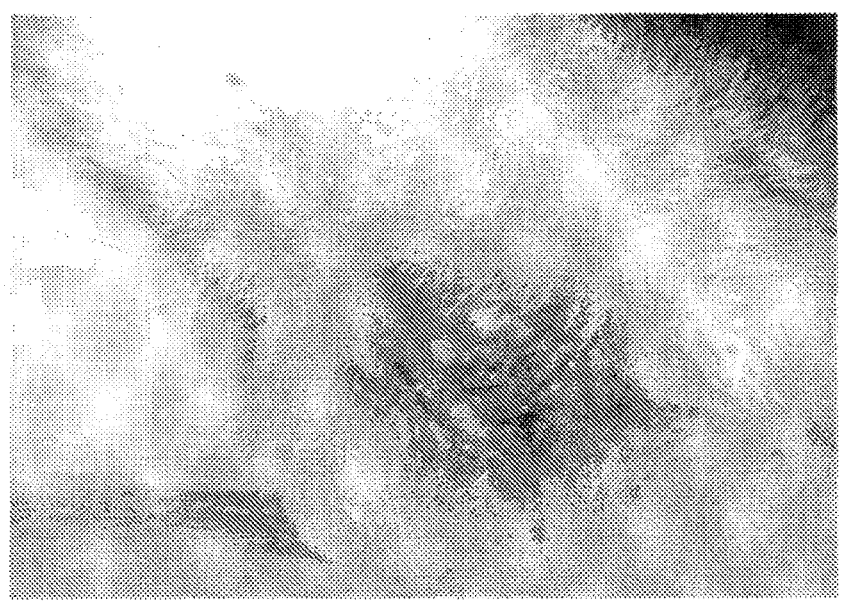

THERAPEUTIC AGENTS FOR SKIN DISEASES AND CONDITIONS

CROSS-REFERENCE TO RELATED APPLICATIONS

This application is a national phase application of PCT/2014/068739 which claims priority from U.S. Provisional Patent Application Ser. No. 61/912,971, filed Dec. 6, 2013, the entire contents of each of said applications being incorporated by reference herein.

FIELD OF THE INVENTION

The present invention relates to method(s) of treating a subject afflicted with a skin disease or condition as otherwise described herein, the method comprising administering to the subject or patient in need thereof a composition comprising a therapeutically effective amount of a therapeutic agent, such as a substituted cis or trans-stilbene or a stilbene hybrid (a compound not specifically identified as a stilbene, but maintaining at least part of the stilbene structure), preferably a reserveratrol analog as otherwise described herein, and in particular, LD-55.

Preferred pharmaceutical compositions of the invention include nanoemulsions comprising a therapeutically effective amount of a therapeutic agent described herein such as a substituted cis or trans-stilbene or a stilbene hybrid and at least one antibiotic.

BACKGROUND OF THE INVENTION

The nuclear factor κB (NF-κB) family of transcription factors in mammals consists of homo- and hetero-dimeric combinations of five related proteins (p50, p52, p65/RelA, c-Rel, and RelB) that have a marked influence on the expression of numerous genes involved in immunity and inflammation, as well as cellular stress responses, growth, and apoptosis. Diverse pathways activate NF-κB, and control of these pathways is increasingly viewed as an approach to chemotherapy in the many diseases that have an associated inflammatory component, including cancer, stroke, Alzheimer's disease and diabetes.[1-10] Activation of NF-κB occurs through multiple pathways. The classical pathway is triggered by binding of pro-inflammatory cytokines (TNFα and IL-1) and of a number of pathogens to several different receptors in the TNF-receptor and Toll-like/IL-1 receptor superfamilies. This leads to recruitment to the plasma membrane and activation of the IκB-kinase complex (IKK) consisting of IKKα and IKKβ kinases, and the scaffold protein NEMO/IKKγ, as well as a number of IKK-associated proteins. The main NFκB that is activated in the classical pathway is the p50/p65 heterodimer that exists in the cytoplasm as a complex with inhibitory protein IκBα. Activation of IKK primarily through IKKβ results in phosphorylation of IκBα on Ser32 and Ser36, followed by polyubiquitination and degradation of IκBα by the 26S proteasome, allowing p50/p65 to translocate to the nucleus.

Release of p50/p65 from IκBα also can be achieved by IKK-independent pathways triggered by DNA damage or oxidative stress that result in phosphorylation of IκBα on Ser residues other than Ser32 or Ser36, again leading to proteosomal degradation of IκBα. This signaling pathway involves a number of kinases including the MAP kinase p38 and casein kinase 2. There is also an oxidative stress pathway that phosphorylates IκBα on Tyr residues, leading to release of p50/p65 without proteosomal degradation of IκBα. Superimposed on the complex activation of p50/p65 is additional downstream regulation of the DNA-binding properties of p50/p65 through phosphorylation, acetylation and peptidyl-prolyl isomerization. Mostly this occurs in p65 and provides multiple points for control of NF-κB activation in a cell-specific and environment-specific manner. A wide range of kinases can phosphorylate p50/p65, which appears essential for the transactivation potential of p50/p65. This includes phosphorylation at many different sites, especially in p65, which adds to the complex regulation of NF-κB.[4,10]

There are also alternative pathways to activation of NF-κB that result in formation of homo- or hetero-dimers other than p50/p65. A major alternative pathway, which is independent of IKKβ and NEMO, involves the IKKα homodimer whose activation is triggered by cytokines (other than TNFα), ligands such as CD40, and by certain viruses. This pathway requires recruitment of NF-κB-inducing kinase (NIK) with subsequent phosphorylation and activation of the IKKα homodimer. Activated IKKα phosphorylates p100, which is subsequently ubiquitinated and processed by the proteosome to p52. p52 and RelB then form a heterodimer that translocates to the nucleus. As with p50/p65, the p52/RelB heterodimer is further regulated by phosphorylation.[4]

A large number of compounds including natural products have been reported to inhibit activation of NF-κB at one or more sites in the complex pathways of activation.[11] This includes resveratrol (3,4',5-trihydroxystilbene, 1), a polyphenolic

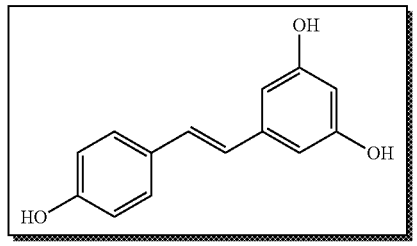

1 phytochemical that is found in numerous foods and is especially abundant in red wine. It has been proposed that the anti-oxidant activity of resveratrol is responsible for the French Paradox;[12-14] this relates to the low incidence of cardiovascular disease in a French population with high intake of saturated fat.[15] Both trans and cis isomers of resveratrol occur as phytothemicals, and both possess biological activities. Most studies of the biological activities of resveratrol and of synthetic stilbene analogs of resveratrol have focused on trans isomers. Resveratrol has been studied extensively in the context of carcinogenesis as a chemoprevention agent. All three stages of carcinogenesis, i.e., initiation, promotion and progression, have been reported to be inhibited by resveratrol.[16] Because resveratrol exhibits anti-oxidant activity, which is based upon its phenolic groups, much of the research on resveratrol and on polyphenolic analogs of resveratrol has focused on anti-oxidant properties.[17-21] In addition, the multiple biological activities reported for resveratrol, which in addition to its cardioprotective and anti-carcinogenic activity also includes inhibition of platelet aggregation, modulation of lipoprotein metabolism, anti-inflammatory and vasorelaxing activities,[17,22-24] are often ascribed to the anti-oxidant properties of resveratrol. However, the oral bioavailability of resveratrol is low due to rapid metabolism, and the amount of resveratrol in dietary sources such as red wine is low compared to other polyphenols. Consequently, the circulating levels of resveratrol are low suggesting that the direct anti-oxidant effects of resveratrol are unlikely to explain its biological activities.[12] Therefore, there has been extensive interest in the ability of resveratrol and other plant polyphenols to affect signaling pathways, including NF-κB.[25] Signaling through NF-κB has been shown to be involved in the ability of resveratrol to induce heme oxygenase-1,[26] inhibit phorbol ester-induced expression of COX-2,[27] inhibit TNFα-induced proliferation of smooth muscle cells,[28] enhance the radiosensitivity of lung cancer cells,[29] and inhibit nitric oxide and TNFα production by LPS-activated microglia.[30]

A model of the overlapping metabolic and inflammatory signaling and sensing pathways in adipocytes and macrophages that influence inflammation is provided by FIG. 2. As shown in FIG. 2, signals from various mediators converge on the inflammatory signaling pathways, including the kinases JNK and IKK. These pathways lead to the production of additional inflammatory mediators such as NF-κB and AP-1 through transcriptional regulation as well as to the direct inhibition of insulin signaling. Opposing the inflammatory pathways are transcriptional factors from the PPAR and LXR families, which promote nutrient transport and metabolism and antagonize inflammatory activity.

BRIEF DESCRIPTION OF THE FIGURES

FIGS. 7-12 show the effects of compounds according to the present invention in AP-1 assays as otherwise described herein.

FIG. 13 shows the inhibition of the TNFα-induced activation of NF-κB by certain substituted cis-stilbenes (Scheme 4 and example).

FIG. 14 shows the trans-stilbenes reservatrol and LD55, a particularly active compound against skin diseases and conditions pursuant to the present invention.

FIGS. 15-17 show the effects of LD55 on certain skin conditions in animals tested with the compound.

SUMMARY OF THE INVENTION

Figure 4:
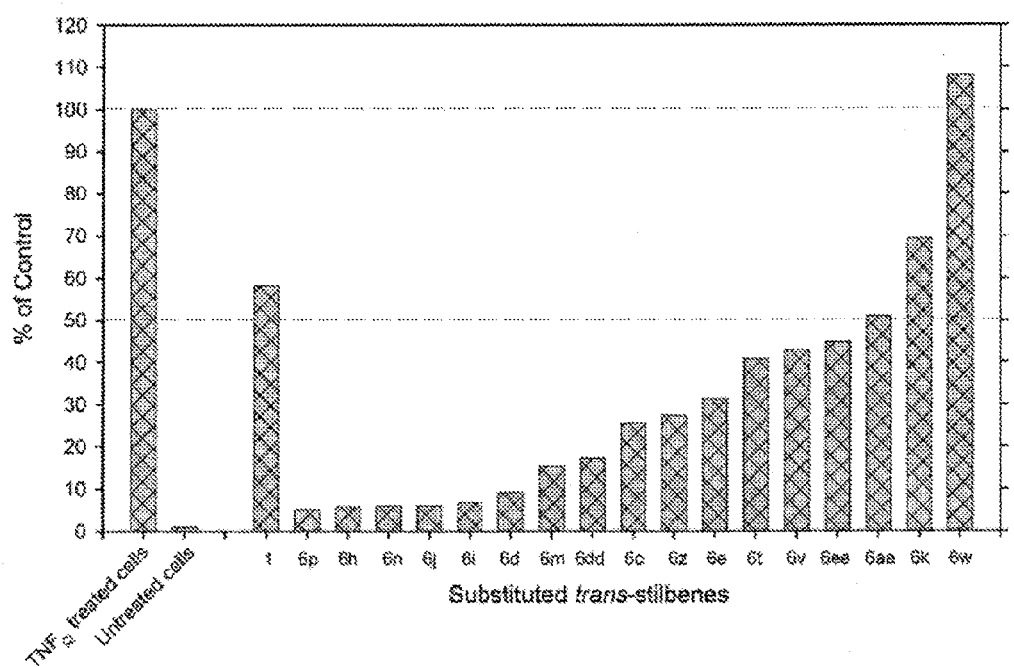
FIG. 4 shows the inhibition of the TNFα-induced activation of NF-κB by a series of trans-stilbenes devoid of phenolic groups (Scheme 2).

The present invention provides a method of a treating a subject afflicted with a skin disease or condition as otherwise described herein. The method includes administering to the subject a therapeutically effective amount of a cis- or trans-stilbene or stilbene hybrid, preferably a substituted cis or trans-stilbene, more preferably an analog of the natural product resveratrol, most often LD55 (FIG. 4). The composition optionally includes a pharmaceutically acceptable carrier. In some embodiments, the composition inhibits NF-κB or AP-1 activity in effecting a therapeutic result for the skin disease or condition which is treated. In some aspects of the invention methods of reducing the likelihood of a disease or condition as otherwise described herein comprise administering to a subject or patient at risk for a disease or condition as otherwise herein an effective amount of a compound as otherwise disclosed herein.

The present method relates to a method for treating or reducing the likelihood of a skin disease or condition in a subject or patient in need thereof comprising administering an effective amount of a therapeutic agent such as cis- or trans-stilbene compound according to the general chemical structure (this structure represents both the cis- and trans-stilbene structures):

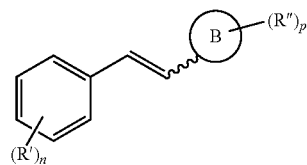

Where each R' is independently H, OH, halogen (F, Cl, Br, I), an optionally substituted —(CH$_2$)$_m$XR, —(CH$_2$)$_m$R or —(CH$_2$)$_m$C(O)R$^3$ group, an optionally substituted C$_1$-C$_6$ (preferably, C$_1$-C$_3$) alkyl group, —CN, NO$_2$, a —(CH$_2$)$_m$NR$^1$R$^2$ group, a —(CH$_2$)$_m$C(O)NR$^1$R$^2$ group or a —(CH$_2$)$_m$OC(O)NR$^1$R$^2$ group;

R is an optionally substituted C$_1$-C$_6$ hydrocarbyl group (preferably a C$_1$-C$_3$ optionally substituted alkyl group), an optionally substituted heterocylic group, an optionally substituted heteroaryl group or an optionally substituted C$_2$-C$_6$ acyl group;

R$^1$ and R$^2$ are each independently H or an optionally substituted C$_1$-C$_6$ hydrocarbyl (preferably a C$_1$-C$_3$ alkyl) group;

R$^3$ is H, OH or an optionally substituted —O—(C$_1$-C$_6$) hydrocarbyl (preferably a C$_1$-C$_3$ alkyl) group, an optionally substituted heterocyclic group or an optionally substituted heteroaryl group;

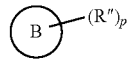

is an optionally substituted aryl or heteroaryl group wherein each R" is independently H, OH, halogen (F, Cl, Br, I), an optionally substituted —(CH$_2$)$_m$XR, —(CH$_2$)$_m$R$^a$ or —(CH$_2$)$_m$C(O)R$^{3a}$ group, an optionally substituted C$_1$-C$_6$ hydrocarbyl group, (preferably, a C$_1$-C$_3$ alkyl group), —CN, NO$_2$, a —(CH$_2$)$_m$NR$^{1a}$R$^{2a}$ group, a —(CH$_2$)$_m$C(O)NR$^{1a}$R$^{2a}$ group or a —(CH$_2$)$_m$OC(O)NR$^{1a}$R$^{2a}$ group;

Where R$^a$ is an optionally substituted C$_1$-C$_6$ hydrocarbyl group (preferably a C$_1$-C$_3$ optionally substituted alkyl group), an optionally substituted heterocyclic group, an optionally substituted heteroaryl group or an optionally substituted C$_2$-C$_6$ acyl group;

R$^{1a}$ and R$^{2a}$ are each independently H or an optionally substituted C$_1$-C$_6$ hydrocarbyl (preferably a C$_1$-C$_3$ alkyl) group; and $R^{3a}$ is H, OH, or an optionally substituted —$(CH_2)_m$—O—($C_1$-$C_6$) hydrocarbyl (preferably a $C_1$-$C_3$ alkyl) group, an optionally substituted heterocyclic group or an optionally substituted heteroaryl group;

X is O or S (preferably O);

m is an integer from 0-6, preferably 0-3;

n is an integer from 0-3;

p is an integer from 0-3, or a pharmaceutically acceptable salt, hydrate or solvate thereof.

In a particularly preferred embodiment of the present invention, it has been discovered that the compounds reservatrol, 1a (LD-55) and 2a identified below, in effective amounts, as well as other compounds disclosed either alone or in any combination, represent an effective therapy to inhibit and/or treat skin diseases and conditions in a patient in need. In addition, methods according to the present invention may be used to inhibit or reduce the likelihood that a patient with a skin disease or condition, will have these disease states and/or conditions occur or worsen.

Thus, in preferred methods according to the present invention an effective amount of one or more compounds according to the chemical structures below (reservatrol, compound 1a, compound 2a, other below-listed compounds which are stilbenes or hybrid stilbenes, alone or in any combination are administered to a patient in need to inhibit, reduce the likelihood of and/or treat skin conditions as otherwise described herein.

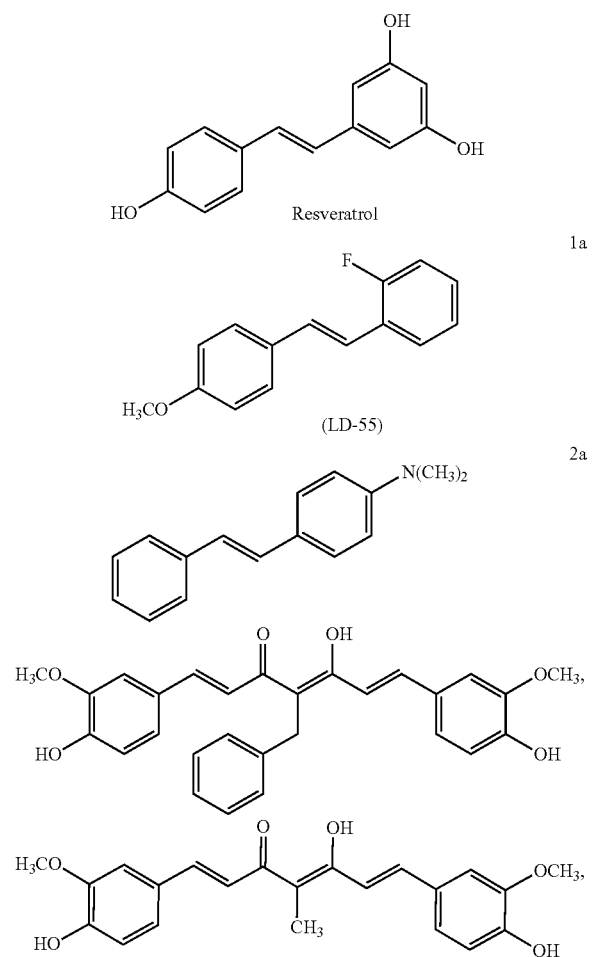

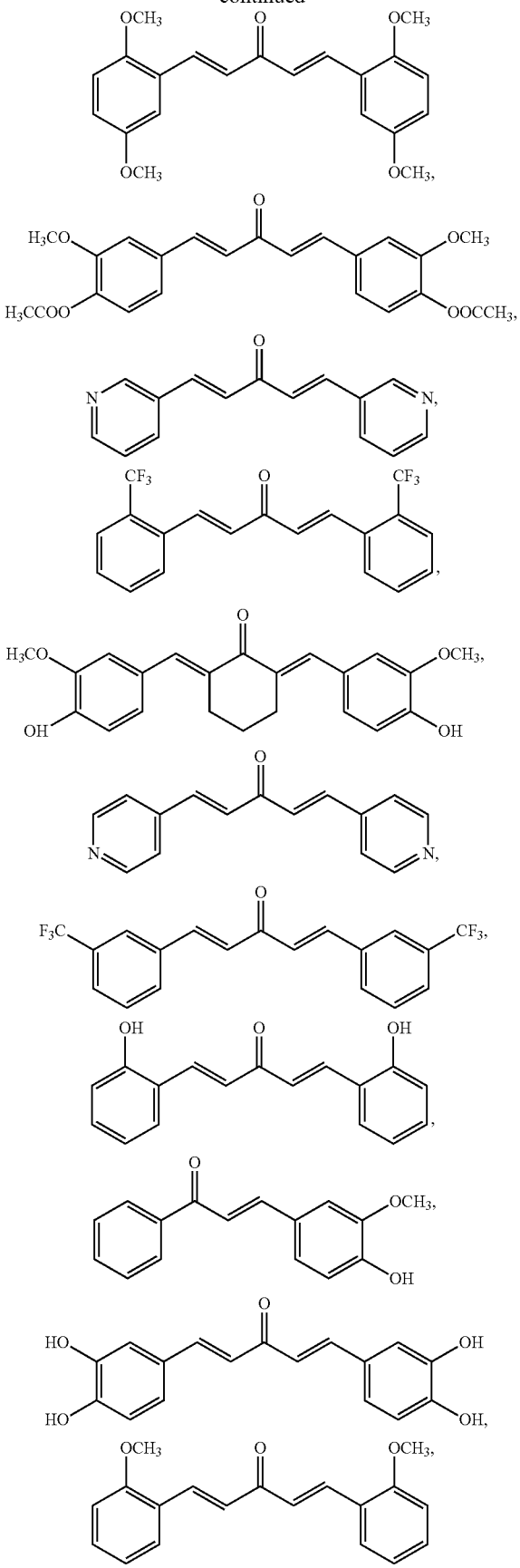

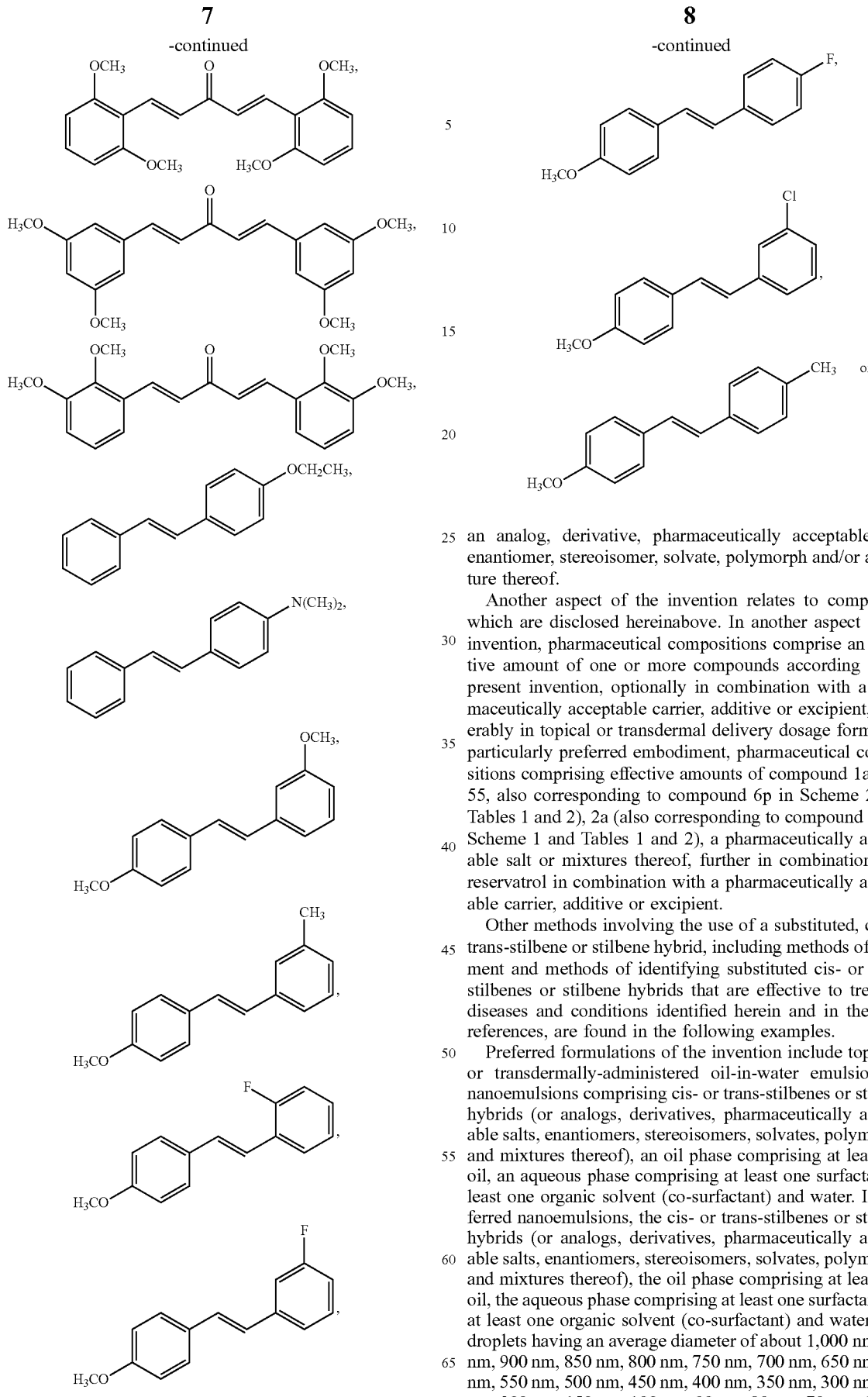

an analog, derivative, pharmaceutically acceptable salt, enantiomer, stereoisomer, solvate, polymorph and/or a mixture thereof.

Another aspect of the invention relates to compounds which are disclosed hereinabove. In another aspect of the invention, pharmaceutical compositions comprise an effective amount of one or more compounds according to the present invention, optionally in combination with a pharmaceutically acceptable carrier, additive or excipient, preferably in topical or transdermal delivery dosage form. In a particularly preferred embodiment, pharmaceutical compositions comprising effective amounts of compound 1a (LD-55, also corresponding to compound 6p in Scheme 2, and Tables 1 and 2), 2a (also corresponding to compound 4cc in Scheme 1 and Tables 1 and 2), a pharmaceutically acceptable salt or mixtures thereof, further in combination with reservatrol in combination with a pharmaceutically acceptable carrier, additive or excipient.

Other methods involving the use of a substituted, cis- or trans-stilbene or stilbene hybrid, including methods of treatment and methods of identifying substituted cis- or trans-stilbenes or stilbene hybrids that are effective to treat the diseases and conditions identified herein and in the cited references, are found in the following examples.

Preferred formulations of the invention include topically or transdermally-administered oil-in-water emulsions or nanoemulsions comprising cis- or trans-stilbenes or stilbene hybrids (or analogs, derivatives, pharmaceutically acceptable salts, enantiomers, stereoisomers, solvates, polymorphs and mixtures thereof), an oil phase comprising at least one oil, an aqueous phase comprising at least one surfactant, at least one organic solvent (co-surfactant) and water. In preferred nanoemulsions, the cis- or trans-stilbenes or stilbene hybrids (or analogs, derivatives, pharmaceutically acceptable salts, enantiomers, stereoisomers, solvates, polymorphs and mixtures thereof), the oil phase comprising at least one oil, the aqueous phase comprising at least one surfactant, the at least one organic solvent (co-surfactant) and water form droplets having an average diameter of about 1,000 nm, 950 nm, 900 nm, 850 nm, 800 nm, 750 nm, 700 nm, 650 nm, 600 nm, 550 nm, 500 nm, 450 nm, 400 nm, 350 nm, 300 nm, 250 nm, 200 nm, 150 nm, 100 nm, 90 nm, 80 nm, 70 nm, 60 nm, 50 nm, 40 nm, 30 nm, 20 nm, 10 nm, or 9, 8, 7, 6, 5, 4, 3, 2 or 1 nm (most preferably about 50-75 nm).

The compounds and methods of the invention are useful for treating or reducing the likelihood of any skin disease or condition characterized by inflammation, for example Acrodermatitis, Cellulite, Cryotherapy, Cutaneous skin tags, Dermatitis herpetiformis, Dry skin, Ectodermal dysplasia, Epidermolysis bullosa, Erythema multiforme, Erythema nodosum, Erythema toxicum, Granuloma annulare, Henoch-Schonlein purpura, Hyperelastic skin, Ichthyosis vulgaris, Idiopathic or primary livedo reticularis, Intertrigo, Keratosis pilaris, Lamellar ichthyosis, Lichen planus, Lichen simplex chronicus, Milia, Nikolsky's sign, Perioral dermatitis, Pityriasis rosea, Pityriasis rubra pilaris, Polymorphic light eruption, Preauricular tag or pit, Purpura Pyogenic granuloma, Sebaceous cyst, Seborrheic dermatitis, Seborrheic keratosis, Skin and hair changes during pregnancy, Skin blushing/flushing, Skin discoloration—bluish, Skin graft, Skin lesion biopsy, Skin lumps, Skin turgor, Stasis dermatitis and ulcers, Striae, Subcutaneous emphysema, Vesicles, Wood's lamp examination, Xanthoma, Xeroderma pigmentosa, Xerosis, Eczema, Impetigo, Itching, Psoriasis, Rashes, Scleroderma, Skin Aging, Skin Cancer, Skin Infections and Skin Pigmentation Disorders. The present methods are particularly and unexpectedly effective in resolving these skin disease states and conditions, both providing a rapid resolution of symptoms and in some instances, cure rates which are substantially greater than prior art methods, especially given that these skin diseases and conditions are often difficult to treat.

Notably, pharmaceutical compositions of the invention prove useful in the treatment of skin cancers and have proven especially effective in the treatment of squamous cell carcinoma of the skin.

It should be understood that the methods and formulations of the invention are generally useful for treating any skin disease or condition that can be ameliorated by inhibiting or otherwise modulating the activity of NFkB or AP-1.

DETAILED DESCRIPTION OF THE INVENTION

Unless otherwise specified, "a," "an," "the," and "at least one" are used interchangeably and mean one or more than one.

The following terms shall be used to describe the present invention. In instances where a term is not defined herein, such term is given its common meaning by those of ordinary skill in the art.

The term "patient" or "subject" refers to a mammal, preferably a human, including a domesticated mammal, in need of treatment or therapy to which compounds according to the present invention are administered in order to treat a condition or disease state otherwise described herein.

The term "compound", as used herein, unless otherwise indicated, refers to any specific chemical compound disclosed herein and includes in context, tautomers, regioisomers (especially cis/trans—see below), geometric isomers, and where applicable, optical isomers thereof, as well as pharmaceutically acceptable salts, solvates and polymorphs thereof. Within its use in context, the term compound generally refers to a single compound, but also may include other compounds such as stereoisomers, regioisomers and/or optical isomers (including in some instances, racemic mixtures) as well as specific enantiomers or enantiomerically enriched mixtures of disclosed compounds. The compounds of this invention include all stereoisomers where relevant (e.g., both cis and trans isomers—as represented by a bond) and all optical isomers of the present compounds (eg., R and S enantiomers), as well as racemic, diastereomeric and/or other mixtures of such isomers, as well as all pharmaceutically acceptable salt forms, solvates, polymorphs and pro-drug forms of the present compounds, where applicable. The present invention relates both to the cis—and trans-stilbene structures and related hybrid stilbene structures, as generally presented herein and their methods of use.

Cis ("Z" or Zusammen)    Trans ("E" or Entgagen)

The term "modulate" means, with respect to disease states or conditions, modulated through (e.g, by binding) or having an effect on NF-κB or AP-1 to produce, either directly or indirectly; an improvement or lessening of a condition or disease state which was, prior to administration of a compound according to the present invention, sub-optimal and in many cases, debilitating and even life threatening. Modulation may occur by virtue of agonist activity, antagonist activity or mixed agonist/antagonist activity (depending on the receptor site). In most/many instances, the term modulate shall mean direct or indirect inhibition of NF-κB or AP-1 alone or within the context of treating a disease or condition associated with same.

The term "independently" is used herein to indicate that the variable, which is independently applied, varies independently from application to application.

The term "non-existent" or "absent" refers to the fact that a substituent is absent and the group to which such substituent is attached forms an additional bond with an adjacent atom or group.

The term "optionally substituted" means optional substitution with the specified groups, radicals or moieties. It should be noted that any atom with unsatisfied valences in the text, schemes, examples and tables herein is assumed to have the hydrogen atom(s) to satisfy the valences.

The term "skin disease or condition" is used to describe disease states or conditions of the skin which may be treated using compounds according to the present invention. Exemplary skin diseases or conditions which may be treated include, for example, Acrodermatitis, Cellulite, Cryotherapy, Cutaneous skin tags, Dermatitis herpetiformis, Dry skin, Ectodermal dysplasia, Epidermolysis bullosa, Erythema multiforme, Erythema nodosum, Erythema toxicum, Granuloma annulare, Henoch-Schonlein purpura, Hyperelastic skin, Ichthyosis vulgaris, Idiopathic or primary livedo reticularis, Intertrigo, Keratosis pilaris, Lamellar ichthyosis, Lichen planus, Lichen simplex chronicus, Milia, Nikolsky's sign, Perioral dermatitis, Pityriasis rosea, Pityriasis rubra pilaris, Polymorphic light eruption, Preauricular tag or pit, Purpura Pyogenic granuloma, Sebaceous cyst, Seborrheic dermatitis, Seborrheic keratosis, Skin and hair changes during pregnancy, Skin blushing/flushing, Skin discoloration—bluish, Skin graft, Skin lesion biopsy, Skin lumps, Skin turgor, Stasis dermatitis and ulcers, Striae, Subcutaneous emphysema, Vesicles, Wood's lamp examination, Xanthoma, Xeroderma pigmentosa, Xerosis, Eczema, Impetigo, Itching, Psoriasis, Rashes, Scleroderma, Skin Aging, Skin Cancer, Skin Infections and Skin Pigmentation Disorders, among others. It is unexpected that compounds according to the present invention may be particularly useful in treating these disease states and/or conditions, especially when the compounds are formulated in pharmaceutical compositions in topical and/or transdermal delivery dosage forms.

The term "hydrocarbyl" refers to any radical containing carbon and hydrogen, which may be straight, branch-chained or cyclic in nature. Hydrocarbons include linear, branched and cyclic hydrocarbons, including alkyl groups, alkylene groups and unsaturated hydrocarbon groups, which may be optionally substituted. Hydrocarbyl groups may be fully saturated or unsaturated, containing one or more double ("ene") or triple ("yne") bonds.

"Alkyl" refers to a fully saturated monovalent hydrocarbyl radical containing carbon and hydrogen, and which may be cyclic, branched or a straight chain. Examples of alkyl groups are methyl, ethyl, n-butyl, n-hexyl, n-heptyl, n-octyl, isopropyl, 2-methylpropyl, cyclopropyl, cyclopropylmethyl, cyclobutyl, cyclopentyl, cyclopentylethyl, cyclohexylethyl and cyclohexyl. Preferred alkyl groups are $C_1$-$C_6$ alkyl groups.

"Alkylene" refers to a fully saturated hydrocarbon which is divalent (may be linear, branched or cyclic) and which is optionally substituted. Other terms used to indicate substituent groups in compounds according to the present invention are as conventionally used in the art. Thus, the term alkylene aryl includes alkylene phenyl such as a benzyl group or ethylene phenyl group, alkylaryl, includes alkylphenyl such a phenyl group which has alkyl groups as substituents, etc.

"Aryl" refers to a substituted or unsubstituted monovalent aromatic radical having a single ring (e.g., phenyl) or multiple condensed rings (e.g., naphthyl, anthracenyl, phenanthryl) and can be can be bound to compound according to the present invention at any position on the ring(s).

The term "heteroaryl" refers to an optionally substituted (at varying positions as appropriate within context) heterocyclic aromatic ring system having one or more nitrogen, oxygen, or sulfur atoms in the ring, such as imidazolyl, furyl, thiophene (thienyl), pyrrole, pyridine, pyrimidinyl, quinoline, isoquinoline, indole, isoindole, triazole, tetrazole, pyrazolyl, oxazolyl, thiazolyl, benzofuranyl, benzothiophenyl, carbazolyl, benzoxazolyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, among numerous others. Monocyclic and fused ring systems are contemplated for use in the present invention.

The term "heterocycle" or "heterocyclic" shall mean an optionally substituted moiety which is cyclic and contains at least one atom other than a carbon atom, such as a nitrogen, sulfur, oxygen or other atom. A heterocyclic ring shall contain up to four atoms other than carbon selected from nitrogen, sulfur and oxygen. These rings may be saturated or have unsaturated bonds. Fused rings are also contemplated by the present invention. A heterocycle according to the present invention is an imidazole, a piperazine, piperidine, furan, pyrrole, imidazole, thiazole, oxazole or isoxazole group; all optionally substituted, among numerous others, including those groups described as heteroaryl groups hereunder. Depending upon its use in context, a heterocyclic ring may be saturated and/or unsaturated. In instances where a heterocyclic ring is fully unsaturated, there is overlap with the term "heteroaryl".

"Alkoxy" as used herein refers to an alkyl group bound through an ether linkage; that is, an "alkoxy" group may be represented as —O-alkyl where alkyl is as defined above.

The term "cyclic" shall refer to a carbocyclic or heterocyclic group, preferably a 5- or 6-membered ring, but may include 4 and 7-membered rings, but may, in context, refer to a group with two or more fused rings.

The term "unsubstituted" shall mean substituted only with hydrogen atoms. The term "substituted" shall mean, within the chemical context of the compound defined, a substituent (each of which substituents may itself be substituted) selected from a hydrocarbyl (which may be substituted itself, preferably with an optionally substituted alkyl or halogen (fluoro) group, among others), preferably an alkyl (generally, no greater than about 12 carbon units in length), an optionally substituted aryl (which also may be heteroaryl and may include an alkylenearyl or alkyleneheteroaryl), an optionally substituted heterocycle (especially including an alkyleneheterocycle), $CF_3$, halogen (especially fluoro), thiol, hydroxyl, carboxyl, oxygen (to form a keto group), $C_1$-$C_8$ alkoxy, $C_1$-$C_8$ alkoxyether, CN, nitro, an optionally substituted amine (e.g., an alkyleneamine or a $C_1$-$C_6$ monoalkyl or dialkyl amine), $C_1$-$C_8$ acyl, $C_1$-$C_8$ alkylester, $C_1$-$C_8$ alkyleneacyl (keto), $C_1$-$C_8$ alkylene ester, carboxylic acid, alkylene carboxylic acid, $C_1$-$C_8$ thioester, $C_2$-$C_8$ ether, $C_1$-$C_8$ mono- or dithioether, $C_1$-$C_8$ diether (alkoxyether), amide (amido or carboxamido), substituted amide (especially mono- or di-alkylamide) or alkyleneamide, an optionally substituted carbamate or urethane group, wherein an alkylene group or other carbon group not otherwise specified contains from 1 to 8 carbon units long (alternatively, about 2-6 carbon units long) and the alkyl group on an ester group is from 1 to 8 carbon units long, preferably up to 4 carbon units long. Various optionally substituted moieties may be substituted with 5 or more substituents, preferably no more than 3 substituents and preferably from 1 to 3 substituents.

The term "fused aryl ring" includes fused carbocyclic aromatic rings or ring systems. Examples of fused aryl rings include benzo, naphtho, fluoreno, and indeno.

The term "annulene" refers to aryl groups that are completely conjugated monocycle hydrocarbons. Annulenes have a general formula of where n is an even number, or $C_nH_{n+1}$, where n is an odd number. Examples of annulenes include cyclobutadiene, benzene, and cyclooctatetraene. Annulenes present in an aryl group will typically have one or more hydrogen atoms substituted with other atoms such as carbon.

When a group is present more than once in any formula or scheme described herein, each group (or substituent) is independently selected, whether explicitly stated or not. For example, for the formula —C(O)—$NR_2$ each of the two R groups is independently selected.

The term "geometric isomer" shall be used to signify an isomer of a compound according to the present invention wherein a chemical group or atom occupies different spatial positions in relation to double bonds or in saturated ring systems having at least three members in the ring as well as in certain coordination compounds. Thus "cis" and "trans" isomers are geometric isomers as well as isomers of for example, cyclohexane and other cyclic systems. In the present invention, the double bond between the aryl and aryl/heteroaryl (B) group is a trans double bond. In all other cases, a double bond may be cis or trans.

The term "coadministration" or "combination therapy" is used to describe a therapy in which at least two active compounds in effective amounts are used to treat cancer or another disease state or condition as otherwise described herein at the same time. Although the term coadministration preferably includes the administration of two active compounds to the patient at the same time, it is not necessary that the compounds be administered to the patient at the same time, although effective amounts of the individual compounds will be present in the patient at the same time. In skin cancer aspects of the invention, trans-stilbene compounds according to the present invention may be administered with one or more anti-cancer agent, including antimetabolites, alkylating agents, topoisomerase I and topoisomerase II inhibitors as well as microtubule inhibitors, among others. Anticancer compounds for use in the present invention include those described above, and mixtures thereof, among others. Preferred anticancer agents for use in the present invention in coadministration with one or more of the compounds disclosed herein include for example, fluorouracil, imiquimod, vismodegib, aldesleukin, dacarbazine, ipilimumab, vemurafenib or mixtures thereof.

Co-administration of one of the present compounds with another anticancer agent as otherwise described herein will often result in a synergistic enhancement of the anticancer activity of the other anticancer agent, an unexpected result. One or more of the present compounds may also be coadministered with another bioactive agent (e.g., an antibiotic, antiviral agent, antihyperproliferative disease agent, agents which treat skin diseases or conditions or are used on the skin, among others or as otherwise described herein), depending upon the desired therapeutic outcome and the disease state or condition treated.

"Antibiotics" include, but are not limited to, bacitracin, neomycin, mupirocin, polymyxin B, chlorhexidine digluconate, Gentamicin, Kanamycin, Neomycin, Netilmicin, Tobramycin, Paromomycin, Spectinomycin, Geldanamycin, Herbimycin, Rifaximin, Streptomycin, Ertapenem, Doripenem, Imipenem/Cilastatin, Meropenem, Cefadroxil, Cefazolin, Cephalothin, Cephalexin, Cefaclor, Cefamandole, Cefoxitin, Cefprozil, Cefuroxime, Cefixime, Cefdinir, Cefditoren, Cefoperazone Cefotaxime, Cefpodoxime, Ceftazadime, Ceftibuten, Ceftizoxime Ceftriaxone, Cefepime, Ceftaroline fosamil, Ceftobiprole, Teicoplanin, Vancomycin, Telavancin, Daptomycin, Oritavancin, WAP-8294A, Azithromycin, Clarithromycin, Dirithromycin, Erythromycin, Roxithromycin, Telithromycin, Spiramycin, Clindamycin, Lincomycin, Aztreonam, Furazolidone, Nitrofurantoin, Oxazolidonones, Linezolid, Posizolid, Radezolid, Torezolid, Amoxicillin, Ampicillin, Azlocillin, Carbenicillin, Cloxacillin Dicloxacillin, Flucloxacillin, Mezlocillin, Nafcillin, Oxacillin, Penicillin G, Penicillin V, Piperacillin, Temocillin, Ticarcillin, Amoxicillin/clavulanate, Ampicillin/sulbactam, Piperacillin/tazobactam, Ticarcillin/clavulanate, Bacitracin, Colistin, Polymyxin B, Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, Mafenide, Sulfacetamide, Sulfadiazine, Sulfadimethoxine, Sulfamethizole, Sulfamethoxazole, Sulfasalazine, Sulfisoxazole, Trimethoprim-Sulfamethoxazole, Sulfonamidochrysoidine, Demeclocycline, Doxycycline, Vibramycin Minocycline, Tigecycline, Oxytetracycline, Tetracycline, Clofazimine, Capreomycin, Cycloserine, Ethambutol, Rifampicin, Rifabutin, Rifapentine, Arsphenamine, Chloramphenicol, Fosfomycin, Fusidic acid, Metronidazole, Mupirocin, Platensimycin, Quinupristin/Dalfopristin, Thiamphenicol, Tigecycline and Tinidazole and combinations thereof.

"Treat", "treating", and "treatment", etc., as used herein, refer to any action providing a benefit to a patient at risk for or afflicted with a disease, including improvement in the condition through lessening or suppression of at least one symptom, delay in progression of the disease, prevention, inhibition or delay in the onset of the disease, etc.

Treatment, as used herein, encompasses both prophylactic and therapeutic treatment. Cis- and trans-stilbene and hybrid stilbene compounds of the invention can, for example, be administered prophylactically to a mammal in advance of the occurrence of disease, Prophylactic administration is effective to decrease the likelihood of the subsequent occurrence of disease in the mammal, or decrease the severity of disease that subsequently occurs. Alternatively, cis- and trans-stilbene or stilbene hybrid compounds of the invention can, for example, be administered therapeutically to a mammal that is already afflicted by disease. In one embodiment of therapeutic administration, administration of the cis- and trans-stilbene or stilbene hybrid compounds is effective to eliminate the disease; in another embodiment, administration of the cis- and trans-stilbene and stilbene hybrid compounds is effective to decrease the severity of the disease or lengthen the lifespan of the mammal so afflicted.

"Pharmaceutically acceptable" as used herein means that the compound or composition is suitable for administration to a subject to achieve the treatments described herein, without unduly deleterious side effects in light of the severity of the disease and necessity of the treatment.

"Inhibit" as used herein refers to the partial or complete elimination of a potential effect, while inhibitors are compounds that have the ability to inhibit.

The present invention includes the compositions comprising the pharmaceutically acceptable salt. i.e., the acid or base addition salts of compounds of the present invention and their derivatives. The acids which may be used to prepare the pharmaceutically acceptable acid addition salts of the aforementioned base compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among others.

Pharmaceutically acceptable base addition salts may also be used to produce pharmaceutically acceptable salt forms of the compounds according to the present invention. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (and, calcium and magnesium), ammonium or water-soluble amine addition salts such as N-methylglucamine-(meglumine), and the lower alkanolammonium and other base salts of pharmaceutically acceptable organic amines, among others.

Regardless of the mechanism, the compounds of the present invention may be used to treat skin disease states or conditions in patients or subjects who suffer from those conditions or disease states or are at risk for those conditions. In this method a compound in an effective amount is administered to a patient in need of therapy to treat or reduce the likelihood of the occurrence of the condition(s) or disease state(s). The compounds and methods of the invention are useful for treating or reducing the likelihood of any skin disease or condition characterized by inflammation, including Acrodermatitis, Cellulite, Cryotherapy, Cutaneous skin tags, Dermatitis herpetiformis, Dry skin, Ectodermal dysplasia, Epidermolysis bullosa, Erythema multiforme, Erythema nodosum, Erythema toxicum, Granuloma annulare, Henoch-Schonlein purpura, Hyperelastic skin, Ichthyosis vulgaris, Idiopathic or primary livedo reticularis, Intertrigo, Keratosis pilaris, Lamellar ichthyosis, Lichen planus, Lichen simplex chronicus, Milia, Nikolsky's sign, Perioral dermatitis, Pityriasis rosea, Pityriasis rubra pilaris, Polymorphic light eruption, Preauricular tag or pit, Purpura Pyogenic granuloma, Sebaceous cyst, Seborrheic dermatitis, Seborrheic keratosis, Skin and hair changes during pregnancy, Skin blushing/flushing, Skin discoloration—bluish, Skin graft, Skin lesion biopsy, Skin lumps, Skin turgor, Stasis dermatitis and ulcers, Striae, Subcutaneous emphysema, Vesicles, Wood's lamp examination, Xanthoma, Xeroderma pigmentosa, Xerosis, Eczema, Impetigo, Itching, Psoriasis, Rashes, Scleroderma, Skin Aging, Skin Cancer, Skin Infections and Skin Pigmentation Disorders, among others. While not being limited by way of theory, it is unexpected that the compounds which are used to treat skin diseases and conditions according to the present invention would be so effective at amelioaring these disease states and conditions, many by a topical and/or transdermal route of administration. As it was thought that many of these compounds were metabolized to more active species, it is unexpected that the activity would be as significant as it is in the skin of a patient.

Compositions according to the present invention may be administered by any conventional means known in the art. Pharmaceutical formulations include those suitable for oral, rectal, nasal, topical (including buccal and sub-lingual), vaginal or parenteral (including intramuscular, sub-cutaneous and intravenous) administration, but compositions which are administered by topical and/or transdermal route of administration directly at the site in the skin of the disease state or condition to be treated are preferred. Compositions according to the present invention may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. When desired, the above described formulations may be adapted to provide sustained release characteristics of the active ingredient(s) in the composition using standard methods well-known in the art.

In the pharmaceutical aspect according to the present invention, the compound(s) according to the present invention is formulated preferably in admixture with a pharmaceutically acceptable carrier. In general, it is preferable to administer the pharmaceutical composition orally, but certain formulations may be preferably administered parenterally and in particular, in intravenous or intramuscular dosage form, as well as via other parenteral routes, such as transdermal, buccal, subcutaneous, suppository or other route, including via inhalation intranasally. Oral dosage forms are preferably administered in tablet or capsule (preferably, hard or soft gelatin) form. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity.

Compositions suitable for parenteral injection may comprise physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants.

These compositions may also contain adjuvants such as preserving, wetting, emulsifying, and/or dispersing agents. Prevention of microorganism contamination of the compositions can be accomplished by the addition of various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, sesame seed oil, glycerol, tetrahydrofurfuryl alcohol, polyethylene glycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may contain suspending agents, as for example, ethoxylated isostearyl alcohols, polyoxyethylene sorbitol or sorbitan esters, microcrystalline cellulose, aluminum metahydroxide, bentonite, agar-agar, or tragacanth, or mixtures of these substances, and the like.

Compositions for rectal or vaginal administration, where applicable, can be prepared by mixing an active agent and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the active.

Dosage forms for topical administration include ointments, powders, sprays and inhalants. The compound(s) are admixed under sterile conditions with a physiologically acceptable carrier, and any preservatives, buffers, and/or propellants that may be required. Opthalmic formulations, eye ointments, powders, and solutions are also contemplated as being within the scope of this invention.

Disease Treatment Using the Present Compounds

Treatment, as defined herein, is the amelioration of the symptoms associated with disease. Symptoms may be reduced either by decreasing the level of the disease itself, or by decreasing the symptoms associated with the disease. The subject of the treatment is preferably a mammal, such as a domesticated farm animal (e.g., cow, horse, pig) or pet (e.g., dog, cat). More preferably, the subject is a human.

As noted herein, and without being bound by any particular theory, one mechanism by which administration of the cis or trans-stilbene or a stilbene hybrid compounds according to the present invention may treat disease is through inhibition of the activity of AP-1 or NF-κB. Inhibition of NF-κB results in a decrease in NF-κB activity, and includes direct inhibition and indirect inhibition. Direct inhibition is the direct effect of a cis or trans-stilbene compound on NF-κB and its activity. For example, one type of direct inhibition of NF-κB is a block of NF-κB DNA interactions. Indirect inhibition, on the other hand, involves the effect of a cis or trans-stilbene or a stilbene hybrid on other compounds involved in the regulation of NF-κB that leads to a decrease in NF-κB activity. For example, as phosphorylation of the NF-κB regulator IκB by IκB kinases (IKK) or Src family kinases (SFK) results in a dysregulation of NF-κB, and an according increase in NF-κB activity, inhibition of IKK or SFK by cis- or trans-stilbene compounds provides an example of indirect inhibition.

Inhibition of AP-1 results in a decrease in AP-1 activity, and includes direct inhibition and indirect inhibition. Direct inhibition is the direct effect of a cis or trans-stilbene or stilbene hybrid compound on AP-1 (or its subunits) and its activity. Indirect inhibition, on the other hand, involves the effect of a cis- or trans-stilbene or stilbene hybrid compounds or other compound in the regulation of AP-1 that leads to a decrease in AP-1 activity. For example, indirect inhibition of AP-1 activity may occur as a result of an effect on AP-1 activating proteins such as mitogen-activated protein kinases (MAPK) or c-Fos-regulating kinase (FRK).

Topically or Transdermally-Administered Pharmaceutical Formulations

Topically or transdermally-administered pharmaceutical formulations of the invention are illustrated below. The illustrated formulations are exemplary and in no way limiting.

Topical drug delivery causes drug to be absorbed into tissue surrounding a site of administration, thereby exerting a therapeutic effect predominantly at that site.

Transdermal delivery has potential advantages over other routes of administration. It may reduce first-pass metabolism associated with oral delivery and is less painful than injections. However, the outermost layer of the skin, the stratum corneum, limits passive diffusion to small lipophilic molecules. Also, transdermal delivery can avoid first pass effects (hepatic metabolism), improve pharmacokinetic profile, reduce side effects and assist with patient compliance. To penetrate the stratum corneum barrier and facilitate transdermal drug delivery, passive systems and techniques (e.g. penetration enhancers and liposomes) and active systems and techniques (electroporation, iontophoresis, microneedles) have been used.

"Nanoemulsions/microemulsions" are thermodynamically stable transparent (translucent) isotropic dispersions of oil and water stabilized by an interfacial film of surfactant and cosurfactant molecules having the droplet size of less than 100 nm. See Shakeel, et al., "Transdermal and Topical Delivery of Anti-inflammatory Agents Using Nanoemulsion/Microemulsion: An Updated Review", *Current Nanoscience*, Volume 6, Number 2, April 2010, pp. 184-198(15). In certain embodiments of nanoemulsions of the invention, droplets have an average diameter of about 1,000 nm, 950 nm, 900 nm, 850 nm, 800 nm, 750 nm, 700 nm, 650 nm, 600 nm, 550 nm, 500 nm, 450 nm, 400 nm, 350 nm, 300 nm, 250 nm, 200 nm, 150 nm, 100 nm, 90 nm, 80 nm, 70 nm, 60 nm, 50 nm, 40 nm, 30 nm, 20 nm, 10 nm, or 9, 8, 7, 6, 5, 4, 3, 2 or 1 nm (most preferably about 50-75 nm).

Conventionally, a nanoemulsion is characterized by droplets or particles one thousand fold smaller than microemulsion droplets or particles.

As used herein, the term "nanoparticle" refers to any particle having a diameter of less than 1,000 nanometers (nm). In some embodiments, a nanoparticle has a diameter of less than 1,000 nm, 950 nm, 900 nm, 850 nm, 800 nm, 750 nm, 700 nm, 650 nm, 600 nm, 550 nm, 500 nm, 450 nm, 400 nm, 350 nm, 300 nm, 250 nm, 200 nm, 150 nm, 100 nm, 90 nm, 80 nm, 70 nm, 60 nm, 50 nm, 40 nm, 30 nm, 20 nm, 10 nm, or 9, 8, 7, 6, 5, 4, 3, 2 or 1 nm. Usually, a nanoparticle has a diameter of 300 nm or less, or 100 nm or less. Nanoparticles are the dispersed phase in a dispersion or emulsion.

Numerous lipids may be used to form a lipid bilayer on nanoparticles to provide transdermal liposomal formulations according to the present invention. Virtually any lipid which is used to form a liposome may be used in the lipid bilayer which surrounds the nanoparticles to form protocells according to an embodiment of the present invention. Preferred lipids for use in the present invention include, for example, 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-[phosphor-L-serine] (DOPS), 1,2-dioleoyl-3-trimethylammonium-propane (18:1 DOTAP), 1,2-dioleoyl-sn-glycero-3-phospho-(1'-rac-glycerol) (DOPG), 1,2-dioleoyl-sn-glycero-3-phosphoethanolamine (DOPE), 1,2-dipalmitoyl-sn-glycero-3-phosphoethanolamine (DPPE), 1,2-dioleoyl-sn-glycero-3-phosphoethanolamine-N-[methoxy(polyethylene glycol)-2000] (18:1 PEG-2000 PE), 1,2-dipalmitoyl-sn-glycero-3-phosphoethanolamine-N-[methoxy(polyethylene glycol)-2000] (16:0 PEG-2000 PE), 1-Oleoyl-2-[12-[(7-nitro-2-1,3-benzoxadiazol-4-yl)amino]lauroyl]-sn-Glycero-3-Phosphocholine (18:1-12:0 NBD PC), 1-palmitoyl-2-{12-[(7-nitro-2-1,3-benzoxadiazol-4-yl)amino]lauroyl}-sn-glycero-3-phosphocholine (16:0-12:0 NBD PC), cholesterol and mixtures/combinations thereof. Cholesterol, not technically a lipid, but presented as a lipid for purposes of an embodiment of the present invention given the fact that cholesterol may be an important component of the lipid bilayer of protocells according to an embodiment of the invention. Often cholesterol is incorporated into lipid bilayers of protocells in order to enhance structural integrity of the bilayer. These lipids are all readily available commercially from Avanti Polar Lipids, Inc. (Alabaster, Ala., USA). DOPE and DPPE are particularly useful for conjugating (through an appropriate crosslinker) peptides, polypeptides, including immunogenic peptides, proteins and antibodies, RNA and DNA through the amine group on the lipid.

The lipid bilayer can be PEGylated with a variety of polyethylene glycol-containing compositions. PEG molecules can have a variety of lengths and molecular weights and include, but are not limited to, PEG 200, PEG 1000, PEG 1500, PEG 4600, PEG 10,000, PEG-peptide conjugates or combinations thereof.

A wide variety of liposome formulation techniques are known to those of ordinary skill in the art and can be used in making topically or transdermally-administered liposomal formulations of the invention. These techniques include the microfluidic syntheses described and referenced in U.S. Patent Application Document No. 20140328898.

"Liposomes formed from nonphosphal lipid components which have the potential to form lipid bilayers are disclosed in Biochim. Biophys. Acta, 19: 227-232 (1982). For the preparation, purification, modification and loading of liposomes see generally, New, R.C.C., Liposomes: A Practical Approach, (1990) Oxford University Press Inc., N.Y. A general discussion of techniques for preparation of liposomes and of medication encapsulating liposomes can be found in U.S. Pat. No. 4,224,179 to Schneider. See also Mayer et al., Chemistry and Physics of Lipids, 40: 333-345 (1986). See also U.S. Pat. No. 6,083,529 to Manzo et al. for the encapsulation of an active agent dry powder composition. For incorporation of active agents into nanoparticles, see e.g., M. M. de Villiers et al. (editors), Nanotechnology in Drug Delivery, (2009) American Associate of Pharmaceutical Scientists, Springer: AAPS Press, New York, N.Y. For incorporation of active agents into micelles, see e.g., D. R. Lu and S. Oie, Cellular Drug Delivery: Principles and Practice, (2004) Humana Press Inc., Totowa, N.J." U.S. Patent No. 20140227174.

In certain embodiments, a transdermally-administered pharmaceutical composition of the invention comprises a transfersome, an elastic (deformable) vesicle, an ethosome, an invasome or a penetration-enhancer-containing vesicle. Representative formulations and syntheses for each of these delivery vehicles is described in Romero, et al., "Highly deformable and highly fluid vesicles as potential drug delivery systems: theoretical and practical considerations", *Intl. J. Nanomedicine,* 2013; 8:3171-86.

"Skin penetration enhancers" include, but are not limited to alkyl (N,N-disubstituted amino alkanoate)esters, such as dodecyl 2-(N,N-dimethylamino)propionate (DDAIP), a water-dispersible acid polymer, such as a polyacrylic acid polymer, a carbomer (e.g., Carbopol® or Carbopol 940P® (B. F. Goodrich Co. Akron, Ohio)), copolymers of polyacrylic acid (e.g., Pemulen® (B. F. Goodrich Co.) or Polycarbophil® (A. H. Robbins, Richmond, Va.); a polysaccharide gum (e.g. agar gum, alginate, carrageenan gum, ghatti gum, karaya gum, kadaya gum, rhamsan gum, xanthan gum, and galactomannan gum (e.g., guar gum, carob gum, and locust bean gum)), cellulose derivatives (e.g. ethyl cellulose, methyl, cellulose, hydroxypropyl cellulose), dimethyl sulfoxide (DMSO) and dimethyl acetamide (DMA), 2-pyrrolidone, N,N-diethyl-m-toluamide (DEET), 1-dodecylazacycloheptane-2-one (Azone® Nelson Research), N,N-dimethylformamide, N-methyl-2-pyrrolidone, calcium thioglycolate, dioxolanes, cyclic ketones, alkyl N,N-2-(disubstituted amino)alkanoates including tetradecyl (N,N-dimethylamino)acetate, dodecyl (N,N-dimethylamino)acetate, decyl (N,N-dimethylamino)acetate, octyl (N,N-dimethylamino) acetate, and dodecyl (N,N-diethylamino)acetate.

One group of preferred skin penetration enhancers includes isopropyl myristate, isopropyl palmitate, dimethyl sulfoxide, decyl methyl sulfoxide, dimethylalanine amide of a medium chain fatty acid, dodecyl 2-(N,N-dimethylamino) propionate and salts thereof (e.g., hydrochloric, hydrobromic, sulfuric, phosphoric, and nitric acid addition salts) and inorganic salts (e.g., acetic, benzoic, salicylic, glycolic, succinic, nicotinic, tartaric, maleic, malic, pamoic, methanesulfonic, cyclohexanesulfamic, picric, and lactic acid addition salts).

In some embodiments, the transdermally-administered pharmaceutical composition of the invention is administered by a patch which comprises an active-ingredient containing adhesive matrix disposed between an impermeable backing layer and a removable film layer. See e.g. U.S. Patent Application Document Nos. 20140322284 and 20140335150.

Representative Formulations

The topically or transdermally-administered pharmaceutical formulations of the invention can be administered in a wide variety of forms, including as an oil-in-water emulsion, microemulsion or nanoemulsion, a water-in-oil emulsion, microemulsion or nanoemulsion, a water-in-silicone emulsion, microemulsion or nanoemulsion, a liquid, a gel, an oil, a paste, a cream, a lotion, an ointment, a suspension, a foam, a spray or a serum carrier, a suspension, a liposome-containing formulation, a transfersome, an elastic (deformable) vesicle, an ethosome, an invasome or a penetration-enhancer-containing vesicle, a lacquer, or the formulations can comprise a component of a patch, bandage, or occlusive dressing, or other passive or active system for absorption through the skin or mucosal surface.

In certain embodiments, topically or transdermally-administered pharmaceutical formulations of the invention comprise one or more cis- or trans-stilbenes or a stilbene hybrids (or analogs, derivatives, pharmaceutically acceptable salts, enantiomers, stereoisomers, solvates, polymorphs and mixtures thereof), at least one ingredient selected from the group consisting of an antibiotic, a transdermal penetrating base (e.g. a transdermal penetrating base selected from the group consisting of cyclodextrins, one or more lipophilic carriers (including transdermal bases such as lipocore (e.g., Lipoderm®)) and mixtures thereof) and one or more emollients (e.g. isopropyl palmitate or isopropyl myristate and mixtures thereof). In some embodiments, these formulations comprise about 5 wt % to about 15 wt % of a transdermal penetrating base and about 1 wt % to about 10 wt % of one or more emollients. The formulations can further comprise about 0 wt % to about 15 wt % of one or more additional ingredients selected from the group consisting of a xanthan gum, an α-lipoic acid, melatonin, 3',3-diindolylmethane, N-methylpyrrolidone, vitamin D, quercetin, isoquercetin, vitamin $D_3$, vitamin E complex (including the related tocopherols and tocotrienols such as, without limitation, α-tocopherol, β-tocopherol, δ-tocopherol, γ-tocopherol, α-tocotrienol, β-tocotrienol, δ-tocotrienol, γ-tocotrienol, as well as derivatives and combinations thereof), ceteary alcohol, ceteareth-20, phenoxyethanol, caprylyl glycol, sorbic acid, polyacrylamide based emulsion, sweet orange essential oil or mixtures thereof.

In certain embodiments, topically or transdermally-administered pharmaceutical formulations of the invention comprise one or more cis- or trans-stilbenes or stilbene hybrids (or analogs, derivatives, pharmaceutically acceptable salts, enantiomers, stereoisomers, solvates, polymorphs and mixtures thereof) and at least one or more additional ingredients selected from the group consisting of:
(a) one or more surfactants (e.g. cetearyl alcohol, ceteareth-20 and mixtures thereof);
(b) one or more emulsification or rheology agents (e.g. poloxamer 407 NF, pluronic F-127 NF, block copolymer of ethylene oxide and propylene oxide, polyacrylamide emulsion (Sepigel® 305, Seppic, Inc., Fairfield, N.J.), and combinations thereof), xanthan gums and mixtures thereof);
(c) one or more antioxidants (e.g. α-lipoic acid, vitamin E (including tocopherols, tocotrienols, and derivatives and combinations thereof), vitamin D and vitamin D3 and mixtures thereof);
(d) one or more solvents (e.g. N-methylpyrrolidone);
(e) one or more preservatives (e.g. phenoxyethanol, caprylyl glycerol, sorbic acid and mixtures thereof);
(f) one or more fragrances and/or perfumants (e.g. one or more natural essential oils, such as sweet orange oil and mixtures thereof); and
(g) one or more buffers (e.g. tris(hydroxymethyl)aminomethane (Tris), citrate, 2-(N-morpholino)ethanesulfonic acid (MES), N,N-Bis(2-hydroxyethyl)-2-aminoethanesulfonic acid (BES), 1,3-bis(tris(hydroxymethyl)methylamino)propane (Bis-Tris), 4-(2-hydroxyethyl)-1-piperazine ethanesulfonic acid (HEPES), 3-(N-morpholino)propanesulfonic acid (MOPS), N,N-bis(2-hydroxyethyl)glycine (Bicine), N-[tris(hydroxymethyl)methyl]glycine (Tricine), N-2-acetamido-2-iminodiacetic acid (ADA), N-(2-Acetamido)-2-aminoethanesulfonic acid (ACES), piperazine-1,4-bis(2-ethanesulfonic acid) (PIPES), bicarbonate, phosphate and mixtures thereof). A representative buffer concentration is between about 1 μM to about 1 M.

In certain embodiments, topically or transdermally-administered pharmaceutical formulations of the invention comprise one or more cis- or trans-stilbenes (or analogs, derivatives, pharmaceutically acceptable salts, enantiomers, stereoisomers, solvates, polymorphs and mixtures thereof), one or more additional ingredients selected from the group consisting of one or more ingredients selected from the group consisting of melatonin, Carcinosin 30C, dimethylsulfoxide (DMSO), propylene glycol liquid, *Phytolacca americana* extract and mixtures thereof.

The compositions can also include a lipocore base cream (e.g. PCCA Lipoderm® transdermal base (PCCA USA, Houston, Tex.)) to enhance transdermal penetration of the cis- or trans-stilbenes or a stilbene hybrids.

In certain embodiments, topically or transdermally-administered pharmaceutical formulations of the invention are administered at a dosage of between about 1, 2, 3, 4, 5, 6, 7, 8, 9 or 10 cc per 1, 2, 3, 4, 5, 6, 7, 8, 9 or 10 $cm^2$ of administration site, e.g. approximately every 2, 4, 6, 8, 10, 12, 14, 16, 18, 20, 22 or 24 hours for a period of between about 1 to about 60 days.

In certain preferred embodiments, the topically or transdermally-administered pharmaceutical formulation is an oil-in-water emulsion comprising one or more cis- or trans-stilbenes or stilbene hybrids (or analogs, derivatives, pharmaceutically acceptable salts, enantiomers, stereoisomers, solvates, polymorphs and mixtures thereof), an oil phase comprising at least one oil, an aqueous phase comprising at least one surfactant, at least one organic solvent (co-surfactant) and water. The oil phase comprises, e.g. volatile or non-volatile oils selected from the group consisting of animal oils, vegetable oils, natural oils, synthetic oils, hydrocarbon oils, silicone oils, semi-synthetic derivatives thereof and mixtures thereof.

Preferably, the surfactant component of oil-in-water emulsions is an non-ionic surfactant selected from the group consisting of an ethoxylated surfactant, an alcohol ethoxylate, an alkyl phenol ethoxylate, a fatty acid ethoxylate, a monoalkaolamide ethoxylate, a sorbitan ester ethoxylate, a fatty amino ethoxylate, an ethylene oxide-propylene oxide copolymer, Bis(polyethylene glycol bis[imidazoyl carbonyl]), nonoxynol-9, Bis(polyethylene glycol bis[imidazoyl carbonyl]), Brij® 35, Brij® 56, Brij®72, Brij®76, Brij®92V, Brij®97, Brij®58P, Cremophor®EL, Decaethylene glycol monododecyl ether, N-Decanoyl-N-methylglucamine, n-Decyl alpha-D-glucopyranoside, Decyl beta-D-maltopyranoside, n-Dodecanoyl-N-methylglucamide, n-Dodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O—(N-heptylcarbamoyl)-alpha-D-glucopyranoside, Nonaethylene glycol monododecyl ether, N—N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-beta-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from Quillaja bark, Span®20, Span®40, Span®60, Span®65, Span®80, Span®85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tergitol, Tergitol, Type TMN-10, Tergitol, Type TMN-6, Tetradecyl-beta-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton®X-114, Triton®X-165, Triton®X-305, Triton®X-405, Triton®X-45, Triton®705-70, TWEEN®20, TWEEN®21, TWEEN®40, TWEEN®60, TWEEN®61, TWEEN®65, TWEEN®80, TWEEN® 81, TWEEN®85, Tyloxapol, n-Undecyl beta-D-glucopyranoside, a Poloxamer (including but not limited to Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 Benzoate, and Poloxamer 182 Dibenzoate) and derivatives thereof and mixtures thereof.

In one preferred embodiment of topically or transdermally-administered oil-in-water emulsions of the invention:
(a) the at least one oil is selected from the group consisting of mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, $C_{12-15}$ alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (*simmondsia chinensis* seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, eucalyptus leaf oil, lemon grass leaf oil, melaleuca leaf oil, oregano leaf oil, patchouli leaf oil, peppermint leaf oil, pine needle leaf oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, cassia Bark oil, cinnamon bark oil, sassafras Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol and derivatives and mixtures thereof; and
(b) the organic solvent (co-surfactant) is selected from the group consisting of a nonpolar solvent, a polar solvent, a protic solvent, an aprotic solvent and mixtures thereof.

In another preferred embodiment of topically or transdermally-administered oil-in-water emulsions of the invention, the organic solvent (co-surfactant) is selected from the group consisting of a $C_1$-$C_{12}$ alcohol, diol, triol, dialkyl phosphate, tri-alkyl phosphate (e.g. tri-n-butyl phosphate), or a derivative or mixture thereof.

In one preferred embodiment of topically or transdermally-administered emulsions of the invention, the organic solvent (co-surfactant) is selected from the group consisting of ethanol, methanol, isopropyl alcohol, glycerol, medium chain triglycerides, diethyl ether, ethyl acetate, acetone, dimethyl sulfoxide (DMSO), acetic acid, n-butanol, butylene glycol, perfumers alcohols, isopropanol, n-propanol, formic acid, propylene glycols, glycerol, sorbitol, industrial methylated spirit, triacetin, hexane, benzene, toluene, diethyl ether, chloroform, 1,4-dixoane, tetrahydrofuran, dichloromethane, acetone, acetonitrile, dimethylformamide, dimethyl sulfoxide, formic acid and derivatives and mixtures thereof.

In another preferred embodiment of topically or transdermally-administered oil-in-water emulsions of the invention, the organic solvent (co-surfactant) is selected from the group consisting of ethanol, i-propanol, 1,2-propanediol and n-butanol and mixtures thereof.

In still another preferred embodiment of topically or transdermally-administered oil-in-water emulsions of the invention:
(a) the oil phase comprises one or more compositions selected from the group consisting of dimethicone, cyclomethicone, isopropyl palmitate, isopropyl myristate, cetostearyl alcohol, cetyl alcohol, stearyl alcohol, stearic acid, palmitostearic acid, a self-emulsifiable wax and mixtures thereof;
(b) the surfactant comprises one or more compositions selected from the group consisting of glyceryl/PEG100 stearate, sorbitan monostearate, sorbitan palmitate, Steareth-20, Steareth-2, Steareth-21 and Ceteareth-20 and mixtures thereof; and
(c) the emulsion optionally comprises one or more additional compositions selected from the group consisting of propylene glycol, oleyl alcohol, phenoxyethanol and glyceryl triacetate; one or more gelling agents selected from the group consisting of carbomers, cellulose gelling agents, xanthan gums, aluminum magnesium silicates but excluding aluminum magnesium silicate/titanium dioxide/silica, guar gums, polyacrylamides, modified starches and mixtures thereof.

Preferably, the topically or transdermally-administered oil-in-water emulsion comprises one or more antibiotics.

In certain preferred embodiments, the topically or transdermally-administered oil-in-water emulsion is a nanoemulsion wherein the one or more cis- or trans-stilbenes or stilbene hybrids (or analogs, derivatives, pharmaceutically acceptable salts, enantiomers, stereoisomers, solvates, polymorphs and mixtures thereof), the oil phase comprising at least one oil, the aqueous phase comprising at least one surfactant, the at least one organic solvent (co-surfactant) and water form droplets having an average diameter of about 1,000 nm, 950 nm, 900 nm, 850 nm, 800 nm, 750 nm, 700 nm, 650 nm, 600 nm, 550 nm, 500 nm, 450 nm, 400 nm, 350 nm, 300 nm, 250 nm, 200 nm, 150 nm, 100 nm, 90 nm, 80 nm, 70 nm, 60 nm, 50 nm, 40 nm, 30 nm, 20 nm, 10 nm, or 9, 8, 7, 6, 5, 4, 3, 2 or 1 nm (most preferably about 50-75 nm).

In preferred oil-in-water nanoemulsions of the invention, the surfactant is a non-ionic surfactant selected from the group consisting of EL-40 and Tween-80, the organic solvent (co-surfactant) is selected from the group consisting of ethanol, i-propanol, 1,2-propanediol and n-butanol and mixtures thereof, the oil is isopropyl myristate (IPM), the droplets have an average diameter of about 50-75 nm, the nanoemulsion comprises one or more antibiotics selected from the group consisting of bacitracin, neomycin, mupirocin, polymyxin B, chlorhexidine digluconate and mixtures thereof and the cis- or trans-stilbene is a compound selected from the group consisting of:

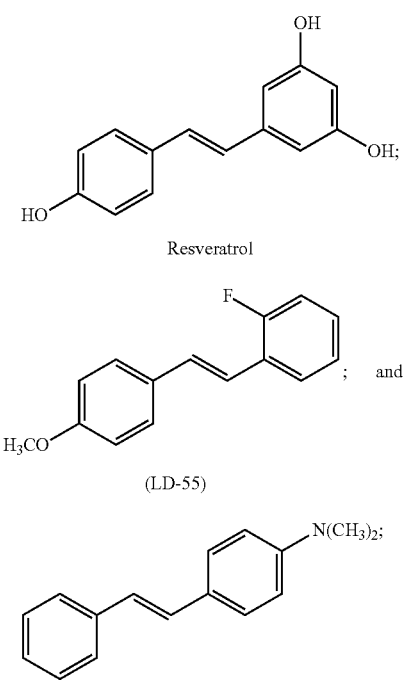

and analogs, derivatives, pharmaceutically acceptable salts, enantiomers, stereoisomers, solvates, polymorphs and mixtures thereof.

In preferred oil-in-water emulsions or nanoemulsions of the invention, the emulsion or nanoemulsion comprises about 1% wt of the cis- or trans-stilbene or a stilbene hybrid and about 2% wt of an antibiotic (e.g. chlorhexidine digluconate).

In a particularly preferred nanoemulsion of the invention:
(a) the surfactant is a non-ionic surfactant selected from the group consisting of EL-40 and Tween-80;
(b) the organic solvent (co-surfactant) is selected from the group consisting of ethanol, i-propanol, 1,2-propanediol and n-butanol and mixtures thereof; and
(c) the oil is isopropyl myristate (IPM).

Transdermally-administered pharmaceutical formulations can comprise a population of stratum corneum-penetrating liposome encapsulated nanoparticles. The nanoparticulates comprise one or more more cis- or trans-stilbenes or a stilbene hybrid or analogs, derivatives, pharmaceutically acceptable salts, enantiomers, stereoisomers, solvates, polymorphs and mixtures thereof, and preferably have an average diameter of about 50 nm, 40 nm, 30 nm, 20 nm, 10 nm, or 9, 8, 7, 6, 5, 4, 3, 2 or 1 nm.

Chemistry

Trans-stilbenes

The synthesis of a library of 75 (E)-stilbenes was accomplished as shown in Schemes 1, 2 and 3. Initially our strategy for the construction of the trans-stilbene skeleton involved the reaction of an aromatic phosphonium ylide with substituted benzaldehydes.[31] This method proved to be unsatisfactory due to the formation of a mixture of E and Z isomers and the formation of triphenylphosphine oxide, which complicates the purification process. It is known that semi-stabilized ylides such as benzyl ylides give mixtures of isomers, which can be converted to E isomers by heating with a catalytic amount of iodine in heptane or toluene. In order to avoid these problems, Horner-Emmons-Wadsworth olefination chemistry was utilized as described by Lion et al.[32] Reaction of benzylphosphonic acid diethyl ester (2) with substituted benzaldehydes (3a-3k, 3m-3p, 3r, 3u-3dd, 3ff, 3gg) or methoxymethyl (MOM) hydroxyl substituted benzaldehydes (3hh-3ll) in DMF using sodium methoxide as the base in the presence of 18-crown-6 at 120° C. afforded 33 substituted stilbenes or methoxymethyl hydroxystilbenes (4) exclusively in the (E)-conformation (Scheme 1). There was no detectable Z isomer by $^1$H NMR analysis. The diethylphosphoric acid byproduct is water soluble and was easily removed. In the case of the MOM protected benzaldehydes, (4hh-4ll), which were stable under the Horner-Emmons-Wadsworth conditions, the methoxymethyl protecting group was readily removed in a second step using hydrochloric acid to give the phenolic stilbene.

Scheme 1

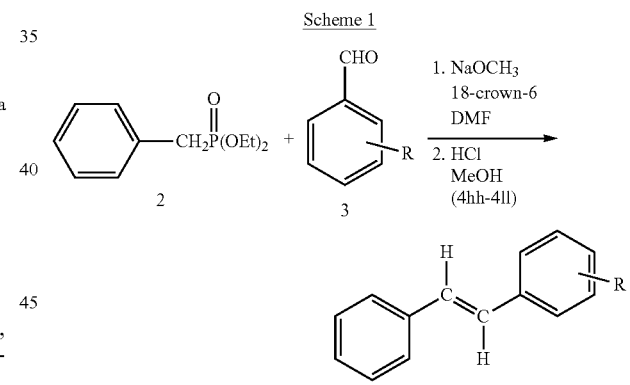

| a: R = 3,4-OCH$_3$ | n: R = 3-F | aa: R = 2,4,6-CH$_3$ |
| b: R = 4-OCH$_3$ | o: R = 2,3-OCH$_3$ | bb: R = 2-OCH$_3$ |
| c: R = 4-Cl | p: R = 2-F | cc: R = 4-N(CH$_3$)$_2$ |
| d: R = 4-CH$_3$ | q: R = 3-OCH$_3$, 4-OH | dd: R = 2,6-Cl |
| e: R = 4-CN | r: R = 3-OCH$_3$ | ee: R = 3,4-OH |
| f: R = 3,5-OCH$_3$ | s: R = 3-OH, 4-OCH$_3$ | ff: R = 3,4,5-OCH$_3$ |
| g: R = 2,6-OCH$_3$ | t: R = 3-OH | gg: R = 2,3,4-OCH$_3$ |
| h: R = 3-Cl | u: R = 2,4-OCH$_3$ | hh: R = 4-OCH$_2$OCH$_3$ |
| i: R = 3-CH$_3$ | v: R = 2-CH$_3$ | ii: R = 3-OCH$_3$, 4-CH$_2$OCH$_3$ |
| j: R = 2-Cl | w: R = 3-CF$_3$ | jj: R = 3-OCH$_2$OCH$_3$, 4-CH$_3$ |
| k: R = 4-OCH$_2$CH$_3$ | x: R = 4-CF$_3$ | kk: R = 3-OCH$_2$OCH$_3$ |
| l: R = 4-OH | y: R = 2,5-OCH$_3$ | ll: R = 3,4-OCH$_2$OCH$_3$ |
| m: R = 4-F | z: R = 2-CF$_3$ | |

Reaction of p-methoxybenzylphosphonic acid diethyl ester (5) with the appropriately substituted benzaldehydes (3a-3w, 3y-3bb, 3dd, 3ee) or methoxymethyl hydroxyl substituted benzaldehydes (3ff, 3gg) under the same Horner-Emmons- Wadsworth conditions afforded 31 trans-stilbenes (6) having one anisole ring as shown in Scheme 2. The methoxymethyl protecting group on compounds 6ff and 6gg was readily removed using hydrochloric acid to give 6x and 6cc.

Scheme 2

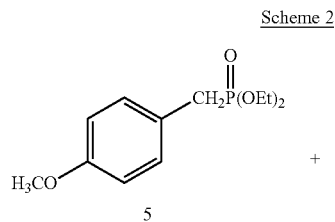

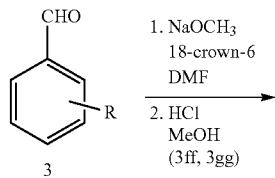

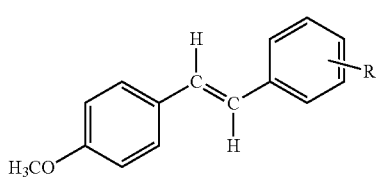

| | | |
|---|---|---|
| a: R = 3,4-OCH$_3$ | l: R = 3,4,5-OCH$_3$ | w: R = 3-Br |
| b: R = 4-OCH$_3$ | m: R = 4-F | x: R = 3,4-OH |
| c: R = 4-Cl | n: R = 3-F | y: R = 2,5-OCH$_3$ |
| d: R = 4-CH$_3$ | o: R = 2,3-OCH$_3$ | z: R = 2-CF$_3$ |
| e: R = 4-CN | p: R = 2-F | aa: R = 2,4,6-CH$_3$ |
| f: R = 3,5-OCH$_3$ | q: R = 2,4,5-OCH$_3$ | bb: R = 2-OCH$_3$ |
| g: R = 2,6-OCH$_3$ | r: R = 3-OCH$_3$ | cc: R = 2,3-OH |
| h: R = 3-Cl | s: R = 2,3,4-OCH$_3$ | dd: R = 4-N(CH$_3$)$_2$ |
| i: R = 3-CH$_3$ | t: R = 4-Br | ee: R = 2,6-Cl |
| j: R = 2-Cl | u: R = 2,4-OCH$_3$ | ff: R = 3,4-OCH$_2$OCH$_3$ |
| k: R = 4-OCH$_2$CH$_3$ | v: R = 2-CH$_2$CH$_3$, 3,4-OCH$_3$ | gg: R = 2,3-OCH$_2$OCH$_3$ |

Scheme 3, below, shows the reaction of benzyl- or p-methoxybenzyl-phosphonic acid diethyl esters (2 or 5) with pyridyl, thienyl and naphthyl aldehydes (7) under Horner-Emmons-Wadsworth conditions to afford 10 pyridyl, thienyl and naphthyl trans-stilbenes (8).

Scheme 3

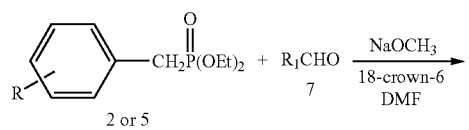

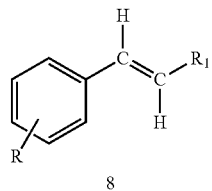

| | |
|---|---|
| a: R = H, R$_1$ = 3-C$_5$H$_4$N | f: R = H, R$_1$ = 1-C$_{10}$H$_7$ |
| b: R = H, R$_1$ = 4-C$_5$H$_4$N | g: R = OCH$_3$, R$_1$ = 2-C$_{10}$H$_7$ |
| c: R = H, R$_1$ = 2-C$_5$H$_4$N | h: R = OCH$_3$, R$_1$ = 1-C$_{10}$H$_7$ |
| d: R = H, R$_1$ = 2-C$_4$H$_3$S | i: R = OCH$_3$, R$_1$ = 2-C$_4$H$_3$S |
| e: R = H, R$_1$ = 2-C$_{10}$H$_7$ | j: R = OCH$_3$, R$_1$ = 2-C$_5$H$_4$N |

Cis-Stilbenes

The strategy used toward the synthesis of Z-stilbenes makes use of the classic Wittig olefination chemistry as described by Bellucci et al[1]. The methodology possesses the key advantage of stereoselectivity using the appropriate conditions. The ratio of the Z:E isomer was found to increase with decreasing temperature and the nature of the counterion of the phosphonium salt. Benzyltriphenylphosphonium iodides reacted with benzldehydes bearing both electron withdrawing and electron donating substituents to produce practically pure Z isomers. Reaction of the appropriately substituted phosphonium iodide salt (1) with substituted benzaldehydes (2) in dichloromethane using potassium hydroxide as the base in the presence of 18-crown-6 at −70° C. afforded substituted stilbenes (3) almost exclusively in the (Z)-conformation. Since the R$_1$ substituent on the phosphonium iodide salt and the R$_2$ substituent on the benzaldehyde can be many different groups, the number of different products (3) that can be formed is enormous.

Scheme 4

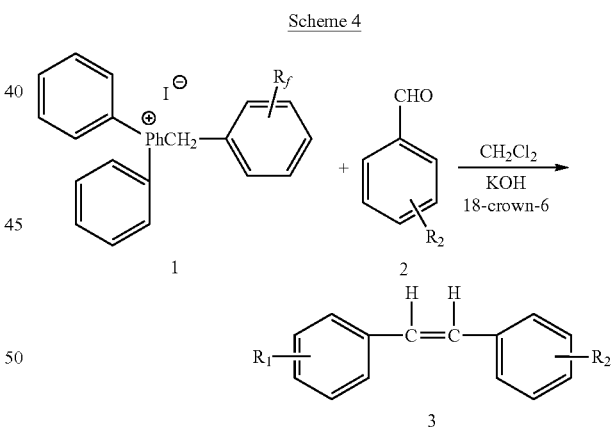

Using the above-synthetic method by analogy, a wide variety of cis-stilbenes may be synthesized by analogy with the synthesis of the trans-stilbenes, described above. These compounds were tested and the results are presented in FIG. 13.

Hybrid stilbenes are synthesized utilizing synthetic methods and steps well known in the art, including as described in U.S. Pat. No. 8,841,326 of Sep. 23, 2014.

Results

Figure 1:
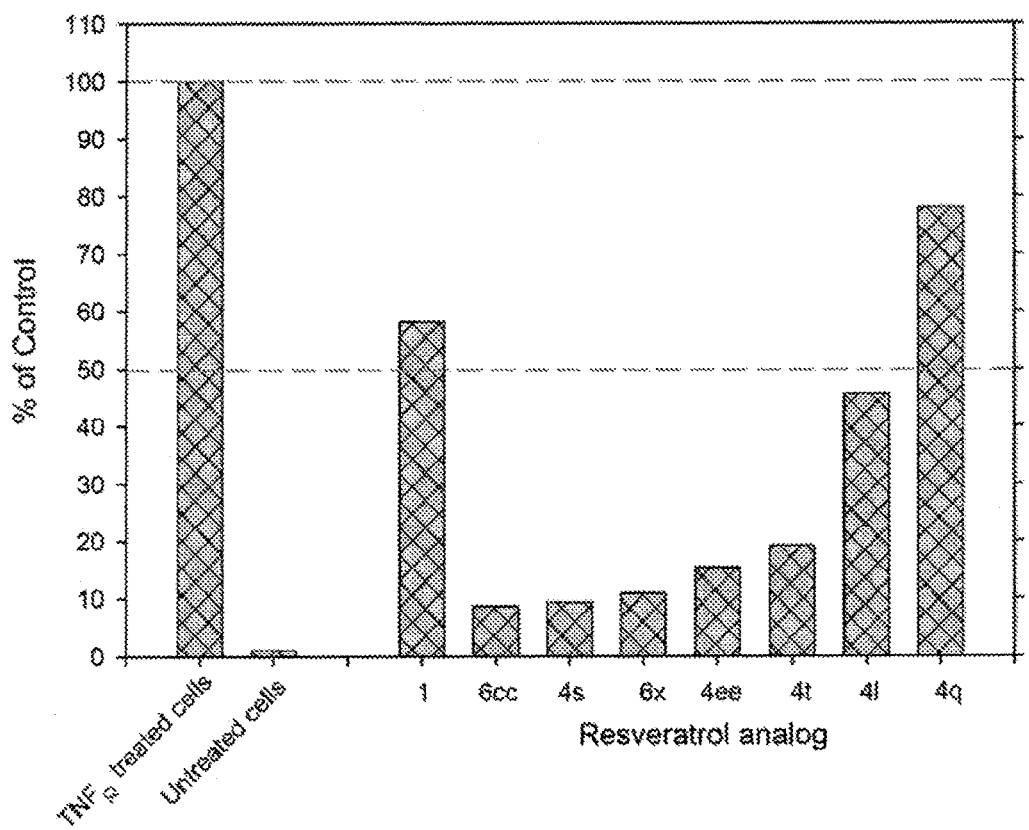
FIG. 1 shows the inhibition of the TNFα-induced activation of NF-κB by resveratrol (1) and analogs of resveratrol (Scheme 1). All of the resveratrol analogs retained anti-oxidant activity.

The first group of resveratrol analogs (FIG. 1) retain hydroxy functional groups on one or both of the aromatic rings. Resveratrol and 7 analogs were screened at 15 µM concentration. All of the analogs in this series retained anti-oxidant activity in the TRAP or FRAP assay. The total radical-trapping anti-oxidant parameter assay (TRAP assay) measures the ability of an analog to react with the preformed radical monocation of 2,2'-azinobis-(3-ethylbenzothiazoline-6-sulfonic acid) (ABTS.$^+$). The ferric reducing/ anti-oxidant power assay (FRAP assay) measures the ability of an analog to reduce a ferric tripyridyltriazine complex. Analogs 6cc and 6x were selected for further study. Analogs that also contained a methoxy functional group were the most active analogs in this series. Therefore, a separate series of substituted trans-stilbenes was synthesized that contained only methoxy groups.

Figure 2:
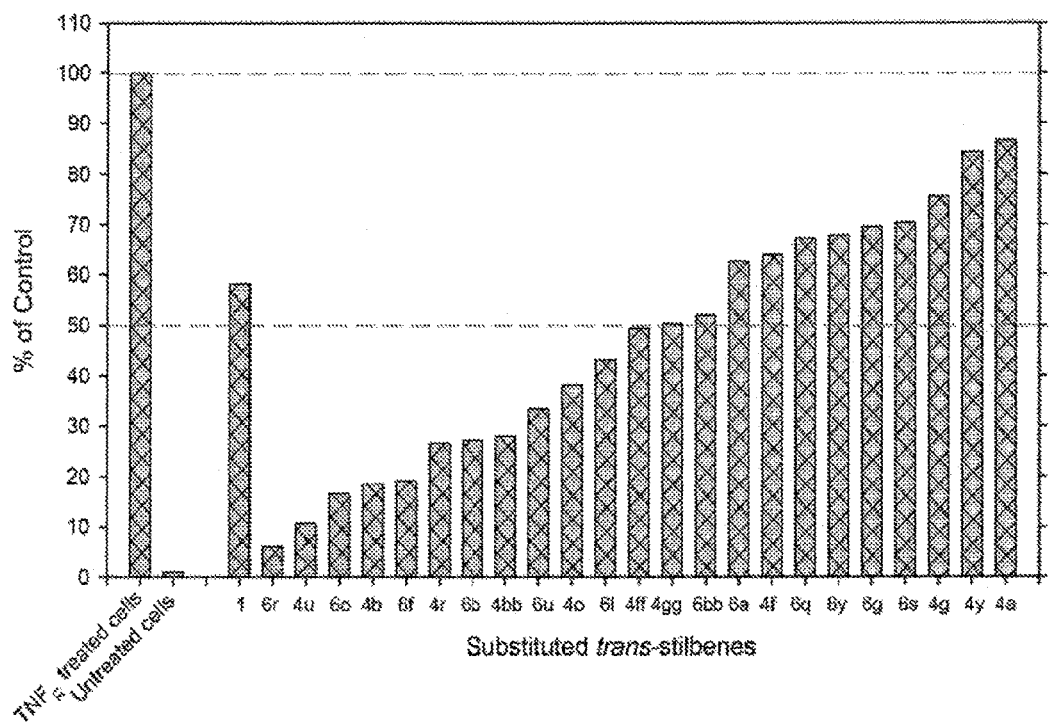
FIG. 2 shows the inhibition of the TNFα-induced activation of NF-κB by substituted trans-stilbenes containing only methoxy substituents (Schemes 1 and 2).

Twenty three stilbenes in the methoxy substituted series were screened and compared to resveratrol (FIG. 2). Fourteen of the 23 are more active than resveratrol as inhibitors of TNFα-induced activation of NFκB. Stilbene 6r was selected for additional study. None of the stilbenes in FIG. 2 retained anti-oxidant activity. Clearly, anti-oxidant activity is not essential for the ability of these compounds to prevent the TNFα-induced activation of NF-κB.

Figure 3:
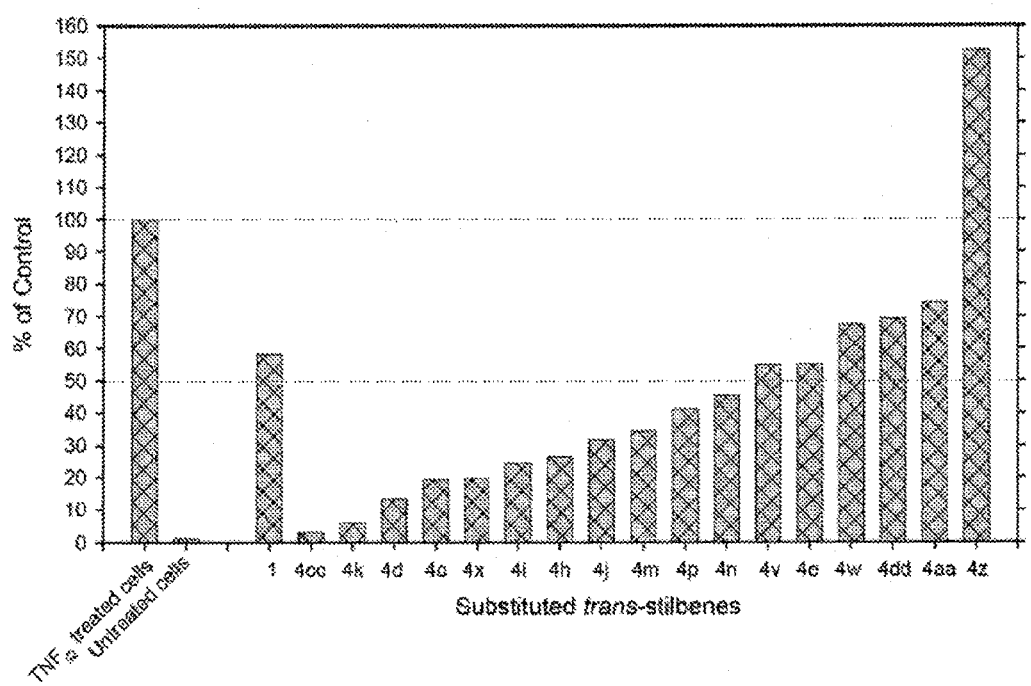
FIG. 3 shows the inhibition of the TNFα-induced activation of NF-κB by substituted trans-stilbenes devoid of phenolic or methoxy groups.

Seventeen substituted trans-stilbenes were synthesized that contained a variety of substituents other than hydroxy or methoxy groups on one of the rings and no substituent on the other ring. Thirteen of these were more active than resveratrol as inhibitors of TNFα-induced activation of NFκB in the preliminary screen (FIG. 3). Stilbenes 4cc and 4k were selected for further study. Only 4cc retained anti-oxidant activity.

Seventeen substituted trans-stilbenes were synthesized that contained a variety of functional groups on one ring, excluding hydroxy groups, and having a methoxy group on the other ring (FIG. 4). Fifteen of these compounds are more active than resveratrol. Stilbenes 6p, 6h, 6n, 6j, 6i and 6d were selected for further study.

Figure 5:
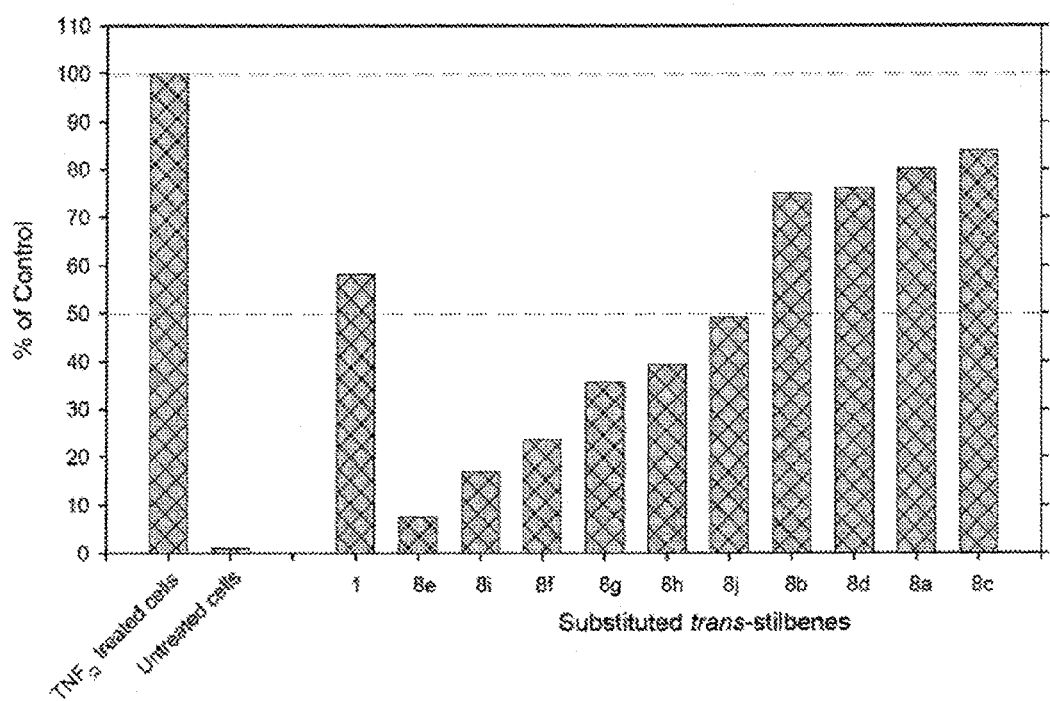
FIG. 5 shows the inhibition of the TNFα-induced activation of NF-κB by analogs of trans-stilbenes (Scheme 3).

Ten compounds were synthesized that contain one ring that is either a heterocyclic ring or a naphthalene ring (FIG. 5). These compounds are only remotely related to resveratrol. Four of these compounds have a methoxy group on one ring, and a number of these compounds are more active than resveratrol. Stilbene 8e was selected for further study.

Resveratrol and the 12 substituted trans-stilbenes that were selected for determination of $IC_{50}$ values were analyzed in triplicate. $IC_{50}$ values along with anti-oxidant activity and calculated ClogP values are summarized in Table 1. Several points are noteworthy. Some of the trans-stilbenes, such as compounds 4cc (compound 2a) and 6p (LD-55, compound 1a), are more than 100-fold more potent than resveratrol. Modest changes in the nature of the ring substituent or its location can markedly affect activity. Most of the compounds in Table 1 do not retain anti-oxidant activity. The toxicities of the 75 compounds evaluated in this study were determined. The initial screening that was carried out at 15 μM concentrations of resveratrol or substituted trans-stilbenes involved exposure of the cells to TNFα and to inhibitor for 7 hours. There was no apparent change in cell morphology. As a follow-up, the compounds in Table 1 were analyzed further by determination of cell viability, again after 7 hours and with exposure to 15 μM concentrations. In all cases, there was no loss in cell viability compared to untreated controls.

TABLE 1

$IC_{50}$ values of resveratrol and substituted trans-stilbenes for inhibition of the TNFα-induced activation of NFκB.

| Number | Structure | $IC_{50}$ (μM) | Anti-oxidant Activity | | CLogP |
| --- | --- | --- | --- | --- | --- |
| | | | TRAP | FRAP | |
| 1 resveratrol | 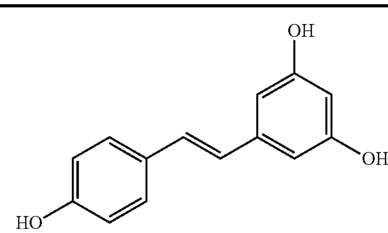 | 20 ± 3 | + | + | 2.833 |
| 6cc | 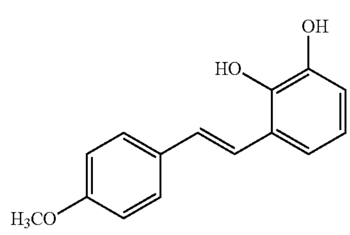 [SMILES: COc1ccc(/C=C/c2cccc(O)c2O)cc1] | 0.5 ± 0.3 | + | + | 3.089 |
| 6x | 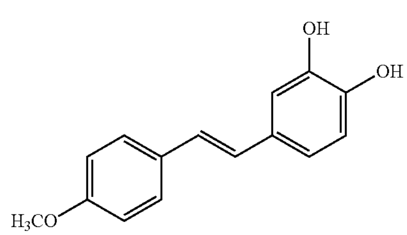 [SMILES: COc1ccc(/C=C/c2ccc(O)c(O)c2)cc1] | 0.6 ± 0.4 | + | + | 3.089 |

TABLE 1-continued

IC$_{50}$ values of resveratrol and substituted trans-stilbenes for inhibition of the TNFα-induced activation of NFκB.

| Number | Structure | IC$_{50}$ (μM) | Anti-oxidant Activity | | CLogP |
| --- | --- | --- | --- | --- | --- |
| | | | TRAP | FRAP | |
| 6r | 4-MeO-C$_6$H$_4$-CH=CH-C$_6$H$_4$-3-OCH$_3$ | 0.6 ± 0.1 | − | − | 4.272 |
| 4cc | C$_6$H$_5$-CH=CH-C$_6$H$_4$-4-N(CH$_3$)$_2$ | 0.15 ± 0.1 | + | + | 4.599 |
| 4k | C$_6$H$_5$-CH=CH-C$_6$H$_4$-4-OCH$_2$CH$_3$ | 0.3 ± 0.03 | − | − | 4.882 |
| 6p | 4-MeO-C$_6$H$_4$-CH=CH-C$_6$H$_4$-2-F | 0.15 ± 0.1 | − | − | 4.496 |
| 6h | 4-MeO-C$_6$H$_4$-CH=CH-C$_6$H$_4$-3-Cl | 1.0 ± 0.1 | − | − | 5.066 |
| 6n | 4-MeO-C$_6$H$_4$-CH=CH-C$_6$H$_4$-3-F | 1.1 ± 0.6 | − | − | 4.496 |
| 6j | 4-MeO-C$_6$H$_4$-CH=CH-C$_6$H$_4$-2-Cl | 1.5 ± 0.03 | − | − | 5.066 |

TABLE 1-continued

IC$_{50}$ values of resveratrol and substituted trans-stilbenes for inhibition of the TNFα-induced activation of NFκB.

| Number | Structure | IC$_{50}$ (μM) | Anti-oxidant Activity | | CLogP |
| --- | --- | --- | --- | --- | --- |
| | | | TRAP | FRAP | |
| 6i | 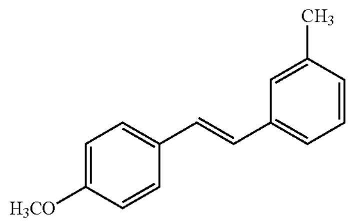 [SMILES: COc1ccc(/C=C/c2cccc(Cl)c2)cc1] | 0.8 ± 0.2 | – | – | 4.852 |
| 6d | 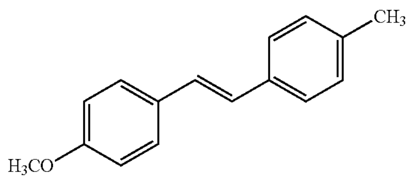 [SMILES: COc1ccc(/C=C/c2ccc(C)cc2)cc1] | 0.9 ± 0.1 | – | – | 4.852 |
| 8e | 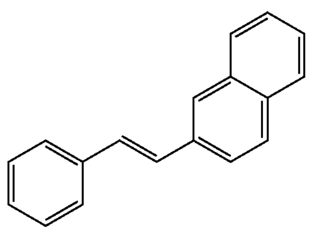 [SMILES: C(=C\c1ccc2ccccc2c1)/c1ccccc1] | 1.3 ± 0.3 | – | – | 5.608 |

Figure 6:
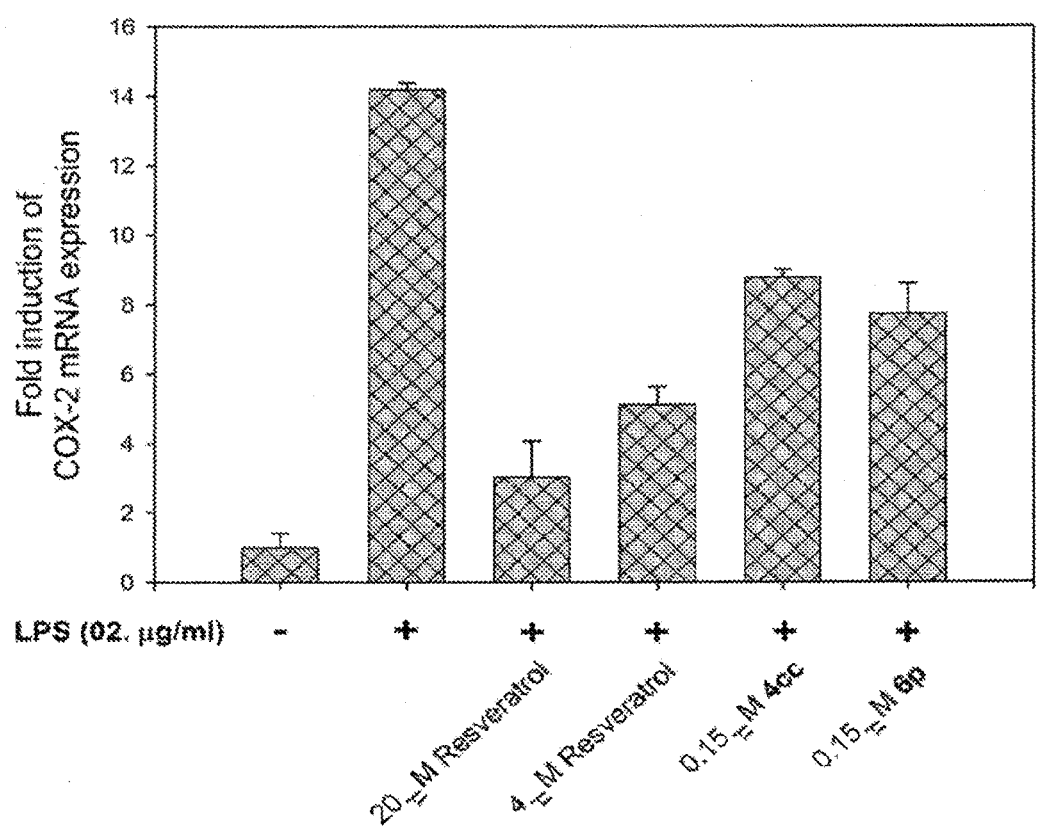
FIG. 6 shows the inhibitory effects in micromoles (μM) of resveratrol and analogs 4cc and 6p on LPS-induced expression of COX-2 mRNA in BV-2 microglial cells. Error bars represent standard deviations, n=3.
Figure 7:
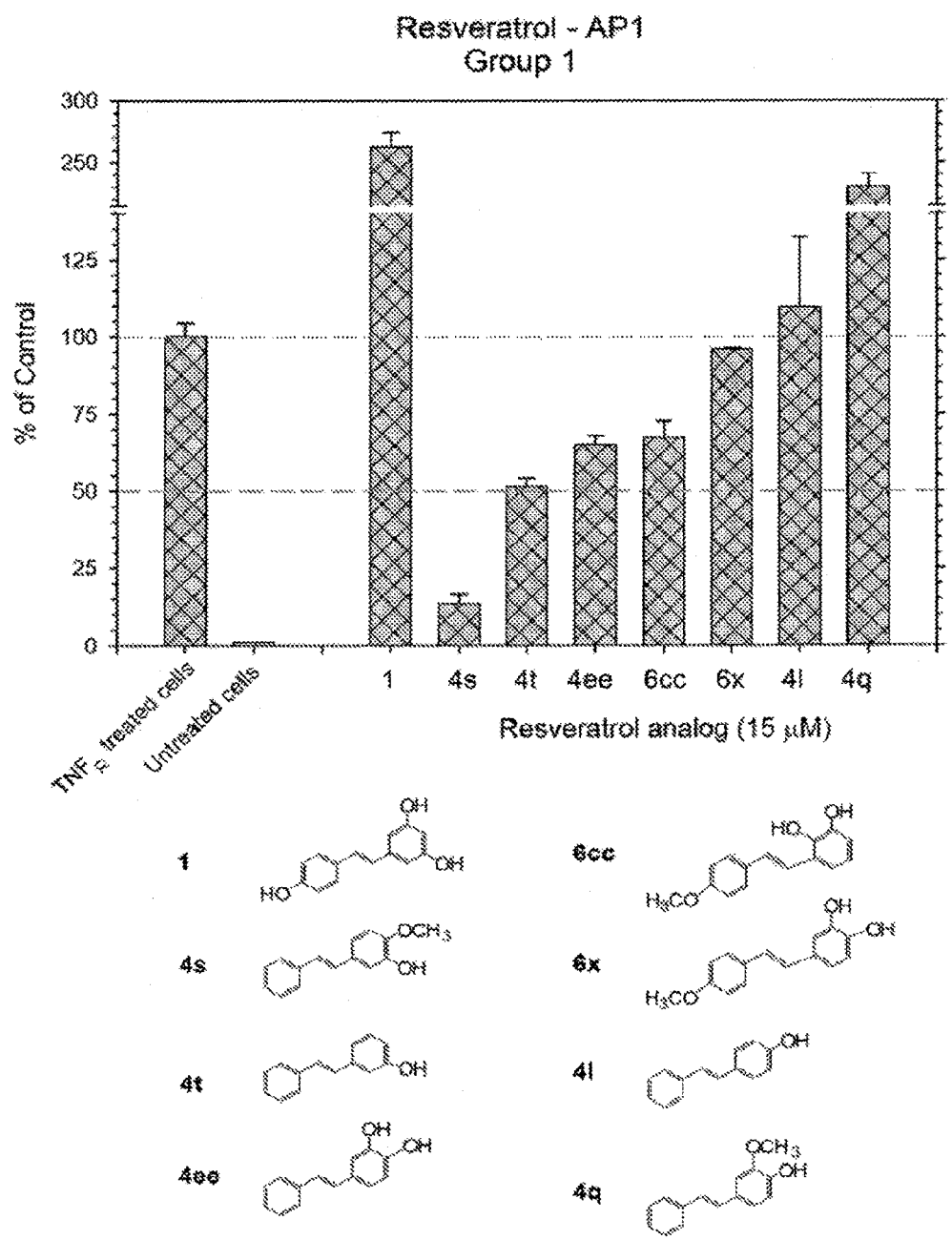
Figure 8:
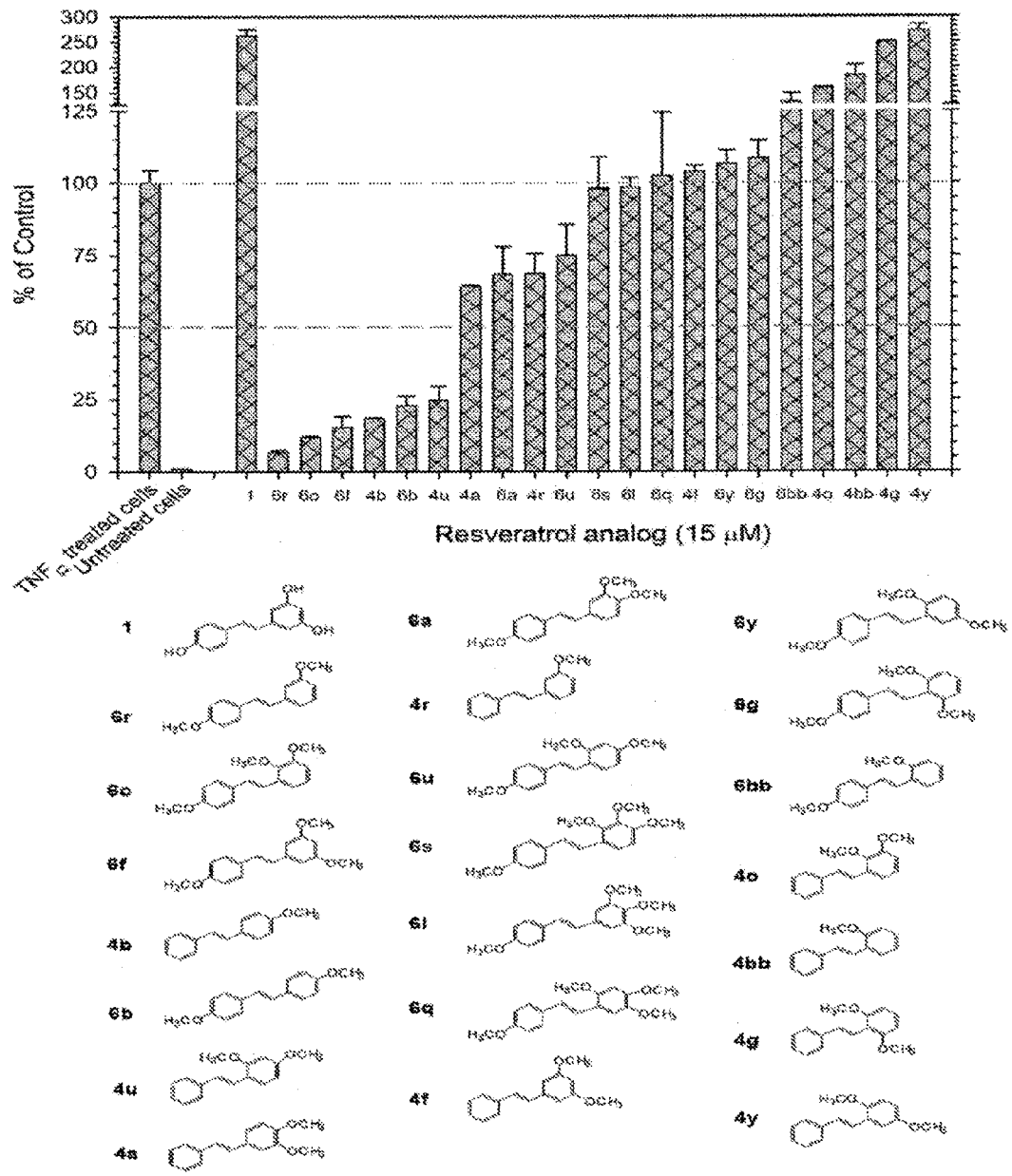
Figure 12:
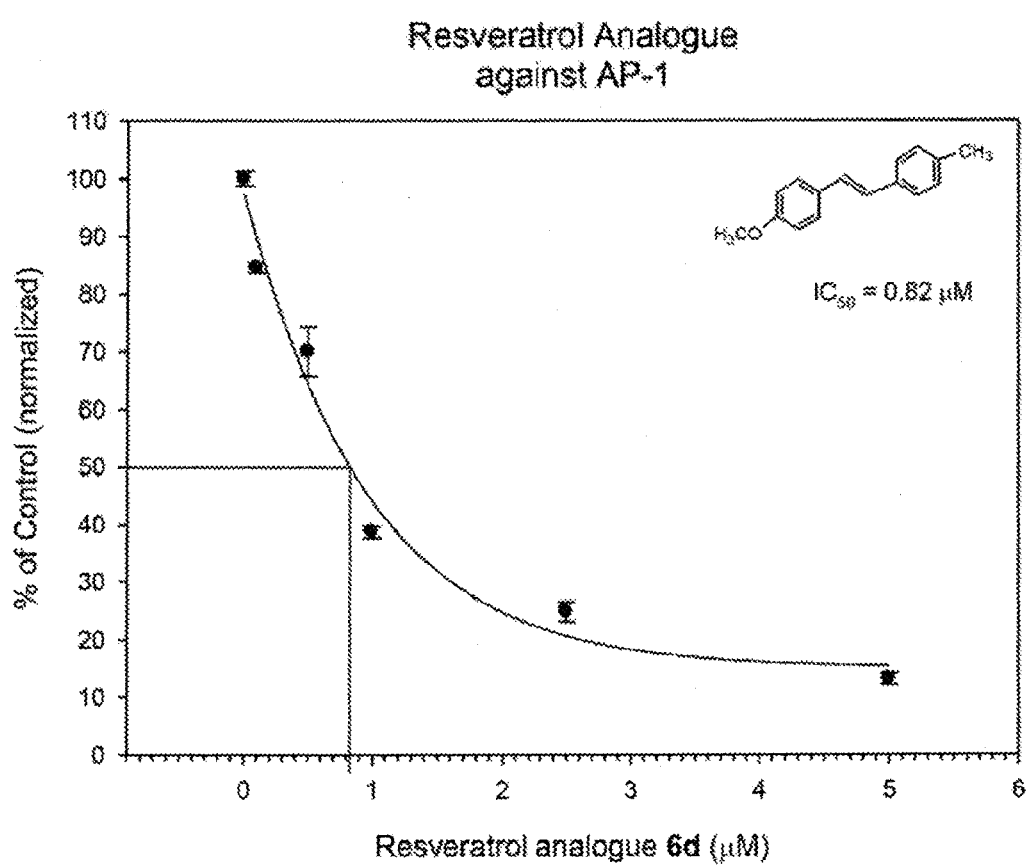

To determine whether the effects of resveratrol and its analogs in inhibiting the activation of NF-κB extend beyond the cell line used for screening, resveratrol and analogs 4cc (compound 2a) and 6p (LD-55, compound 1a) were compared using microglial BV-2 cells. This cell line has been shown to express COX-2 in response to LPS stimulation by an NF-κB-dependent pathway.[33] BV-2 cells stimulated with LPS showed a strong induction of COX-2 mRNA (FIG. 6) that was markedly suppressed by 20 μM resveratrol and about 50% inhibited by 4 μM resveratrol. Analog 4cc (2a) and analog 6p (LD-55, 1a) at 0.15 μM concentrations were almost as effective as 4 μM resveratrol, consistent with the conclusions from Table 1 that these two analogs are more potent than resveratrol.

Resveratrol is one of several polyhydroxylated stilbene natural products with biological activity. Piceatannol (9) (figure below), which is present in the seeds of *Euphorbia lagascae*, is similar to resveratrol except for the presence of an additional hydroxyl functional group. Piceatannol exhibits anti-inflammatory and anti-proliferative activities[17] and induces apoptosis in lymphoma cells.[34] Piceatannol, like resveratrol, also inhibits TNF-induced activation of NF-κB whereas stilbene itself is inactive.[35] Pterostilbene (10) and 3'-hydroxypterostilbene (11) (figure below) are natural analogs of resveratrol and piceatannol, respectively, that exhibit chemopreventive and apoptosis-inducing activities.[36,37] These two analogs as well as resveratrol itself show markedly different apoptosis-inducing activities against sensitive and resistant leukemia cells,[37] suggesting that minor structural changes in these hydroxylated stilbenes have major effects on biological activity.[21] However, all of these natural products retain one or more phenolic groups, which have been generally assumed to contribute both to anti-oxidant and to biological activities.

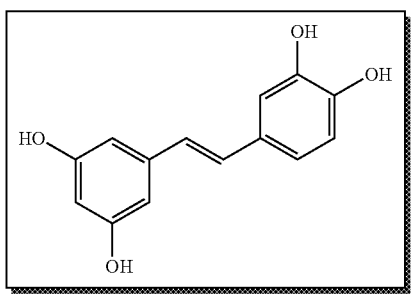

9

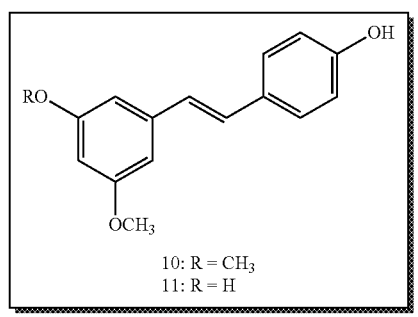

10: R = CH$_3$
11: R = H

The trans-stilbenes in FIG. 14 and elsewhere are analogs of resveratrol and related natural products. All of these analogs of resveratrol contain one or more hydroxy groups, and some of these analogs also contain methoxy groups. It is not surprising that this group of resveratrol analogs retains activity, in view of the reported activities for resveratrol, piceatannol and related compounds.[21,35-37] The activities of the analogs in FIG. 1 as inhibitors of the TNFα-induced activation of NF-κB, however, vary considerably; some compounds, such as analogs 6cc, 4s and 6x, are considerably more active than resveratrol. These three analogs contain one or two hydroxy groups and a single methoxy group. Therefore, it was of interest to evaluate trans-stilbenes that were devoid of hydroxy groups and would not be expected to exhibit anti-oxidant activity and to determine whether these compounds were still effective as inhibitors of the activation of NF-κB.

The 23 trans-stilbenes in FIG. 2 contain one or more methoxy groups and include compounds with methoxy groups on both of the aromatic rings. None of these methoxy-substituted trans-stilbenes retained anti-oxidant activity in either the TRAP assay or the FRAP assay. Nevertheless, many of these compounds are more active than resveratrol as inhibitors of the TNFα-induced activation of NF-κB. This includes trans-stilbenes 6r, 4u, 6o, 4b and 6f that are especially active and contain one to three methoxy groups, either on one or on both rings and in different positions. Other compounds in this group, such as 6b and 4o, are isomers of 6r but retained very little activity whereas 6r is highly active.

Some of the most active trans-stilbenes contain substituents other than hydroxy or methoxy groups (FIGS. 3 and 4) and include compounds with substituents on one or both rings. trans-Stilbene 4cc (compound 2a) with a dimethylamino substituent in the 4-position and trans-stilbene 6p (LD-55, compound 1a) with 2-fluoro- and 4'-methoxy substituents were the most active of the 75 compounds included in this study; both 4cc (compound 2a) and 6p (LD-55, compound 1a) showed $IC_{50}$ values of 0.15 µM, which is >100-fold more potent than resveratrol. Compound 4cc (2a) exhibits anti-oxidant activity in both the FRAP and TRAP assays, whereas compound 6p (LD-55, 1a) does not exhibit anti-oxidant activity.

The actual target(s) whereby the most active substituted trans-stilbenes (Table 1) inhibit the TNFα-induced activation of NF-κB remains to be identified. Resveratrol has been shown to suppress the TNF-induced phosphorylation and nuclear translocation of the p65 subunit of NF-κB.[38] Both IKKα and IKKβ are able to catalyze the phosphorylation of p65, although through different signaling pathways,[39] and are potential targets. Likewise, one or more of the kinases that activate IKK by phosphorylation, in response to TNFα or to the numerous other activators of NF-κB,[35] may be the targets.

Conclusions

We have demonstrated that the activation of NF-κB by TNFα can be effectively inhibited by a wide range of substituted trans-stilbenes and related compounds including hybrid stilbenes, many of which do not contain hydroxyl functional groups and, therefore, are no longer analogs of resveratrol and related natural products. Compounds were identified that were devoid of anti-oxidant activity but were at least 100-fold more potent than resveratrol.

The present invention is illustrated by the following examples/experimental. It is to be understood that the particular examples, materials, amounts, and procedures are to be interpreted broadly in accordance with the scope and spirit of the invention as set forth herein.

Experimental Section

Assay of the Anti-oxidant Activities of Resveratrol and Substituted Trans-stilbenes The anti-oxidant activities of resveratrol and substituted trans-stilbenes were determined using two standard assays,[40] the TRAP assay[41] and the FRAP assay.[42] For the TRAP assay, 2,2'-azinobis-(3-ethylbenzothiazoline-6-sulfonic acid) (ABTS) was reacted with potassium persulfate in the dark, overnight, to generate the colored $ABTS.^+$ radical cation, which has an absorption maximum at 734 nm. The activities of resveratrol and the series of substituted trans-stilbenes were determined by their abilities to quench the color of the radical cation. For the FRAP assay, the ferric complex of 2,4,6-tripyridyl-s-triazine was prepared at acidic pH, and the anti-oxidant activities of resveratrol and the substituted trans-stilbenes were determined by their abilities to reduce the ferric complex to the ferrous complex, monitored by formation of the ferrous complex at 593 nm. In both colorimetric assays, the vitamin E analog Trolox was used as a control.

Cell Assay

An NF-κB reporter stable cell line derived from human 293T embryonic kidney cells (293T/NF-κB-luc) (Panomics, Inc., Redwood City, Calif.) was grown in a humidified atmosphere at 37° C. in 5% $CO_2$/95% air. The cells were maintained in Dulbecco's Modified Eagle's Medium (DMEM—high glucose containing 4 mM glutamine) supplemented with 10% fetal bovine serum (FBS), 1 mM sodium pyruvate, 100 units/ml penicillin, 100 µg/ml streptomycin and 100 µg/ml hygromycin (Gibco/Invitrogen, Carlsbad, Calif.) to maintain cell selection. One day prior to treatment, the 293T/NFκB-luc cells were plated into 24-well cell culture plates (Costar, Cambridge, Mass.) at approximately 70% confluency in the above media without hygromycin. The following day cells were fed fresh media 1 hour prior to treatment. Media with or without recombinant tumor necrosis factor alpha (TNFα) (R&D Biosciences/Clontech, Palo Alto, Calif.) was then applied to the cells at 20 ng/ml followed by immediate treatments with resveratrol or substituted trans-stilbene. The cells were placed again in a humidified atmosphere at 37° C. in 5% $CO_2$/95% air for 7 hours. Plate wells were gently washed with phosphate buffered saline, pH 7.4, and lysed with 1× passive lysis buffer (Promega, Madison, Wis.). The subsequent lysates were analyzed with the Luciferase Assay System (Promega) utilizing a TD-20/20 luminometer (Turner Designs, Sunnyvale, Calif.). The firefly luciferase relative light units were normalized to protein (mg/ml) with BCA™ Protein Assay Kit (Pierce, Rockford, Ill.) and standardized to percent of control (TNFα control).

For assays of cell viability, cells were treated similarly as above and with 15 µM substituted trans-stilbene. After washing, cells were treated with 100 µl media and 20 µl CellTiter 96® $AQ_{ueous}$ One Solution reagent for 1 hour and then read at 490 nm with a Spectromax plate reader.

Inhibition of COX-2 Expression by Resveratrol and Analogs

Mouse microglial cells (BV-2) were cultured in RPMI-1640 (Cellgro, Herndon, Va.) supplemented with 10% FBS, 1 mM sodium pyruvate, 2 mM L-glutamine, 100 µg/ml streptomycin sulfate and 100 units/ml penicillin. Cells were grown on culture plates, pre-treated with 1% gelatin for 30 min, at 37° C. and passaged twice weekly. BV-2 cells were activated with 0.2 µg/ml lipopolysaccharide (LPS) (Sigma, St. Louis, Mo.). Those cells that were treated with LPS were incubated in parallel with resveratrol or resveratrol analogs 4cc (compound 2a) or 6p (LD-55, compound 1a) for 24 hours at the indicated concentrations. Total RNA was purified using RNeasy (Qiagen, Valencia, Calif.) and converted to cDNA using TaqMan Reverse Transcriptase (Applied Biosystems, Branchburg, N.J.). Cyclooxygenase-2 (COX-2) mRNA levels were measured using quantitative Real Time PCR analysis (qRT-PCR) of cDNA samples. Primers specific for COX-2 were designed to amplify a 132 base pair sequence flanking intron 7. Primer sequences for COX-2 were: upstream, TGGGGTGATGAGCAACTATT; downstream, AAGGAGCTCTGGGTCAAACT. qRT-PCR was performed using ABsolute QPCR SYBR Green Mix (Fisher Scientific, Atlanta, Ga.) with the following cycling parameters: 1 cycle, 95° C., 15 min; 40 cycles, 95° C., 15 sec, 60° C., 1 min. β-Actin mRNA levels were quantitated using identical cycling conditions and used to normalize values obtained for COX-2 expression.

TPA-induced Up-regulation of Activator Protein-1-Effects of Stilbenes

Assay of the Anti-oxidant Activities of Stilbene Analogs

The anti-oxidant activities of certain stilbene analogs according to the present invention were determined using two standard assays. See, Schlesier, et al., *Free Rad Res.* 2002; 36:177-187. The total radical-trapping anti-oxidant parameter assay (TRAP assay) measures the ability of an analog to react with the pre-formed radical monocation of 2,2'-azinobis-(3-ethylbenzothiazoline-6-sulfonic acid) (ABTS.[+]). See, Re, et al., *Free Rad Biol Med*, 26:1231-1237 (1999). ABTS was reacted with potassium persulfate in the dark, overnight, to generate the colored ABTS.[+] radical cation, which has an absorption maximum at 734 nm. The activities of curcumin and analogs were determined by their abilities to quench the color of the radical cation. The ferric reducing/anti-oxidant power assay (FRAP assay) measures the ability of an analog to reduce a ferric tripyridyltriazine complex. See, Benzie and Strain, *Meth Enzymol*, 299:15-27 (1999). The ferric complex of 2,4,6-tripyridyl-s-triazine was prepared at acidic pH, and the anti-oxidant activities of curcumin and analogs were determined by their abilities to reduce the ferric complex to the ferrous complex, monitored by formation of the ferrous complex at 593 nm. In both colorimetric assays, the vitamin E analog Trolox was used as a control.

Assay of the Activities of Stilbene Analogs as Inhibitors of the TPA-induced Activation of AP-1

An AP-1 reporter stable cell line derived from human 293T embryonic kidney cells transfected with a luciferase reporter construct containing three AP-1 binding sites in the promoter (293T/AP-1-luc, Panomics, Inc., Redwood City, Calif.) was grown in a humidified atmosphere at 37° C. in 5% $CO_2$/95% air. The cells were maintained in Dulbecco's Modified Eagle's Medium (DMEM—high glucose containing 4 mM glutamine) supplemented with 10% fetal bovine serum (FBS), 1 mM sodium pyruvate, 100 units/ml penicillin, 100 µg/ml streptomycin and 100 µg/ml hygromycin (Gibco/Invitrogen, Carlsbad, Calif.) to maintain cell selection. One day prior to treatment, the 293T/AP-1-luc cells were plated into 24-well cell culture plates (Costar, Cambridge, Mass.) in the above media without hygromycin. The following day, the cells, which were at approximately 60% confluency, were fed fresh media with or without TPA, 10 ng/ml, (Calbiochem) and immediately treated with curcumin or analog prepared in DMSO stock solutions. The cells were placed again in a humidified atmosphere at 37° C. in 5% $CO_2$/95% air for 24 hours. Plate wells were gently washed with phosphate buffered saline, pH 7.4, and lysed with Ix passive lysis buffer (Promega, Madison, Wis.). The subsequent lysates were analyzed with the Luciferase Assay System (Promega) utilizing a TD-20/20 luminometer (Turner Designs, Sunnyvale, Calif.). The firefly luciferase relative light units were normalized to protein (mg/ml) with BCA Protein Assay Kit (Pierce, Rockford, Ill.) and standardized to percent of control (TPA control).

The results for a number of the stilbene compounds according to the present invention which were assayed as described above are set forth in the following Table 2 as well as the attached FIGS. 7-12. As can be seen from the presented data, the stilbene compounds according to the present invention exhibit significant activity against AP-1.

TABLE 2

$IC_{50}$ values of resveratrol and substituted trans-stilbenes for inhibition of the TPA-induced activation of AP-1.

| Number | Structure | $IC_{50}$ (µM) | Anti-oxidant Activity | | CLogP |
|---|---|---|---|---|---|
| | | | TRAP | FRAP | |
| Resveratol 1 | 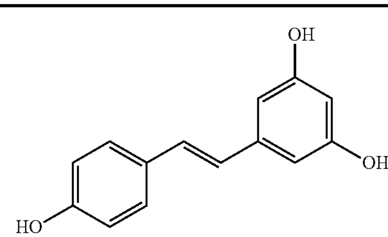 | activated | + | + | 2.833 |
| 4b | 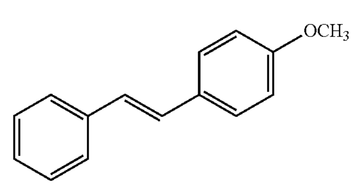 [SMILES: COc1ccc(/C=C/c2ccccc2)cc1] | 1.3 ± 0.03 | − | + | 4.753 |

TABLE 2-continued

IC$_{50}$ values of resveratrol and substituted trans-stilbenes for inhibition of the TPA-induced activation of AP-1.

| Number | Structure | IC$_{50}$ (µM) | Anti-oxidant Activity | | CLogP |
|---|---|---|---|---|---|
| | | | TRAP | FRAP | |
| 4d | 4-CH$_3$ stilbene | 1.6 ± 0.6 | − | + | 5.333 |
| 4k | 4-OCH$_2$CH$_3$ stilbene | 0.8 ± 0.1 | − | + | 5.282 |
| 4t | 4-OCH$_3$, 3-OH stilbene | 0.8 ± 0.05 | + | + | 4.016 |
| 4cc | 4-N(CH$_3$)$_2$ stilbene | 1.1 ± 0.1 | + | + | 4.999 |
| 6r | 4-OCH$_3$, 3′-OCH$_3$ stilbene | 0.7 ± 0.04 | − | − | 4.672 |
| 6i | 4-OCH$_3$, 3′-CH$_3$ stilbene | 1.0 ± 0.12 | − | − | 5.252 |
| 6f | 4-OCH$_3$, 3′,5′-(OCH$_3$)$_2$ stilbene | 3.8 ± 1.1 | − | − | 4.761 |

TABLE 2-continued
IC$_{50}$ values of resveratrol and substituted trans-stilbenes for inhibition of the TPA-induced activation of AP-1.
| Number | Structure | IC$_{50}$ (μM) | Anti-oxidant Activity | | CLogP |
| --- | --- | --- | --- | --- | --- |
| | | | TRAP | FRAP | |
| 6o | 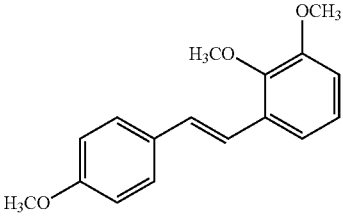 | 2.4 ± 0.7 | – | – | 4.411 |
| 8i | 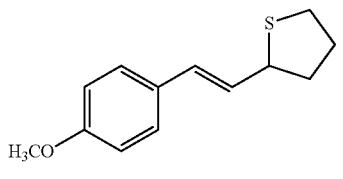 | 2.5 ± 0.5 | – | – | 4.399 |
| 6p | 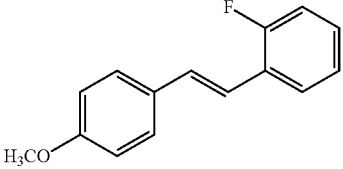 [SMILES: COc1ccc(/C=C/c2ccccc2F)cc1] | 0.8 ± 0.1 | – | – | 4.896 |
| 6n | 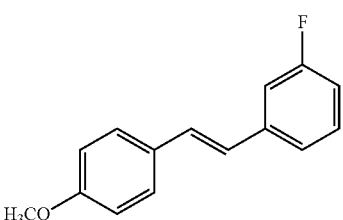 | 0.5 ± 0.1 | – | – | 4.896 |
| | 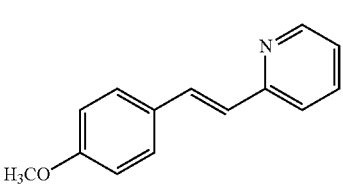 [SMILES: COc1ccc(/C=C/c2ccccn2)cc1] | 2.1 ± 0.4 | – | – | 3.256 |
| 6h | 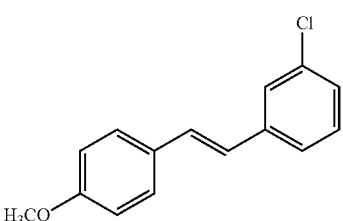 | 0.8 ± 0.15 | – | – | 5.466 |
| 6d | 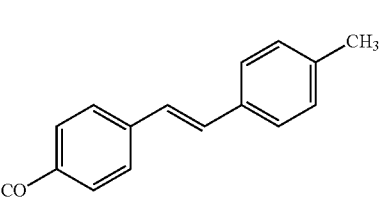 | 0.8 ± 0.03 | – | – | 5.252 |

Chemical Synthesis

General Method for Synthesis of (E) Stilbenes

To a solution of phosphonic acid diethyl ester (5 mmol) in 10 mL of dry DMF there was added sodium methoxide (10 mmol) and 18/6 crown ether (2 mmol). The resulting mixture was stirred at room temperature for five minutes and the appropriate aldehyde or hydroxybenzaldehyde methoxymethyl ether (6 mmol) dissolved in 5 mL of DMF was added dropwise at 0° C. The mixture was stirred at room temperature for one hour and then for five hours at 120° C. The reaction was quenched by pouring into 200 mL of water with stirring. Reactions that gave solids were filtered and recrystallized from hexane or ethanol. Reactions that gave oils were extracted into ether and the ether layer was washed with water, saturated salt and dried ($MgSO_4$). Filtration and evaporation of the ether afforded oily solids that were purified by recrystallization or chromatography (hexane/ethyl acetate). Methoxymethyl protected hydroxystilbenes were heated in methanol containing 2 drops of concentrated hydrochloric acid to give hydroxystilbenes.[43]

(E)-2,6-Dimethoxystilbene (4g). mp 45-46° C.; $^1$H NMR: δ 3.89 (s, 6H), 7.18 (m, 6H), 7.33 (t, 1H, J=7.35 Hz), 7.45 (d, 1H, J=16.68 Hz), 7.53 (d, 2H, J=6.75 Hz). Exact mass calcd for $C_{16}H_{16}O_2$: 240.1550, observed (M+H) 241.1228.

(E)-3-Hydroxy-4-methoxystilbene (4s). mp 149-153° C.; $^1$H NMR: δ 3.88 (s, 3H), 5.65 (s, 1H), 6.82 (d, 1H, J=8.34 Hz), 6.97 (m, 3H), 7.15 (s, 1H, J=1.98 Hz), 7.23 (m, 1H), 7.34 (t, 2H, J=7.35 Hz), 7.48 (d, 2H, J=7.15 Hz). Exact mass calcd for $C_{15}H_{14}O_2$: 226.0994, observed (M+H) 227.1072.

(E)-2-Trifluoromethylstilbene (4z). oil; $^1$H NMR: δ 7.07 (d, 1H, J=16.09 Hz), 7.36 (m, 5H), 7.52 (m, 3H), 7.65 (d, 1H, J=7.75 Hz), 7.77 (d, 1H, J=7.95 Hz). Exact mass calcd for $C_{15}H_{11}F_3$: 248.0813, observed (M+H) 249.0891.

(E)-2,6-Dichlorostilbene (4dd). oil; $^1$H NMR: δ 7.13 (m, 2H), 7.35 (m, 6H), 7.54 (d, 2H, J=7.54 Hz). Exact mass calcd for $C_{14}H_{10}Cl_2$: 298.1569, observed (M+H) 299.1647.

(E)-2,4',6-Trimethoxystilbene (6g). mp 45-46° C.; $^1$H NMR: δ 3.72 (s, 3H), 3.79 (s, 6H), 6.49 (d, 2H, J=8.34 Hz), 6.79 (d, 2H, J=8.74 Hz), 7.05 (t, 1H, J=8.34 Hz), 7.24 (d, 1H, J=16.68 Hz) 7.39 (d, 2H, J=8.74 Hz), 7.45 (d, 1H, J=16.48 Hz). Exact mass calcd for $C_{17}H_{18}O_3$: 270.1256 observed (M+H) 271.1334.

(E)-2,3,4,4'-Tetramethoxystilbene (6s). mp 124-125° C.; $^1$H NMR: δ 3.81 (s, 3H), 3.86 (s, 3H), 3.89 (s, 6H), 6.68 (d, 1H, J=8.74 Hz), 6.88 (d, 2H, J=8.74 Hz), 6.96 (d, 1H, J=16.68 Hz), 7.19 (d, 1H, J=16.29 Hz), 7.27 (d, 1H, J=8.74 Hz), 7.44 (d, 2H, J=8.74 Hz). Exact mass calcd for $C_{18}H_{20}O_4$: 300.1362, observed (M+H) 301.1440.

(E)-2-Ethyl-3,4,4'-trimethoxystilbene (6v). mp 97-98° C.; $^1$H NMR: δ 1.17 (t, 3H, J=7.55 Hz), 2.80 (q, 2H, J=7.54 Hz), 3.81 (s, 3H), 3.82 (s, 3H), 3.86 (s, 3H), 6.78 (m, 2H) 6.87 (m, 3H), 7.14 (d, 1H, J=15.89 Hz), 7.31 (d, 1H, J=8.54 Hz), 7.42 (d, 2H, J=8.54 Hz); $^{13}$C NMR: δ 15.4, 19.7, 55.4, 55.8, 60.9, 110.1, 114.1, 121.2, 124.1, 127.5, 128.4, 129.9, 130.8, 136.2, 146.8, 152.0, 159.0. Exact mass calcd for $C_{19}H_{22}O_3$: 298.1569, observed (M+H) 299.1647.

(E)-3-Bromo-4'-methoxystilbene (6w). mp 114-115° C.; $^1$H NMR: δ 3.18 (s, 3H), 6.87 (m, 3H), 7.04 (d, 1H, J=16.28 Hz), 7.18 (t, 1H, J=7.75 Hz), 7.35 (m, 2H), 7.43 (d, 2H, J=8.74 Hz), 7.63 (s, 1H). Exact mass calcd for $C_{15}H_{13}BrO$: 288.0150, observed (M+H) 289.0228.

(E)-2-Trifluoromethyl-4'-methoxystilbene (6z). oil; $^1$H NMR: δ 3.80 (s, 3H), 6.89 (d, 2H, J=8.74 Hz), 7.01 (d, 1H, J=16.10 Hz), 7.31 (m, 2H), 7.48 (m, 3H) 7.63 (d, 1H, J=7.74 Hz), 7.74 (d, 1H, J=7.75 Hz). Exact mass calcd for $C_{16}H_{13}F_3O$: 278.0918, observed (M+H) 279.0996.

(E)-4'-Methoxy-2,4,6-trimethylstilbene (6aa). mp 68-69° C.; $^1$H NMR: δ 2.28 (s, 3H), 2.33 (s, 6H), 3.82 (s, 3H), 6.51 (d, 1H, J=16.69 Hz), 6.91 (m, 5H), 7.42 (d, 2H, J=8.73 Hz). Exact mass calcd for $C_{18}H_{20}O$: 252.1514, observed (M+H) 253.1592.

(E)-2,3-Dihydroxy-4'-methoxystilbene (6cc). mp 125-126° C.; $^1$H NMR: δ 3.82 (s, 3H), 5.18 (s, 1H), 5.54 (s, 1H), 6.75 (m, 2H), 6.88 (d, 2H, J=8.74 Hz), 7.07 (m, 2H), 7.19 (d, 1H, J=16.29 Hz), 7.45 (d, 2H, J=8.73 Hz). Exact mass calcd for $C_{15}H_{14}O_3$: 242.0943, observed (M+H) 243.1021.

General methods for synthesis of benzyl phosphonic acid diethyl esters and MOM-protected hydroxybenzaldehydes, physical and spectroscopic data for reported compounds 4a-4f, 4h-4r, 4t-4y, 4aa-4cc, 4ee-4gg, 6a-6f, 6h-6r, 6t, 6u, 6x, 6y, 6bb, 6dd, 6ee, 8a-8j appears below.

Unless otherwise noted all reagents were obtained from commercial sources and used without further purification. All compounds that were isolated were greater than 90% pure by $^1$H and/or $^{13}$C NMR. Column chromatographic separations were performed using EM Science type 60 silica gel (230-400 mesh). Melting points were determined on a Thomas Hoover capillary melting point apparatus and are uncorrected. NMR spectra were recorded on a Bruker AC250 (250 MHz) NMR spectrometer in $CDCl_3$ unless otherwise noted. Chemical shifts are reported in ppm (δ) relative to $CHCl_3$ at 7.24 ppm for $^1$H NMR and 77.0 for $^{13}$C NMR. High resolution mass spectra were performed at the Mass Spectrometry Facility, University of New Mexico.

General Method for the Preparation of Substituted Benzyl Phosphonic Acid Diethyl Esters.

Substituted benzyl bromide was heated with excess triethylphosphite at 140° C. until the evolution of bromoethane had ceased and complete dissolution occurred. The remaining triethylphosphite was then removed by concentration of the solution in vacuo to afford the product.

General Method for the Preparation of MOM Protected Aldehydes.

To a suspension of hexane rinsed sodium hydride (1.5 equivalents) in dimethyl formamide is added a solution of the appropriate aldehyde (1 equivalent) in dimethyl formamide. After stirring 2 hours at room temperature dichloromethylmethyl ether is added and the solution is stirred an additional 3 hours at room temperature. The solution is quenched by pouring over ice water and extracted with ether. The ether extracts are washed with 1M sodium hydroxide, saturated sodium chloride and dried with magnesium sulfate, filtered and evaporated to give a crude oil that is distilled bulb to bulb to afford the product as a solid.

(E)-3,4-Dimethoxystilbene (4a). mp 108-109° C. [lit.[1] 112-113° C.].

(E)-4-Methoxystilbene (4b). mp 134-135° C. [lit.[2] 135-136° C.].

(E)-4-Chlorostilbene (4c). mp 129-130° C. [lit.[3] 129-131° C.].

(E)-4-Methylstilbene (4d). mp 114-116° C. [lit.[3] 118-120° C.].

(E)-4-Cyanostilbene (4e). mp 116-117° C. [lit.[3] 115-118° C.].

(E)-3,5-Dimethoxystilbene (4f). mp 53-55° C. [lit.[4] 54-55° C.].

(E)-3-Chlorostilbene (4h). mp 74-76° C. [lit.[5] 71-72.5° C.].

(E)-3-Methylstilbene (4i). mp 50-51° C. [lit.[6] 48-49° C.].

(E)-2-Chlorostilbene (4j). mp 64-66° C. [lit.[7] 37-38° C.].

(E)-4-Ethoxystilbene (4k). mp 124-126° C. [lit.[8] 77-78° C.].
(E)-4-Hydroxystilbene (4l). mp 183-185° C. [lit.[9] 188° C.].
(E)-4-Fluorostilbene (4m). mp 123-124° C. [lit.[10] 124° C.].
(E)-3-Fluorostilbene (4n). mp 74-76° C. [lit.[11] 70-72° C.].
(E)-2,3-Dimethoxystilbene (4o). mp 37-39° C. [lit.[12] 38-39° C.].
(E)-2-Fluorostilbene (4p). mp 103-105° C. [lit.[13] 102-103° C.].
(E)-4-Hydroxy-3-methoxystilbene (4q). mp 133-134° C. [lit.[9] 138° C.].
(E)-3-Methoxystilbene (4r). mp 34-35° C. [lit.[2] 34-35° C.].
(E)-3-Hydroxystilbene (4t). mp 119-121° C. [lit.[14] 119-120° C.].
(E)-2,4-Dimethoxystilbene (4u). mp 64-65° C. [lit.[15] 64.5-65° C.].
(E)-2-Methylstilbene (4v). mp 35-36° C. [lit.[2] 28-29° C.].
(E)-3-Trifluoromethylstilbene (4w). mp 67-68° C. [lit.[16] 66-67° C.].
(E)-4-Trifluoromethylstilbene (4x). mp 133-134° C. [lit.[2] 134-135° C.].
(E)-2,5-Dimethoxystilbene (4y). oil; $^1$H NMR: δ 3.81 (s, 3H), 3.83 (s, 3H), 6.80 (m, 2H), 7.09 (d, 1H, J=16.48 Hz), 7.16 (d, 1H, J=2.38 Hz), 7.25 (m, 1H), 7.34 (t, 2H, J=7.35 Hz), 7.47 (d, 1H, J=16.49 Hz), 7.53 (d, 2H, J=7.15 Hz).
(E)-2,4,6-Trimethylstilbene (4aa). mp 56-57° C. [lit.[17] 49-50° C.].
(E)-2-Methoxystilbene (4bb). mp 58-59° C. [lit.[2] 56-57° C.].
(E)-4-N,N-Dimethylaminostilbene (4cc). mp 144-146° C. [lit.[18] 150° C.].
(E)-3,4-Dihydroxystilbene (4ee). mp 167-168° C. [lit.[19] 168-169° C.].
(E)-3,4,5-Trimethoxystilbene (4ff). mp 107-108° C. [lit.[20] 105-106° C.].
(E)-2,3,4-Trimethoxystilbene (4gg). mp 80-83° C. [lit.[20] 79-82° C.].
(E)-3,4,4'-Trimethoxystilbene (6a). mp 136-138° C. [lit.[4] 136-138° C.].
(E)-4,4'-Dimethoxystilbene (6b). mp 212-213° C. [lit.[2] 214-216° C.].
(E)-4-Chloro-4'-methoxystilbene (6c). mp 181-183° C. [lit.[4] 181-184° C.].
(E)-4'-Methoxy-4-methylstilbene (6d). mp 160-162° C. [lit.[21] 166-167° C.].
(E)-4-Cyano-4'-methoxystilbene (6e). mp 141-143° C. [lit.[22] 141-142° C.].
(E)-3,4',5-Trimethoxystilbene (6f). mp 53-55° C. [lit.[4] 53-56° C.].
(E)-3-Chloro-4'-methoxystilbene (6h). mp 93-94° C. [lit.[21] 96° C.].
(E)-4'-Methoxy-3-methylstilbene (6i). mp 110-111° C. [lit.[21] 98° C.].
(E)-2-Chloro-4'-methoxystilbene (6j). mp 52-53° C. [lit.[23] 59-60° C.].
(E)-4-Ethoxy-4'-methoxystilbene (6k). mp 194-195° C. [lit.[24] 165-167° C.].
(E)-3,4,4',5-Tetramethoxystilbene (6l). mp 157-159° C. [lit.[20] 152-155° C.].
(E)-4-Fluoro-4'-methoxystilbene (6m). mp 148-150° C. [lit.[25] 147-149° C.].
(E)-3-Fluoro-4'-methoxystilbene (6n). mp 108-110° C. [lit.[11] 108-110° C.].
(E)-2,3,4'-Trimethoxystilbene (6o). mp 70-72° C. [lit.[26] 73-74° C.].
(E)-2-Fluoro-4'-methoxystilbene (6p). mp 100-101° C. [lit.[13] 102-103° C.].
(E)-2,4,4',5-Tetramethoxystilbene (6q). mp 106-107° C. [lit.[27] 110° C.].
(E)-3,4'-Dimethoxystilbene (6r). mp 107-108° C. [lit.[26] 107-108° C.].
(E)-4-Bromo-4'-methoxystilbene (6t). mp 200-201° C. [lit[28] 177-179° C.].
(E)-2,4,4'-Trimethoxystilbene (6u). mp 94-95° C. [lit.[29] 89° C.].
(E)-3,4-Dihydroxy-4'-methoxystilbene (6x). mp d 186° C. [lit[30]]; $^1$H NMR: (DMSO-d$_6$) δ 3.75 (s, 3H), 6.70 (d, 1H, J=8.94 Hz), 6.87 (m, 6H), 7.45 (d, 2H, J=8.34 Hz), 8.88 (s, 1H), 9.00 (s, 1H).
(E)-2,4',5-Trimethoxystilbene (6y). mp 67-68° C. [lit.[31] oil]; $^1$H NMR: δ 3.80 (s, 3H), 3.81 (s, 3H), 3.82 (s, 3H), 6.80 (m, 2H), 6.88 (d, 2H, J=8.74 Hz), 7.04 (d, 1H, J=16.48 Hz), 7.13 (d, 1H, J=2.78 Hz), 7.32 (d, 1H, J=16.48 Hz), 7.47 (d, 2H, J=8.74 Hz).
(E)-2,4'-Dimethoxystilbene (6bb). mp 89-90° C. [lit.[32] 85-86° C.].
(E)-4'-Methoxy-4-N,N-dimethylaminostilbene (6dd). mp 182-183° C. [lit.[33] 185-186° C.].
(E)-2,6-Dichloro-4'-methoxystilbene (6ee). mp 56-60° C.; $^1$H NMR: δ 3.83 (s, 3H), 6.92 (d, 2H, J=8.74 Hz), 7.05 (m, 3H), 7.33 (d, 2H, J=7.94 Hz), 7.49 (d, 2H, J=8.54 Hz).
(E)-3-Stilbazole (8a). mp 81-82° C. [lit.[34] 83-85° C.].
(E)-4-Stilbazole (8b). mp 124-126° C. [lit.[35] 128° C.].
(E)-2-Stilbazole (8c). mp 89-91° C. [lit.[36] 93° C.].
(E)-2-Styrylthiophene (8d). mp 111-112° C. [lit.[36] 112-113° C.].
(E)-2-Styrylnaphthalene (8e). mp 147-148° C. [lit.[37] 147-148° C.].
(E)-1-Styrylnaphthalene (8f). mp 71-72° C. [lit.[38] 71-72° C.].
(E)-2-(4-Methoxystyryl)naphthalene (8g). mp 172-173° C. [lit.[39] 142° C.].
(E)-1-(4-Methoxystyryl)naphthalene (8h). mp 93-94° C. [lit.[40] 92-93° C.].
(E)-2-(4-Methoxystyryl)thiophene (8i). mp 133-134° C. [lit.[41] 134-135° C.].
(E)-4'-Methoxy-3-stilbazole (8j). mp 98-100° C. [lit.[42] 99-100° C.].

Compound 3 (Z-Stilbene) of Scheme 4

To 1 mmol of the phosphonium salt (1) dissolved in 2 mL of dichloromethane, the aryl aldehyde (2, 1 mmol) and 18-crown-6 (0.05-0.1 mmol) were added. The mixture was cooled to −70° C. and freshly powdered potassium hydroxide (2 mmol) was added under stirring. The reaction was stirred at −40° C. until tlc indicated complete reaction. The mixture was diluted with dichloromethane and water. The dichloromethane layer was separated washed with water, saturated salt solution and dried over magnesium sulfate. Filtration and evaporation afforded a crude product (3) that was purified by preparative thin layer chromatography. A number of analogs are synthesized using this general method and tested in the NF-κB assay. See FIG. 13. Also, see, Bellucci, G.; Chiappe, C.; Lo Moro, G. *Tetrahedron Lett.*, 1996, 37, 4225-4228.

Further Examples—Skin Diseases/Conditions

Anti-Inflammatory Activity of LD55 Against Skin Conditions

Introduction: The transcription factor NF-κB is well known as a regulator of genes controlling immune and inflammatory responses (1). The transcription factor AP-1 contributes to many cellular processes such as proliferation, cell cycle regulation, differentiation, and apoptosis (2), but also participates in the regulation of inflammation (3). There is strong overlap among the signaling pathways that involve NF-κB and AP-1 (4,5). Therefore, inhibitors that down-regulate both pathways may be especially effective as anti-inflammatory agents. Previously, we described the synthesis of a number of inhibitors of NF-κB and/or AP-1 (6-9), some of which are shown in the Tables below.

Compound 5 in Table 2A (below), which we designated LD55 (FIG. 14), was compared with another trans-stilbene resveratrol for ability to prevent brain inflammation and plaque accumulation in a transgenic model of Alzheimer's disease and was found to be effective (10). This also raised the question whether LD55 would show broad anti-inflammatory activity.

In this disclosure, we demonstrate that LD55 is highly effective in treating inflammatory skin conditions in cats and dogs with a variety of skin pathologies (Table 3) that also have associated inflammation. We propose that LD55 will be generally effective in veterinary and human medicine to treat inflammatory skin conditions.

TABLES 1A and 2A

| Number | Structure | AP-1 IC$_{50}$ (μM) | NFκB IC$_{50}$ (μM) |
|---|---|---|---|
| | Inhibitors of NF-κB and AP-1 signaling pathways | | |
| | Analogs from the curcumin library that are inhibitors of the TNFα-induced activation of NF-κB and of the TPA-induced activation of AP-1 in Panomics reporter screening cells. | | |
| 1 | Curcumin | 12.8 ± 0.5 | 8.2 ± 0.4 |
| 2 | 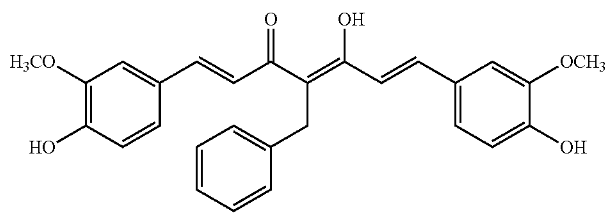 [SMILES: COc1cc(/C=C/C(=O)/C(Cc2ccccc2)=C(O)/C=C/c2ccc(O)c(OC)c2)ccc1O] | 5.3 ± 0.7 | 6.3 ± 0.5 |
| 3 | 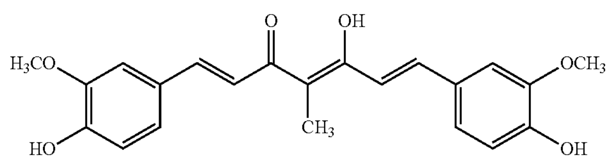 [SMILES: COc1cc(/C=C/C(=O)/C(C)=C(O)/C=C/c2ccc(O)c(OC)c2)ccc1O] | 6.0 ± 0.2 | 6.7 ± 1.2 |
| 4 | 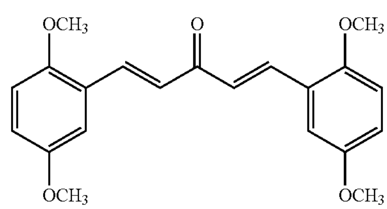 [SMILES: COc1ccc(OC)c(/C=C/C(=O)/C=C/c2cc(OC)ccc2OC)c1] | 1.4 ± 0.2 | 6.5 ± 0.9 |
| 5 | 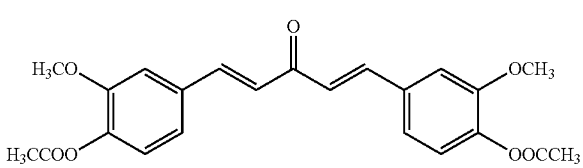 | 8.3 ± 0.6 | 5.3 ± 1.1 |
| 6 | 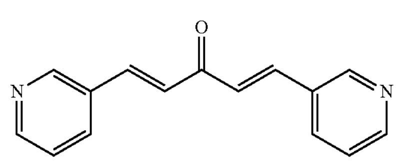 [SMILES: O=C(/C=C/c1cccnc1)/C=C/c1cccnc1] | 4.1 ± 0.1 | 3.4 ± 0.2 |

TABLES 1A and 2A-continued

Inhibitors of NF-κB and AP-1 signaling pathways

| Number | Structure | AP-1 IC$_{50}$ (μM) | NFκB IC$_{50}$ (μM) |
|---|---|---|---|
| 7 | [structure: 1,5-bis(2-trifluoromethylphenyl)-1,4-pentadien-3-one] | 7.1 ± 0.3 | 5.0 ± 0.3 |
| 8 | [structure: 2,6-bis(4-hydroxy-3-methoxybenzylidene)cyclohexanone] | 7.3 ± 0.4 | 4.4 ± 0.8 |
| 9 | [structure: 1,5-bis(4-pyridyl)-1,4-pentadien-3-one] | 8.2 ± 0.3 | 3.9 ± 0.3 |

Analogs from the resveratrol library that are inhibitors of the TNFα-induced activation of NF-κB and of the TPA-induced activation of AP-1 in Panomics reporter screening cells.

| | | | |
|---|---|---|---|
| 1 | [structure: 4-ethoxystilbene] | 0.8 ± 0.1 | 0.3 ± 0.03 |
| 2 | [structure: 4-(dimethylamino)stilbene] | 1.1 ± 0.1 | 0.15 ± 0.1 |
| 3 | [structure: 3-methoxy-4'-methoxystilbene] | 0.7 ± 0.04 | 0.6 ± 0.1 |
| 4 | [structure: 3-methyl-4'-methoxystilbene] | 1.0 ± 0.12 | 0.8 ± 0.2 |

TABLES 1A and 2A-continued

| Number | Structure | AP-1 IC$_{50}$ (μM) | NFκB IC$_{50}$ (μM) |
|---|---|---|---|
| 5 | 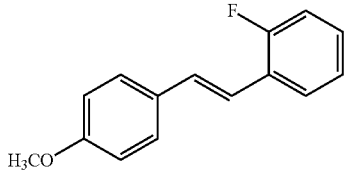 [SMILES: COc1ccc(/C=C/c2ccccc2F)cc1] | 0.8 ± 0.1 | 0.15 ± 0.1 |
| 6 | 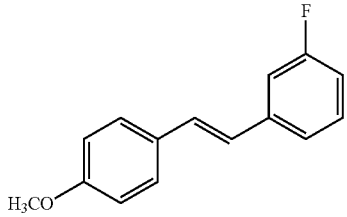 [SMILES: COc1ccc(/C=C/c2cccc(F)c2)cc1] | 0.5 ± 0.1 | 1.1 ± 0.6 |
| 7 | 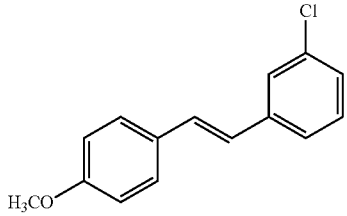 [SMILES: COc1ccc(/C=C/c2cccc(Cl)c2)cc1] | 0.8 ± 0.15 | 1.0 ± 0.1 |
| 8 | 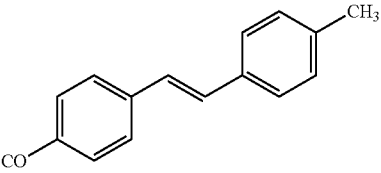 | 0.8 ± 0.03 | 0.9 ± 0.1 |

Table 3 summarizes the results from consecutive treatment with LD55 of dogs and cats with inflammatory skin conditions, where LD55 was applied as a 1% lotion. With the exception of two dogs where the outcome is unknown, all treated animals showed marked improvement in the inflammatory component of their pathology as demonstrated by reduced redness/itching and reduced discomfort.

In a number of cases, pictures were obtained before and after treatment.

FIGS. 15A and B: Treatment of Animal 1139

Conner (1139) is a 6 year old, neutered Border Collie. The left photo 15A. was taken before the start of daily application of LD55 and the right photo was taken after treatment. Before treatment, the nasal planum was cracked, crusty and bleeding above the right nostril. After 10 applications of

TABLE 3

Examples of faunae treated with LD55

| Date | number/name | species | breed | disease | outcome |
|---|---|---|---|---|---|
| Jun. 12, 2013 | 3688/katie | K9 | Ger. Shep | peri-analfistual | positive |
| Aug. 5, 2013 | 255/phoenix | Feline | tabby | atopy/ears | positive |
| Aug. 13, 2013 | 836/fiona | K9 | Gold. Ret | atopy | positive |
| Aug. 19, 2013 | 324/ace | K9 | Gold. Ret | hot spot | positive |
| Aug. 27, 2013 | 3883/chewy | K9 | Pit | hemangiosarcoma | unknown |
| Sep. 3, 2013 | 2410/teaser | K9 | Austr Terr | atopy | unknown |
| Sep. 14, 2013 | 3826/lil miskitty | Feline | Grey Tabby | squamous cell carcinoma | positive |
| Sep. 16, 2013 | 438/amber | K9 | LabX | hemangiosarcoma | positive |
| Sep. 16, 2013 | 2521/buckley | K9 | Aust Shep | Pempigus | positive |
| Sep. 16, 2013 | 1139/conner | K9 | Aust Shep | Pempigus | positive |
| Sep. 25, 2013 | 520/Shiloa | K9 | LabX | Pempigus | positive |

LD55 the region was healing, the dried, flaking skin was gone and there was no bleeding (FIG. 15B).

Figure 16:

FIG. 16: Treatment of Animal 255

Phoenix (255) is an 18 year old spayed female tabby. This spring severe allergies caused her to scratch the ears and the sides of her face. LD55 applied twice a day caused the redness to disappear within 24 hours, as shown in the figure.

FIG. 17: Treatment of Animal 3688

Katie (3688) is a 9 year old, spayed, female German Shepherd. She has had these peri-anal fistulas for several years (left). Using LD55 with combinations of standard forms of treatment, nearly resulted in the fistula healing and closing in two weeks.

Nanoemulsion of LD-55 with and without Antibiotic

Reference: The preparation of 3,5-dihydroxy-4-isopropylstilbene nanoemulsion and in vitro release. Yue Zhang, Jungang Gao, Hetang Zheng, Ran Zhang, and Yucui Han. International Journal of Nanomedicine, 2011: 6 pg. 649-657.

Procedure: (the procedure is a modification of the procedure in the above reference).

The isopropyl myristate (IPM), Kolliphor EL and chlorhexidine digluconate solution (20%) were purchased from Sigma-Aldrich.

1% LD-55:

A 1% LD-55 nanoemulsion was prepared as per the reference with these modifications.

Two hundred and twenty milligrams of LD-55 was placed in a 50 ml glass test-tube. Ten m/s of IPM (oil) was added to the tube. The solution was heated slightly and mixed until the LD-55 went into solution. The 10 m/s was added to a 40 ml amber vial containing 4.5 ml of Kolliphor EL. The 50 ml tube was then washed with 4 ml of IPM and this wash was also added to the vial. The solution was stirred and mixed well with a spatula. Next, 3.5 ml of millipore filtered water was added drop-wise while continuously stirring until a transparent, smooth nanoemulsion was formed. A total volume of 22 mls was then sealed and stored at room temperature.

1% LD-55 Containing 2% Chlorhexidine Digluconate:

A 1% LD-55 nanoemulsion containing 2% antibiotic was prepared as above substituting a 12.5% solution of chlorhexidine digluconate (antibiotic) for the 3.5 mls of water.

For any other antibiotic, either the antibiotic can be added with LD-55 to the oil phase if the antibiotic is hydrophobic, or the antibiotic can be added to the water, as above.

Note: The use of chlorhexidine digluconate in this preparation was dictated by the wide use of this antibiotic for topical application in veterinary medicine.

Some topical antibiotics are available without a prescription and are sold in many forms, including creams, ointments, powders, and sprays. Some widely used topical antibiotics are bacitracin, neomycin, mupirocin, and polymyxin B. Among the products that contain one or more of these ingredients are Bactroban (a prescription item), Neosporin, Polysporin, and Triple Antibiotic Ointment or Cream.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

REFERENCES (FIRST SET)

1. Yamamoto, Y.; Gaynor, R. B. Therapeutic potential of inhibition of the NF-kappaB pathway in the treatment of inflammation and cancer. *J. Clin. Invest.* 2001, 107, 135-142.
2. Kim, H. J.; Hawke, N.; Baldwin, A. S. NF-κB and IKK as therapeutic targets in cancer. *Cell Death Different.* 2006, advanced online publication.
3. Kaltschmidt, B.; Widera, D.; Kaltschmidt, C. Signaling via NF-κB in the nervous system. *Biochim. Biophys. Acta* 2005, 1745, 287-299.
4. Viatour, P.; Merville, M-P.; Bours, V.; Chariot, A. Phosphorylation of NF-kappaB and IkappaB proteins: implications in cancer and inflammation. *Trends Biochem. Sci.* 2005, 30, 43-52.
5. Kumar, A.; Takada, Y.; Boriek, A. M.; Aggarwal, B. B. Nuclear factor-κB: its role in health and disease. *J. Mol. Med.* 2004, 82, 434-448.
6. Hiscott, J.; Kwon, H.; Genin, P. Hostile takeovers: viral appropriation of the NF-kappaB pathway. *J. Clin. Invest.* 2001, 107, 143-151.
7. Barkett, M.; Gilmore, T. Control of apoptosis by Rel/NF-kappaB transcription factors. *Oncogene* 1999, 18, 6910-6924.
8. Karin, M.; Greten, F. R. NF-κB: linking inflammation and immunity to cancer development and progression. *Nature Rev. Immunol.* 2005, 5, 749-759.
9. Herrmann, O.; Baumann, B.; de Lorenzi, R.; Muhammad, S.; Zhang, W.; Kleesiek, J.; Malfertheiner, M.; Kohrmann, M.; Potrovita, I.; Maegele, I.; Beyer, C.; Burke, J. R.; Hasan, M. T.; Bujard, H.; Wirth, T.; Pasparakis, M.; Schwaninger, M. IKK mediates ischemia-induced neuronal death. *Nat. Med.* 2005, 11, 1322-1329.
10. Schmitz, M. L.; Mattioli, I.; Buss, H.; Kracht, M. NF-κB: a multifaceted transcription factor regulated at several levels. *ChemBioChem* 2004, 5, 1348-1358.
11. http://people.bu.edu/gilmore/nf-kb/inhibitors
12. Dore, S. Unique properties of polyphenol stilbenes in the brain: more than direct antioxidant actions; gene/protein regulatory activity. *Neurosignals* 2005, 14, 61-70.
13. Kundu, J. K.; Surh, Y-J. Molecular basis of chemoprevention by resveratrol: NF-κB and AP-1 as potential targets. *Mut. Res.* 2004, 555, 65-80.
14. Shimizu, M.; Weinstein, B. Modulation of signal transduction by tea catechins and related phytochemicals. *Mut. Res.* 2005, 591, 147-160.
15. Renaud, S.; de Lorgeril, M. Wine, platelets, and the French paradox for coronary heart disease. *Lancet* 1992, 339, 1523-1526.
16. Jang, M.; Cai, L.; Udeani, G. O.; Slowing, K. V.; Thomas, C. F.; Beecher, C. W.; Fong, H. H.; Farnsworth, N. R.; Kinghorn, A. D.; Mehta, R. G.; Moon, R. C.; Pezzuto, J. M. Cancer chemopreventive activity of resveratrol, a natural product derived from grapes. *Science* 1997, 275, 218-220.
17. Ovesna, Z.; Horvathova-Kozics, K. Structure-activity relationship of trans-resveratrol and its analogs. *Neoplasma* 2005, 52, 450-455.

18. Orallo, F. Comparative studies of the antioxidant effects of cis- and trans-resveratrol. *Curr. Med. Chem.* 2006, 13, 87-98.
19. Lu, M.; Cai, Y. J.; Fang, J. G.; Zhou, Y. L.; Liu, Z. L.; Wu, L. M. Efficiency and structure-activity relationship of the antioxidant action of resveratrol and its analogs. *Pharmazie* 2002, 57, 474-478.
20. Stojanovic, S.; Sprinz, H.; Brede, O. Efficiency and mechanism of the antioxidant action of trans-resveratrol and its analogues in the radical liposome oxidation. *Arch. Biochem. Biophys.* 2001, 391, 79-89.
21. Stivala, L. A.; Savio, M.; Carafoli, F.; Perucca, P.; Bianchi, L.; Maga, G.; Forti, L.; Pagnoni, U. M.; Albini, A.; Prosperi, E.; Vannini, V. Specific structural determinants are responsible for the antioxidant activity and the cell cycle effects of resveratrol. *J. Biol. Chem.* 2001, 276, 22586-22594.
22. Chung, M. I.; Teng, C. M.; Cheng, K. L.; Ko, F. N.; Lin, C. N. An antiplatelet principle of Veratrum formosanum. *Planta Med.* 1992, 58, 274-276.
23. Fremont, L.; Gozzelino, M. T.; Linard, A. Response of plasma lipids to dietary cholesterol and wine polyphenols in rats fed polyunsaturated fat diets. *Lipids* 2000, 35, 991-999.
24. Murias, M.; Handler, N.; Erker, T,; Pleban, K.; Ecker, G.; Saiko, P.; Szekeres, T.; Jager, W. Resveratrol analogues as selective cyclooxygenase-2 inhibitors: synthesis and structure-activity relationship. *Bioorg. Med. Chem.* 2004, 12, 5571-5578.
25. Shay, N. F.; Banz, W. J. Regulation of gene transcription by botanicals: novel regulatory mechanisms. *Annu. Rev. Nutr.* 2005, 25, 297-315.
26. Juan, S. H.; Cheng, T. H.; Lin, H. C.; Chu, Y. L.; Lee, W. S. Mechanism of concentration-dependent induction of heme oxygenase-1 by resveratrol in human aortic smooth muscle cells. *Biochem. Pharmacol.* 2005, 69, 41-48.
27. Kundu, J. K.; Shin, Y. K.; Surh, Y. J. Resveratrol inhibits phorbol ester-induced expression of COX-2 and activation of NF-kappaB in mouse skin by blocking IkappaB activity. *Carcinogenesis* 2006, Epub ahead of print.
28. Lee, B.; Moon, S-K. Resveratrol inhibits TNF-κ-induced proliferation and matrix metalloproteinase expression in human vascular smooth muscle cells. *J. Nutr.* 2005, 135, 2767-2773.
29. Liao, H. F.; Kuo, C. D.; Yang, Y. C.; Lin, C. P.; Tai, H. C.; Chen, Y. Y.; Chen, Y. J. Resveratrol enhances radiosensitivity of human non-small cell lung cancer NCI-H838 cells accompanied by inhibition of nuclear factor-kappa B activation. *J. Radiat. Res. (Tokyo)* 2005, 46, 387-393.
30. Bi, X. L.; Yang, J. Y.; Dong, Y. X.; Wang, J. M.; Cui, Y. H.; Ikeshima, T.; Zhao, Y. Q.; Wu, C. F. Resveratrol inhibits nitric oxide and TNF-alpha production by lipopolysaccharide-activated microglia. *Int. Immunopharmacol.* 2005, 5, 185-193.
31. Bellucci, G.; Chiappe, C.; Lo Moro, G. Crown ether catalyzed stereospecific synthesis of Z- and E-stilbenes by Wittig reaction in a solid-liquid two-phase system. *Tetrahedron Lett.* 1996, 37, 4225-4228.
32. Lion, C. J.; Matthews, C. S.; Stevens, M. F. G.; Westwell, A. D. Synthesis, antitumor evaluation, and apoptosis-inducing activity of hydroxylated (E)-stilbenes. *J. Med. Chem.* 2005, 48, 1292-1295.
33. Kang, G.; Kong, P. J.; Yuh, Y. J.; Lim, S. Y.; Yim, S. V.; Chun, W.; Kim, S. S. Curcumin suppresses lipopolysaccharide-induced cyclooxygenase-2 expression by inhibiting activator protein 1 and nuclear factor kappab bindings in BV2 microglial cells. *J. Pharmacol. Sci.* 2004, 94, 325-328.
34. Wieder, T.; Prokop, A.; Bagci, B.; Essmann, F.; Bernicke, D.; Schulze-Osthoff, K.; Dorken, B.; Schmalz, H. G.; Daniel, P. T.; Henze, G. Piceatannol, a hydroxylated analog of the chemopreventive agent resveratrol, is a potent inducer of apoptosis in the lymphoma cell line BJAB and in primary, leukemic lymphoblasts. *Leukemia* 2001, 15, 1735-1742.
35. Ashikawa, K.; Majumdar, S.; Banerjee, S.; Bharti, A. C.; Shishodia, S.; Aggarwal, B. B. Piceatannol inhibits TNF-induced NF-κB activation and NF-κB-mediated gene expression through suppression of IκBκ kinase and p65 phosphorylation. *J. Immunol.* 2002, 169, 6490-6497.
36. Rimando, A. M.; Cuendet, M.; Desmarchelier, C.; Mehta, R. G.; Pezzuto, J. M.; Duke, S. O. Cancer chemopreventive and antioxidant activities of pterostilbene, a naturally occurring analogue of resveratrol. *J. Agric. Food Chem.* 2002, 50, 3453-3457.
37. Tolomeo, M.; Grimaudo, S.; Di Cristina, A.; Roberti, M.; Pizzirani, D.; Meli, M.; Dusonchet, L.; Gebbia, N.; Abbadessa, V.; Crosta, L.; Barucchello, R.; Grisolia, G.; Invidiata, F.; Simoni, D. Pterostilbene and 3'-hydroxypterostilbene are effective apoptosis-inducing agents in MDR and BCR-ABL-expressing leukemia cells. *Int. J Biochem. Cell. Biol.* 2005, 37, 1709-1726.
38. Mann, S. K.; Mukhopadhyay, A.; Aggarwal, B. B. Resveratrol suppresses TNT-induced activation of nuclear transcription factors NF-κB, activator protein-1, and apoptosis: potential role of reactive oxygen intermediates and lipid peroxidation. *J. Immunol.* 2000, 164, 6509-6519.
39. Sizemore, N.; Lerner, N.; Dombrowski, N.; Sakurai, H.; Stark, G. R. Distinct roles of the IκB kinase a and b in liberating nuclear factor κB (NF-κB) from IB and in phosphorylating the p65 subunit of NF-κB. *J. Biol. Chem.* 2002, 277, 3863-3869.
40. Schlesier, K.; Harwat, M.; Bohm, V.; Bitsch, R. Assessment of antioxidant activity by using different in vitro methods. *Free Rad. Res.* 2002, 36, 177-187.
41. Re, R.; Pellegrini, N.; Proteggente, A.; Pannala, A.; Yang, M.; Rice-Evans, C. Antioxidant activity applying an improved ABTS radical cation decolorization assay. *Free Rad. Biol. Med.* 1999, 26, 1231-1237.
42. Benzie, I. F.; Strain, J. J. Ferric reducing/antioxidant power assay: direct measure of total antioxidant activity of biological fluids and modified version for simultaneous measurement of total antioxidant power and ascorbic acid concentrations. *Methods Enzymol.* 1999, 299, 15-27.
43. Begum, S. D.; Parthasarathi, J. A convenient synthesis of homobutein. *Ind. J. Chem., Sect. B* 1988, 27B, 464.

REFERENCES (SECOND SET)

1. Q Li and I M Verma (2002) NF-κB regulation in the immune system. Nature Reviews Immunology 2, 725-728. PMID: 12360211
2. E Shaulian and M Karin (2001) AP-1 in cell proliferation and survival. Oncogene 20, 2390-2400. PMID: 11402335
3. J Hess, P Angel and M Schorpp-Kistner (2004) AP-1 subunits: quarrel and harmony among siblings. J Cell Sci 117, 5965-5973. PMID: 15564374
4. Y J Shyu, C D Suarez and C D Hu (2008) Visualization of AP-1 NF-kappaB ternary complexes in living cells by using a BiFC-based FRET. Proc Natl Acad Sci 105, 151-156. PMID: 18172215

5. G Shen, W-S Jeong, R Hu and A-N T Kong (2005) Regulation of Nrf2, NF-κB, and AP-1 signaling pathways by chemopreventive agents. Antioxid Redox Signal 7, 1648-1663. PMID: 16356127
6. W W Weber, L A Hunsaker, C N Roybal, E V Bobrovnikova-Marjon, S F Abcouwer, R E Royer, L M Deck and D L Vander Jagt (2006) Activation of NFkB is inhibited by curcumin and related enones. Bioorg Med Chem 14, 2450-2461. PMID:16338138
7. W W Weber, L A Hunsaker, A M Gonzales, J J Heynekamp, R A Orlando, L M Deck and D L Vander Jagt (2006) TPA-induced up-regulation of activator protein-1 can be inhibited or enhanced by analogs of the natural product curcumin. Biochem Pharmacol 72, 928-940. PMID:16934760
8. J J Heynekamp, W W Weber, L A Hunsaker, A M Gonzales, R A Orlando, L M Deck and D L Vander Jagt (2006) Substituted trans-stilbenes, including analogs of the natural product resveratrol, inhibit the human tumor necrosis factor alpha-induced activation of transcription factor nuclear factor kappB. J Med Chem 49, 7182-7189. PMID:17125270
9. L M Deck, L A Hunsaker, A M Gonzales, R A Orlando and D L Vander Jagt (2008) Substituted trans-stilbenes can inhibit or enhance the TPA-induced up-regulation of activator protein-1. BMC Pharmacology 8, 19. PMID: 19000313
10. N O Solberg, R Chamberlin, L M Deck, J E Heidrich, D C Brown, C I Brady, T A Vander Jagt, M Garwood, M Bisoffi, V Severns, D L Vander Jagt and L O Sillerud (2013) Inhibition of NF-κB by treatment with trans-stilbenes concomitantly lowers Alzheimer's plaque formation and microglial activation in APP/PS-1 transgenic mouse brain. J Alzheimer's Disease, submitted

What is claimed is:

1. A method of a treating a subject afflicted with a skin disease or condition, the method comprising administering to the subject a composition comprising a therapeutically effective amount of a compound according to the chemical structure:

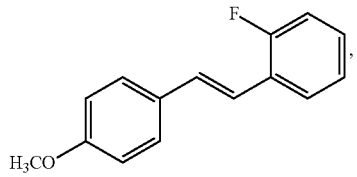 [SMILES: COc1ccc(/C=C/c2ccccc2F)cc1]

wherein said skin disease or condition is psoriasis.

2. The method according to claim 1, wherein the composition further comprises a pharmaceutically acceptable carrier, additive or excipient.

3. The method according to claim 1, wherein said psoriasis is psoriasis vulgaris.

4. The method according to claim 2, wherein said psoriasis is psoriasis vulgaris.

5. The method according to 1, wherein said subject is a human.

6. The method according to claim 2, wherein said subject is a human.

7. The method according to claim 3, wherein said subject is a human.

8. The method according to claim 4, wherein said subject is a human.

9. A method of reducing the likelihood of a psoriasis in a patient at risk, said method comprising administering to said patient an effective amount of a compound according to the chemical structure:

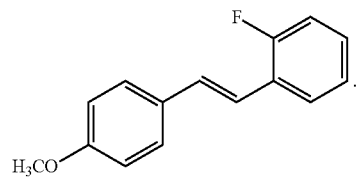

10. The method according to claim 9, wherein the composition further comprises a pharmaceutically acceptable carrier, additive or excipient.

11. The method according to claim 9, wherein said psoriasis is psoriasis vulgaris.

12. The method according to claim 10, wherein said psoriasis is psoriasis vulgaris.

13. The method according to claim 9, wherein said subject is a human.

14. The method according to claim 10, wherein said subject is a human.

15. The method according to claim 11, wherein said subject is a human.

16. The method according to claim 12, wherein said subject is a human.

* * * * *